US011778993B2

(12) United States Patent
Duchateau et al.

(10) Patent No.: US 11,778,993 B2
(45) Date of Patent: Oct. 10, 2023

(54) REPEAT VARIABLE DIRESIDUES FOR TARGETING NUCLEOTIDES

(71) Applicant: CELLECTIS, S.A., Paris (FR)

(72) Inventors: Philippe Duchateau, Draveil (FR); Alexandre Juillerat, Paris (FR); Claudia Bertonati, Paris (FR)

(73) Assignee: CELLECTIS, S.A., Paris (FR)

( * ) Notice: Subject to any disclaimer, the term of this patent is extended or adjusted under 35 U.S.C. 154(b) by 664 days.

(21) Appl. No.: 14/384,957

(22) PCT Filed: Mar. 15, 2013

(86) PCT No.: PCT/IB2013/000734
§ 371 (c)(1),
(2) Date: Sep. 12, 2014

(87) PCT Pub. No.: WO2013/136175
PCT Pub. Date: Sep. 19, 2013

(65) Prior Publication Data
US 2015/0067900 A1    Mar. 5, 2015

Related U.S. Application Data

(60) Provisional application No. 61/611,360, filed on Mar. 15, 2012.

(51) Int. Cl.
*A01K 67/027* (2006.01)
*C12N 15/63* (2006.01)
*C12N 5/10* (2006.01)
*C07K 5/06* (2006.01)
*C07K 14/00* (2006.01)
*C12N 9/22* (2006.01)
*C12N 15/10* (2006.01)
*C12N 15/82* (2006.01)

(52) U.S. Cl.
CPC ............ *A01K 67/0275* (2013.01); *C07K 5/06* (2013.01); *C07K 14/00* (2013.01); *C12N 5/10* (2013.01); *C12N 9/22* (2013.01); *C12N 15/63* (2013.01); *C12N 15/10* (2013.01); *C12N 15/82* (2013.01)

(58) Field of Classification Search
CPC ...... A01K 67/0275; C07K 5/06; C07K 14/00; C12N 5/10; C12N 9/22; C12N 15/63
USPC ............ 800/13; 435/455, 325, 199; 530/300
See application file for complete search history.

(56) References Cited

U.S. PATENT DOCUMENTS

| 9,567,573 B2 * | 2/2017 | Gregory ................ C12N 9/22 |
| 2011/0145940 A1 | 6/2011 | Voytas et al. |
| 2011/0239315 A1 | 9/2011 | Bonas et al. |
| 2011/0301073 A1 * | 12/2011 | Gregory ................ C12N 15/62 514/1.1 |
| 2013/0137173 A1 * | 5/2013 | Zhang .................... C12N 15/63 435/375 |

FOREIGN PATENT DOCUMENTS

WO    2011146121 A1    11/2011

OTHER PUBLICATIONS

Arnould, S., et al., "Engineering of Large Numbers of Highly Specific Homing Endonucleases that Induce Recombination on Novel DNA Targets.", JMB (2005), vol. 355, pp. 443-458.
Boch, J. et al., "Breaking the Code of DNA Binding Specificity of TAL-Type III Effectors ", Science (2009), vol. 326, pp. 1509-1512.
Bogdanove, A. et al., "TAL Effectors: Finding Plant Genes for Disease and Defense", COPB (2010), vol. 13, pp. 394-401.
Cermak, T. et al., "Efficient Design and Assembly of Custom TALEN and other TAL Effector-Based Constructs for DNA Targeting", NAR (2011), vol. 39:12, e82, 11 pgs.
Chames, P. et al., "In Vivo Selection of Engineered Homing Endonucleases Using Double-Strand Break Induced Homologous Recombination", NAR (2005), vol. 33:20, pp. e178, 10 pgs.
Christian, M. et al., "Targeting DNA Double-Strand Breaks With TAL Effector Nucleases", Genetics (2010), vol. 186, pp. 757-761.
Cong, L. et al., "Comprehensive Interrogation of Natural TALE DNA-Binding Modules and Transcriptional Repressor Domains", NAT.COMM. (2012), pp. 1-6.
Dayhoff, M. et al., "A Model of Evolutionary Change in Proteins", Atlas of Protein Sequence and Structure (1978), pp. 345-352.
Deng, D. et al., "Structural Basis for Sequence-Specific Recognition of DNA by TAL Effectors", Science (2012), vol. 335, pp. 720-723.
Epinat, J. et al., "A Novel Engineered Meganuclease Induces Homologous Recombination in Yeast and Mammallian Cells", NAR (2003), vol. 31:11, pp. 2952-2962.
Geibler, R. et al., "Transcriptional Activators of Human Genes With Programmable DNA-Specificity", PLoS ONE (2011), vol. 6:5, pp. 1-7.
Heinikoff, S. et al., "Amino Acid Substitution Matrices from Protein Blocks", PNAS (1992), vol. 89, pp. 10915-10919.

(Continued)

*Primary Examiner* — Anne Marie S Wehbe
(74) *Attorney, Agent, or Firm* — Arrigo, Lee, Guttman & Mouta-Bellum LLP

(57) ABSTRACT

The present invention relates to polypeptides and more particularly to Transcription Activator-Like Effector derived proteins that allow to efficiently target and/or process nucleic acids. The present invention also concerns methods to use these proteins. The present invention also relates to vectors, compositions and kits in which RVD domains and Transcription Activator-Like Effector (TALE) proteins of the present invention are used.

13 Claims, 15 Drawing Sheets

Figure 1:
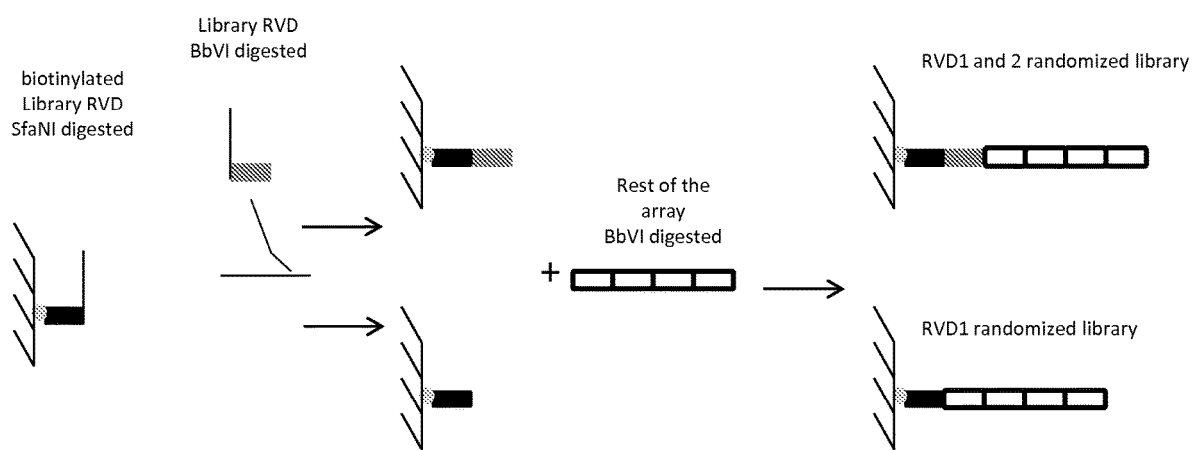

Specification includes a Sequence Listing.

(56) References Cited

OTHER PUBLICATIONS

Huang, P. et al., "Heritable Gene Targeting in Zebrafish Using Customized TALENs", Nat. Biotech. (2011), vol. 29:8, pp. 699-700.

Li, T. et al., "TAL Nucleases (TALNs): Hydrid Proteins Composed of TAL Effectors and FokI DNA-Cleavage Domain", NAR (2011), vol. 39:1, pp. 359-372.

Li, L. et al., "Rapid and Highly Efficient Construction of TALE-Based Transcriptional Regulators and Nucleases for Genome Modification", PMB (2012), vol. 78:4-5, pp. 407-416.

Mahfouz, M. M. et al., "Targeted Transcriptional Repression Using a Chimeric TALE-SRDX Repressor Protein", PMB (2012), vol. 78, pp. 311-321.

Mahfouz, M. M. et al., "De Novo-Engineered Transcription Activator-Like Effector (TALE) Hybrid Nuclease With Novel DNA Binding Specificity Creates Double-Strand Breaks", PNAS (2011), vol. 108:6, pp. 2623-2628.

Mak, A. et al., "The Crystal Structure of TAL Effector PthXo1 Bound to Its DNA Target", Science (2012), vol. 335, pp. 716-719.

Miller, J. et al., "A TALE Nuclease Architecture For Efficient Genome Editing", Nat. Biotech. (2011), vol. 29:2, pp. 143-148.

Morbitzer, R. et al., "Assembly of Custom TALE-Type DNA Binding Domains by Modular Cloning", NAR (2011), vol. 39:13, pp. 5790-5799.

Moscou, M. et al., "A Simple Cipher Governs DNA Recognition by TAL Effectors", Science (2009), vol. 326, p. 1501.

Murakami, M. et al., "The Repeat Domain of the Type III Effector Protein PthA Shows a TPR-ike Structure and Undergoes Conformational Changes Upon DNA Interaction", Proteins (2010), vol. 78, pp. 3386-3395.

Mussolino, C. et al., "A Novel TALE Nuclease Scaffold Enables High Genome Editing Activity in Combination With Low Toxicity", NAR (2011), vol. 39:21, pp. 9283-9293.

Rosen, L. et al., "Homing Endonuclease I-CreI Derivatives With Novel DNA Target Specificities", NAR (2006), vol. 34:17, pp. 4791-4800.

Sander, J. et al., "Targeted Gene Disruption in Somatic Zebrafish Cells Using Engineered TALENs", Nat. Biotech. (2011), vol. 29:8, pp. 697-698.

Smith, J. et al., "A Combinatorial Approach to Create Artificial Homing Endonucleases Cleaving Chosen Sequences", NAR (2006), vol. 34:22, e149, 12 pgs.

Streubel, J. et al., "TAL Effector RVD Specificities and Efficiencies", Nat. Biotech. (2012), vol. 10:7, pp. 393-395.

Tesson, L. et al., "Knockout Rats Generated by Embryo Microinjection of TALENs" Nat. Bitotech. (2011), vol. 29:8, pp. 695-696.

Weber, E. et al., "Assembly of Designer TAL Effectors by Golden Gate Cloning", PLos One (2011), vol. 6:5, e19722, 5 pgs.

Yakubovskaya, E. et al., "Helix Unwinding and Base Flipping Enable Human MTERF1 to Terminate Mitochondrial Transcription", Cell (2010), vol. 141:6, pp. 982-993.

Zhang, F. et al., "Efficient Construction of Sequence-Specific TAL Effectors for Modulating Mammalian Transcription", Nat. Bitotech. (2011), vol. 29:2, pp. 149-153.

* cited by examiner

| position array | Clone ID | a.a pos12 | a.a pos13 | A | C | G | T |
| --- | --- | --- | --- | --- | --- | --- | --- |
| 1 | 13102700 | H | A | 0,98 | 0,76 | 0,82 | 0,85 |
| 1 | 13075253 | H | A | 0,89 | 0,84 | 0,86 | 0,72 |
| 1 | 12765996 | N | A | 0,81 | 0,73 | 0,78 | 0,59 |
| 1 | 13103127 | P | A | 0,75 | 0,64 | 0,78 | 0,76 |
| 1 | 12766168 | P | C | 0,80 | 0,69 | 0,72 | 0,58 |
| 1 | 12793087 | T | C | 0,84 | 0,68 | 0,76 | 0,29 |
| 1 | 12793205 | Y | C | 0,79 | 0,69 | 0,71 | 0,40 |
| 1 | 13075205 | D | D | 0,62 | 0,51 | 0,00 | 0,37 |
| 1 | 13103083 | F | D | 0,74 | 0,71 | 0,00 | 0,00 |
| 1 | 13075594 | L | D | 0,49 | 0,60 | 0,00 | 0,16 |
| 1 | 12766221 | N | D | 0,77 | 0,75 | 0,34 | 0,00 |
| 1 | 13075087 | R | D | 0,84 | 0,88 | 0,00 | 0,15 |
| 1 | 13102891 | R | D | 0,81 | 0,76 | 0,00 | 0,00 |
| 1 | 12765967 | R | D | 0,66 | 0,67 | 0,15 | 0,00 |
| 1 | 13075214 | T | D | 0,74 | 0,74 | 0,28 | 0,00 |
| 1 | 13075353 | K | E | 0,75 | 0,67 | 0,00 | 0,00 |
| 1 | 13075377 | M | F | 0,79 | 0,00 | 0,00 | 0,15 |
| 1 | 13075264 | S | F | 0,84 | 0,18 | 0,18 | 0,00 |
| 1 | 13075268 | S | F | 0,83 | 0,18 | 0,17 | 0,00 |
| 1 | 13103172 | C | G | 0,84 | 0,75 | 0,71 | 0,93 |
| 1 | 12793262 | I | G | 0,53 | 0,40 | 0,42 | 0,72 |
| 1 | 13103154 | K | G | 0,87 | 0,48 | 0,81 | 0,72 |
| 1 | 13102845 | L | G | 0,60 | 0,46 | 0,30 | 0,89 |
| 1 | 13103162 | M | G | 0,71 | 0,47 | 0,40 | 0,88 |
| 1 | 12792672 | M | G | 0,49 | 0,40 | 0,35 | 0,80 |
| 1 | 13102968 | P | G | 0,48 | 0,00 | 0,12 | 0,87 |
| 1 | 13103147 | R | G | 0,46 | 0,00 | 0,89 | 0,00 |
| 1 | 13102826 | R | G | 0,41 | 0,00 | 0,86 | 0,00 |
| 1 | 13075505 | S | G | 0,93 | 0,79 | 0,96 | 0,00 |
| 1 | 13103126 | T | G | 0,70 | 0,54 | 0,58 | 0,79 |
| 1 | 13103185 | T | G | 0,93 | 0,44 | 0,90 | 0,00 |
| 1 | 13075319 | Y | G | 0,75 | 0,72 | 0,64 | 0,86 |
| 1 | 13075557 | I | H | 0,89 | 0,63 | 0,96 | 0,35 |
| 1 | 12792915 | R | H | 0,73 | 0,52 | 0,83 | 0,12 |
| 1 | 13075962 | Y | H | 0,94 | 0,82 | 0,94 | 0,00 |
| 1 | 12792692 | K | I | 0,80 | 0,28 | 0,42 | 0,00 |
| 1 | 13103086 | M | I | 0,90 | 0,00 | 0,00 | 0,00 |
| 1 | 13102690 | P | I | 0,98 | 0,41 | 0,25 | 0,72 |
| 1 | 12766111 | T | I | 0,81 | 0,18 | 0,37 | 0,00 |
| 1 | 13075357 | Y | I | 0,78 | 0,21 | 0,00 | 0,19 |

Figure 3a

| position array | Clone ID | a.a pos12 | a.a pos13 | A | C | G | T |
|---|---|---|---|---|---|---|---|
| 1 | 13103146 | C | K | 0,77 | 0,00 | 0,82 | 0,00 |
| 1 | 13103002 | F | K | 0,61 | 0,00 | 0,66 | 0,00 |
| 1 | 13075486 | H | K | 0,68 | 0,00 | 0,88 | 0,00 |
| 1 | 13075550 | N | K | 0,77 | 0,00 | 0,89 | 0,00 |
| 1 | 13102820 | N | K | 0,77 | 0,00 | 0,77 | 0,00 |
| 1 | 13102879 | S | K | 0,84 | 0,00 | 0,72 | 0,00 |
| 1 | 13103173 | T | K | 0,70 | 0,00 | 0,71 | 0,00 |
| 1 | 12792671 | C | L | 0,74 | 0,14 | 0,15 | 0,26 |
| 1 | 13075554 | F | L | 0,82 | 0,00 | 0,00 | 0,16 |
| 1 | 13075262 | K | L | 0,86 | 0,00 | 0,00 | 0,20 |
| 1 | 13103239 | P | L | 0,82 | 0,00 | 0,00 | 0,80 |
| 1 | 13075051 | D | N | 0,77 | 0,00 | 0,80 | 0,40 |
| 1 | 13102696 | G | N | 0,93 | 0,00 | 0,82 | 0,00 |
| 1 | 13075198 | T | N | 0,86 | 0,62 | 0,88 | 0,17 |
| 1 | 13103069 | T | N | 0,94 | 0,49 | 0,84 | 0,00 |
| 1 | 12766150 | Y | N | 0,79 | 0,55 | 0,82 | 0,57 |
| 1 | 13102887 | T | P | 0,80 | 0,28 | 0,17 | 0,88 |
| 1 | 13103195 | T | P | 0,62 | 0,29 | 0,18 | 0,77 |
| 1 | 13102975 | V | P | 0,74 | 0,57 | 0,52 | 0,83 |
| 1 | 13103217 | V | P | 0,66 | 0,59 | 0,46 | 0,82 |
| 1 | 12765930 | F | Q | 0,67 | 0,18 | 0,81 | 0,00 |
| 1 | 13075231 | G | Q | 0,67 | 0,00 | 0,91 | 0,15 |
| 1 | 13102778 | H | Q | 0,79 | 0,41 | 0,90 | 0,00 |
| 1 | 13102836 | I | Q | 0,66 | 0,14 | 0,76 | 0,07 |
| 1 | 13075951 | P | Q | 0,82 | 0,47 | 0,83 | 0,78 |
| 1 | 13075544 | P | Q | 0,69 | 0,49 | 0,88 | 0,69 |
| 1 | 13075119 | Q | Q | 0,60 | 0,00 | 0,80 | 0,00 |
| 1 | 13075582 | S | Q | 0,83 | 0,58 | 0,93 | 0,19 |
| 1 | 13102919 | T | Q | 0,78 | 0,44 | 0,82 | 0,00 |
| 1 | 13075413 | W | Q | 0,88 | 0,70 | 0,97 | 0,00 |
| 1 | 12792962 | F | R | 0,00 | 0,00 | 0,81 | 0,13 |
| 1 | 13075196 | G | R | 0,00 | 0,00 | 0,93 | 0,38 |
| 1 | 12793145 | H | R | 0,32 | 0,00 | 0,78 | 0,64 |
| 1 | 13102858 | L | R | 0,00 | 0,00 | 0,75 | 0,36 |
| 1 | 13075271 | S | R | 0,23 | 0,00 | 0,92 | 0,37 |
| 1 | 13103235 | V | R | 0,39 | 0,00 | 0,91 | 0,46 |

Figure 3b

| position array | Clone ID | a.a pos12 | a.a pos13 | A | C | G | T |
|---|---|---|---|---|---|---|---|
| 1 | 12793245 | G | S | 0,78 | 0,39 | 0,75 | 0,33 |
| 1 | 13102746 | G | S | 0,92 | 0,37 | 0,87 | 0,15 |
| 1 | 12766008 | K | S | 0,79 | 0,50 | 0,77 | 0,00 |
| 1 | 13102997 | L | S | 0,88 | 0,38 | 0,78 | 0,16 |
| 1 | 13075379 | P | S | 0,90 | 0,82 | 0,92 | 0,71 |
| 1 | 12766203 | T | S | 0,80 | 0,64 | 0,82 | 0,27 |
| 1 | 12793018 | T | S | 0,80 | 0,64 | 0,81 | 0,26 |
| 1 | 12793176 | V | S | 0,79 | 0,68 | 0,80 | 0,56 |
| 1 | 13103018 | W | S | 0,92 | 0,74 | 0,92 | 0,00 |
| 1 | 12793233 | Y | S | 0,80 | 0,67 | 0,80 | 0,35 |
| 1 | 13102989 | L | T | 0,73 | 0,00 | 0,62 | 0,16 |
| 1 | 12792997 | N | T | 0,81 | 0,45 | 0,83 | 0,00 |
| 1 | 12793361 | P | T | 0,73 | 0,35 | 0,67 | 0,56 |
| 1 | 13075071 | V | T | 0,89 | 0,67 | 0,90 | 0,64 |
| 1 | 13103240 | W | T | 0,88 | 0,43 | 0,91 | 0,00 |
| 1 | 12793342 | C | V | 0,73 | 0,48 | 0,72 | 0,27 |
| 1 | 12766352 | V | V | 0,74 | 0,57 | 0,63 | 0,37 |
| 1 | 13075477 | S | W | 0,72 | 0,00 | 0,00 | 0,15 |
| 1 | 13075239 | F | Y | 0,99 | 0,85 | 0,00 | 0,31 |
| 1 | 12766280 | F | Y | 0,80 | 0,70 | 0,00 | 0,12 |
| 1 | 13102731 | F | Y | 0,93 | 0,69 | 0,00 | 0,00 |
| 1 | 13102947 | G | Y | 0,86 | 0,24 | 0,00 | 0,00 |
| 1 | 13075586 | H | Y | 0,98 | 0,91 | 0,70 | 0,39 |
| 1 | 12766064 | S | Y | 0,77 | 0,42 | 0,14 | 0,12 |
| 1 | 12766173 | Y | Y | 0,83 | 0,73 | 0,13 | 0,13 |

Figure 3c

| position array | Clone ID | a.a pos12 | a.a pos13 | A | C | G | T |
|---|---|---|---|---|---|---|---|
| 2 | 13001877 | C | A | 0,69 | 0,70 | 0,46 | 0,67 |
| 2 | 13001622 | E | A | 0,47 | 0,50 | 0,32 | 0,65 |
| 2 | 13001570 | E | A | 0,47 | 0,60 | 0,33 | 0,60 |
| 2 | 13007784 | P | A | 0,83 | 0,76 | 0,75 | 0,40 |
| 2 | 13001937 | V | A | 0,52 | 0,67 | 0,26 | 0,73 |
| 2 | 13001569 | H | C | 0,88 | 0,94 | 0,61 | 0,37 |
| 2 | 13001836 | R | C | 0,85 | 0,76 | 0,42 | 0,31 |
| 2 | 13001825 | S | C | 0,89 | 0,82 | 0,52 | 0,50 |
| 2 | 13001439 | C | D | 0,48 | 0,79 | 0,00 | 0,00 |
| 2 | 13007491 | D | D | 0,57 | 0,85 | 0,11 | 0,47 |
| 2 | 13001943 | K | D | 0,41 | 0,84 | 0,00 | 0,00 |
| 2 | 13001786 | K | D | 0,35 | 0,71 | 0,00 | 0,00 |
| 2 | 13001520 | N | D | 0,71 | 0,91 | 0,00 | 0,08 |
| 2 | 13007455 | R | D | 0,51 | 0,89 | 0,14 | 0,14 |
| 2 | 13007794 | R | D | 0,34 | 0,71 | 0,00 | 0,00 |
| 2 | 13001384 | R | D | 0,34 | 0,74 | 0,00 | 0,00 |
| 2 | 13001759 | S | D | 0,62 | 0,90 | 0,00 | 0,00 |
| 2 | 13007875 | S | D | 0,57 | 0,81 | 0,00 | 0,00 |
| 2 | 13001617 | S | D | 0,54 | 0,80 | 0,00 | 0,00 |
| 2 | 13007655 | H | E | 0,70 | 0,79 | 0,00 | 0,00 |
| 2 | 13001374 | R | E | 0,17 | 0,60 | 0,00 | 0,00 |
| 2 | 13007599 | A | F | 0,77 | 0,16 | 0,15 | 0,15 |
| 2 | 13007371 | G | F | 0,77 | 0,00 | 0,00 | 0,00 |
| 2 | 13001382 | H | F | 0,84 | 0,80 | 0,13 | 0,00 |
| 2 | 13001918 | P | F | 0,90 | 0,76 | 0,00 | 0,00 |
| 2 | 13001854 | R | F | 0,77 | 0,17 | 0,00 | 0,00 |
| 2 | 13007513 | F | G | 0,55 | 0,72 | 0,46 | 0,70 |
| 2 | 13007871 | H | G | 0,60 | 0,70 | 0,54 | 0,91 |
| 2 | 13007543 | K | G | 0,84 | 0,80 | 0,49 | 0,96 |
| 2 | 13007847 | L | G | 0,48 | 0,66 | 0,14 | 0,79 |
| 2 | 13007515 | R | G | 0,85 | 0,91 | 0,73 | 0,95 |
| 2 | 13001872 | R | G | 0,71 | 0,86 | 0,48 | 0,85 |
| 2 | 13007353 | S | G | 0,92 | 0,89 | 0,69 | 0,98 |
| 2 | 13007417 | S | G | 0,79 | 0,90 | 0,67 | 0,91 |
| 2 | 13007485 | V | G | 0,35 | 0,04 | 0,00 | 0,71 |
| 2 | 13007864 | V | G | 0,34 | 0,15 | 0,00 | 0,70 |
| 2 | 13007627 | V | G | 0,21 | 0,15 | 0,15 | 0,69 |
| 2 | 13001787 | Y | G | 0,43 | 0,48 | 0,11 | 0,73 |
| 2 | 13001644 | Y | G | 0,37 | 0,42 | 0,09 | 0,69 |

Figure 4a

| position array | Clone ID | a.a pos12 | a.a pos13 | A | C | G | T |
|---|---|---|---|---|---|---|---|
| 2 | 13007882 | K | H | 0,52 | 0,18 | 0,74 | 0,00 |
| 2 | 13007503 | P | H | 0,87 | 0,49 | 0,92 | 0,16 |
| 2 | 13007881 | V | H | 0,41 | 0,00 | 0,66 | 0,00 |
| 2 | 13007560 | N | I | 0,88 | 0,64 | 0,57 | 0,00 |
| 2 | 13001468 | N | I | 0,87 | 0,64 | 0,45 | 0,00 |
| 2 | 13001565 | S | I | 0,77 | 0,60 | 0,16 | 0,16 |
| 2 | 13007449 | S | I | 0,82 | 0,40 | 0,19 | 0,15 |
| 2 | 13007826 | H | K | 0,66 | 0,00 | 0,76 | 0,00 |
| 2 | 13007607 | H | K | 0,52 | 0,17 | 0,81 | 0,00 |
| 2 | 13007698 | N | K | 0,40 | 0,18 | 0,79 | 0,15 |
| 2 | 13007691 | R | K | 0,19 | 0,00 | 0,72 | 0,00 |
| 2 | 13007620 | C | M | 0,80 | 0,67 | 0,15 | 0,13 |
| 2 | 13007689 | M | M | 0,71 | 0,29 | 0,00 | 0,18 |
| 2 | 13001756 | N | M | 0,85 | 0,86 | 0,15 | 0,00 |
| 2 | 13007401 | P | M | 0,87 | 0,70 | 0,00 | 0,00 |
| 2 | 13007527 | F | N | 0,42 | 0,16 | 0,56 | 0,12 |
| 2 | 13007542 | H | N | 0,86 | 0,34 | 0,86 | 0,00 |
| 2 | 13007656 | P | N | 0,70 | 0,20 | 0,68 | 0,00 |
| 2 | 13007520 | A | P | 0,35 | 0,21 | 0,14 | 0,64 |
| 2 | 13007604 | T | P | 0,00 | 0,00 | 0,00 | 0,63 |
| 2 | 13007918 | V | P | 0,00 | 0,00 | 0,00 | 0,71 |
| 2 | 13007625 | R | Q | 0,47 | 0,41 | 0,69 | 0,15 |
| 2 | 13007523 | E | R | 0,17 | 0,16 | 0,63 | 0,14 |
| 2 | 13007654 | H | R | 0,61 | 0,15 | 0,86 | 0,15 |
| 2 | 13007663 | P | R | 0,57 | 0,15 | 0,89 | 0,14 |
| 2 | 13007696 | Q | R | 0,15 | 0,12 | 0,71 | 0,00 |
| 2 | 13007428 | R | R | 0,32 | 0,00 | 0,78 | 0,00 |
| 2 | 13007382 | S | R | 0,37 | 0,00 | 0,78 | 0,41 |
| 2 | 13007700 | S | R | 0,34 | 0,00 | 0,76 | 0,41 |

Figure 4b

| position array | Clone ID | a.a pos12 | a.a pos13 | A | C | G | T |
|---|---|---|---|---|---|---|---|
| 2 | 13007801 | A | S | 0,69 | 0,84 | 0,82 | 0,67 |
| 2 | 13007540 | C | S | 0,96 | 0,84 | 0,85 | 0,79 |
| 2 | 13007827 | C | S | 0,65 | 0,74 | 0,84 | 0,60 |
| 2 | 13007559 | D | S | 0,74 | 0,23 | 0,66 | 0,00 |
| 2 | 13007568 | G | S | 0,75 | 0,71 | 0,69 | 0,42 |
| 2 | 13001928 | G | S | 0,80 | 0,65 | 0,54 | 0,35 |
| 2 | 13001920 | H | S | 0,90 | 0,85 | 0,73 | 0,53 |
| 2 | 13007816 | N | S | 0,92 | 0,82 | 0,89 | 0,67 |
| 2 | 13001903 | N | S | 0,91 | 0,86 | 0,81 | 0,61 |
| 2 | 13001534 | P | S | 0,91 | 0,72 | 0,67 | 0,22 |
| 2 | 13007580 | P | S | 0,89 | 0,73 | 0,87 | 0,00 |
| 2 | 13007360 | R | S | 0,95 | 0,82 | 0,80 | 0,78 |
| 2 | 13007726 | S | S | 0,95 | 0,82 | 0,87 | 0,82 |
| 2 | 13001516 | S | S | 0,90 | 0,89 | 0,82 | 0,77 |
| 2 | 13001757 | S | S | 0,90 | 0,90 | 0,72 | 0,69 |
| 2 | 13001705 | S | S | 0,90 | 0,84 | 0,78 | 0,68 |
| 2 | 13001853 | Y | S | 0,69 | 0,61 | 0,43 | 0,36 |
| 2 | 13007713 | F | T | 0,75 | 0,32 | 0,72 | 0,14 |
| 2 | 13007697 | N | T | 0,87 | 0,76 | 0,87 | 0,37 |
| 2 | 13001891 | Y | T | 0,69 | 0,36 | 0,41 | 0,00 |
| 2 | 13007398 | A | V | 0,84 | 0,83 | 0,66 | 0,78 |
| 2 | 13007386 | F | V | 0,74 | 0,29 | 0,52 | 0,00 |
| 2 | 13007621 | H | V | 0,83 | 0,72 | 0,75 | 0,14 |
| 2 | 13001608 | H | V | 0,81 | 0,78 | 0,52 | 0,00 |
| 2 | 13007817 | P | V | 0,73 | 0,16 | 0,17 | 0,00 |
| 2 | 13001583 | H | Y | 0,88 | 0,84 | 0,07 | 0,00 |
| 2 | 13001913 | H | Y | 0,88 | 0,75 | 0,00 | 0,00 |
| 2 | 13007919 | K | Y | 0,95 | 0,81 | 0,00 | 0,00 |

Figure 4c

| position array | Clone ID | a.a pos12 | a.a pos13 | A | C | G | T |
| --- | --- | --- | --- | --- | --- | --- | --- |
| 3 | 13038415 | G | A | 0,70 | 0,59 | 0,46 | 0,73 |
| 3 | 13047975 | L | A | 0,44 | 0,17 | 0,00 | 0,63 |
| 3 | 13047993 | L | A | 0,46 | 0,35 | 0,00 | 0,60 |
| 3 | 13047536 | L | A | 0,41 | 0,33 | 0,00 | 0,59 |
| 3 | 13047878 | V | A | 0,80 | 0,73 | 0,63 | 0,81 |
| 3 | 13038353 | P | C | 0,65 | 0,57 | 0,43 | 0,19 |
| 3 | 13047913 | H | D | 0,74 | 0,88 | 0,00 | 0,33 |
| 3 | 13038276 | N | D | 0,78 | 0,88 | 0,18 | 0,18 |
| 3 | 13047644 | S | D | 0,69 | 0,65 | 0,00 | 0,00 |
| 3 | 13038357 | S | D | 0,55 | 0,67 | 0,00 | 0,00 |
| 3 | 13047830 | A | F | 0,83 | 0,00 | 0,00 | 0,25 |
| 3 | 13047736 | C | F | 0,78 | 0,41 | 0,00 | 0,34 |
| 3 | 13047540 | C | F | 0,74 | 0,38 | 0,00 | 0,00 |
| 3 | 13048019 | F | F | 0,87 | 0,00 | 0,00 | 0,06 |
| 3 | 13038381 | N | F | 0,82 | 0,48 | 0,00 | 0,00 |
| 3 | 13047459 | Q | F | 0,84 | 0,00 | 0,00 | 0,00 |
| 3 | 13047881 | S | F | 0,70 | 0,00 | 0,00 | 0,33 |
| 3 | 13047599 | S | F | 0,59 | 0,00 | 0,00 | 0,24 |
| 3 | 13047602 | T | F | 0,78 | 0,00 | 0,00 | 0,05 |
| 3 | 13038747 | A | G | 0,76 | 0,72 | 0,53 | 0,80 |
| 3 | 13038349 | D | G | 0,69 | 0,59 | 0,00 | 0,62 |
| 3 | 13038446 | F | G | 0,65 | 0,55 | 0,36 | 0,75 |
| 3 | 13038310 | I | G | 0,77 | 0,60 | 0,18 | 0,77 |
| 3 | 13038414 | M | G | 0,68 | 0,64 | 0,46 | 0,75 |
| 3 | 13047963 | P | G | 0,67 | 0,69 | 0,43 | 0,71 |
| 3 | 13038500 | Q | G | 0,76 | 0,66 | 0,49 | 0,83 |
| 3 | 13038264 | Q | G | 0,76 | 0,63 | 0,42 | 0,82 |
| 3 | 13047824 | S | G | 0,94 | 0,86 | 0,68 | 0,92 |
| 3 | 13038347 | F | H | 0,70 | 0,56 | 0,45 | 0,00 |
| 3 | 13047732 | H | H | 0,89 | 0,86 | 0,82 | 0,43 |
| 3 | 13047865 | R | H | 0,85 | 0,74 | 0,72 | 0,34 |
| 3 | 13047986 | V | H | 0,76 | 0,55 | 0,65 | 0,00 |
| 3 | 13038767 | V | H | 0,63 | 0,45 | 0,57 | 0,00 |
| 3 | 13038717 | C | I | 0,92 | 0,80 | 0,72 | 0,26 |
| 3 | 13047911 | D | I | 0,84 | 0,46 | 0,19 | 0,00 |
| 3 | 13038348 | H | I | 0,89 | 0,77 | 0,80 | 0,00 |
| 3 | 13038710 | H | I | 0,89 | 0,75 | 0,74 | 0,00 |
| 3 | 13047969 | K | I | 0,86 | 0,80 | 0,65 | 0,26 |
| 3 | 13038385 | W | I | 0,93 | 0,56 | 0,43 | 0,00 |

Figure 5a

| position array | Clone ID | a.a pos12 | a.a pos13 | A | C | G | T |
|---|---|---|---|---|---|---|---|
| 3 | 13038671 | C | K | 0,65 | 0,37 | 0,84 | 0,57 |
| 3 | 13047906 | F | K | 0,41 | 0,00 | 0,79 | 0,31 |
| 3 | 13047944 | F | K | 0,40 | 0,00 | 0,75 | 0,29 |
| 3 | 13038583 | F | K | 0,40 | 0,00 | 0,74 | 0,19 |
| 3 | 13047516 | G | K | 0,70 | 0,42 | 0,72 | 0,61 |
| 3 | 13038643 | G | K | 0,65 | 0,42 | 0,69 | 0,61 |
| 3 | 13038373 | I | K | 0,77 | 0,37 | 0,81 | 0,66 |
| 3 | 13047474 | I | K | 0,75 | 0,36 | 0,89 | 0,62 |
| 3 | 13038545 | K | K | 0,67 | 0,35 | 0,84 | 0,51 |
| 3 | 13038401 | L | K | 0,00 | 0,00 | 0,64 | 0,00 |
| 3 | 13047958 | L | K | 0,00 | 0,00 | 0,75 | 0,00 |
| 3 | 13038410 | T | K | 0,73 | 0,50 | 0,81 | 0,70 |
| 3 | 13038354 | T | K | 0,75 | 0,54 | 0,81 | 0,67 |
| 3 | 13047647 | V | K | 0,81 | 0,16 | 0,83 | 0,54 |
| 3 | 13038629 | V | K | 0,65 | 0,18 | 0,83 | 0,53 |
| 3 | 13038778 | W | K | 0,18 | 0,00 | 0,68 | 0,00 |
| 3 | 13047887 | Y | K | 0,37 | 0,00 | 0,83 | 0,22 |
| 3 | 13038395 | A | L | 0,86 | 0,59 | 0,00 | 0,44 |
| 3 | 13038384 | C | L | 0,90 | 0,61 | 0,41 | 0,21 |
| 3 | 13038277 | C | L | 0,88 | 0,67 | 0,44 | 0,21 |
| 3 | 13047454 | D | L | 0,81 | 0,00 | 0,00 | 0,00 |
| 3 | 13038336 | G | L | 0,77 | 0,43 | 0,00 | 0,23 |
| 3 | 13038793 | I | L | 0,88 | 0,43 | 0,00 | 0,00 |
| 3 | 13047468 | I | L | 0,86 | 0,42 | 0,00 | 0,00 |
| 3 | 13047672 | I | L | 0,85 | 0,43 | 0,00 | 0,00 |
| 3 | 13047854 | L | L | 0,61 | 0,00 | 0,00 | 0,00 |
| 3 | 13038609 | R | L | 0,90 | 0,68 | 0,42 | 0,40 |
| 3 | 13047956 | R | L | 0,89 | 0,67 | 0,43 | 0,35 |
| 3 | 13038435 | S | L | 0,86 | 0,60 | 0,00 | 0,55 |
| 3 | 13047883 | T | L | 0,94 | 0,71 | 0,36 | 0,40 |
| 3 | 13038236 | T | L | 0,87 | 0,62 | 0,36 | 0,39 |
| 3 | 13038801 | T | L | 0,89 | 0,68 | 0,32 | 0,37 |
| 3 | 13047943 | Y | L | 0,72 | 0,29 | 0,00 | 0,00 |
| 3 | 13047598 | Y | L | 0,69 | 0,17 | 0,00 | 0,00 |
| 3 | 13047651 | Y | L | 0,68 | 0,16 | 0,00 | 0,00 |

Figure 5b

| position array | Clone ID | a.a pos12 | a.a pos13 | A | C | G | T |
|---|---|---|---|---|---|---|---|
| 3 | 13047713 | I | M | 0,81 | 0,68 | 0,00 | 0,06 |
| 3 | 13038337 | K | M | 0,88 | 0,86 | 0,36 | 0,45 |
| 3 | 13038490 | N | M | 0,90 | 0,88 | 0,50 | 0,22 |
| 3 | 13047841 | Q | M | 0,86 | 0,76 | 0,00 | 0,25 |
| 3 | 13038581 | Q | M | 0,81 | 0,63 | 0,00 | 0,18 |
| 3 | 13038656 | V | M | 0,83 | 0,69 | 0,00 | 0,19 |
| 3 | 13048017 | V | M | 0,92 | 0,68 | 0,00 | 0,09 |
| 3 | 13047981 | V | M | 0,72 | 0,61 | 0,00 | 0,05 |
| 3 | 13038362 | V | M | 0,77 | 0,67 | 0,00 | 0,00 |
| 3 | 13047560 | A | N | 0,72 | 0,36 | 0,66 | 0,35 |
| 3 | 13038708 | F | N | 0,80 | 0,00 | 0,71 | 0,00 |
| 3 | 13038400 | H | N | 0,88 | 0,40 | 0,85 | 0,00 |
| 3 | 13047785 | K | N | 0,85 | 0,46 | 0,76 | 0,30 |
| 3 | 13047895 | N | N | 0,94 | 0,62 | 0,84 | 0,00 |
| 3 | 13047859 | N | N | 0,91 | 0,58 | 0,88 | 0,00 |
| 3 | 13038655 | R | N | 0,81 | 0,46 | 0,73 | 0,19 |
| 3 | 13047451 | W | N | 0,92 | 0,17 | 0,74 | 0,00 |
| 3 | 13038403 | W | N | 0,88 | 0,35 | 0,76 | 0,00 |
| 3 | 13047714 | V | P | 0,69 | 0,50 | 0,37 | 0,75 |
| 3 | 13038350 | W | P | 0,74 | 0,51 | 0,18 | 0,51 |
| 3 | 13038427 | Y | P | 0,79 | 0,58 | 0,18 | 0,74 |
| 3 | 13038721 | C | Q | 0,76 | 0,63 | 0,75 | 0,45 |
| 3 | 13047855 | F | Q | 0,64 | 0,38 | 0,65 | 0,00 |
| 3 | 13038447 | I | Q | 0,68 | 0,52 | 0,64 | 0,17 |
| 3 | 13038250 | I | Q | 0,65 | 0,46 | 0,66 | 0,00 |
| 3 | 13038805 | I | Q | 0,62 | 0,51 | 0,66 | 0,00 |
| 3 | 13038476 | K | Q | 0,80 | 0,71 | 0,81 | 0,45 |
| 3 | 13038369 | K | Q | 0,80 | 0,63 | 0,80 | 0,21 |
| 3 | 13038694 | R | Q | 0,59 | 0,47 | 0,69 | 0,20 |
| 3 | 13038417 | W | Q | 0,68 | 0,39 | 0,58 | 0,29 |
| 3 | 13038662 | H | R | 0,66 | 0,33 | 0,75 | 0,28 |
| 3 | 13047452 | I | R | 0,85 | 0,37 | 0,66 | 0,60 |
| 3 | 13038528 | K | R | 0,67 | 0,22 | 0,69 | 0,52 |
| 3 | 13038449 | L | R | 0,19 | 0,00 | 0,47 | 0,00 |
| 3 | 13038233 | V | R | 0,71 | 0,39 | 0,61 | 0,64 |

Figure 5c

| position array | Clone ID | a.a pos12 | a.a pos13 | A | C | G | T |
|---|---|---|---|---|---|---|---|
| 3 | 13047671 | L | S | 0,69 | 0,36 | 0,43 | 0,37 |
| 3 | 13047478 | L | S | 0,69 | 0,32 | 0,37 | 0,35 |
| 3 | 13047983 | L | S | 0,70 | 0,35 | 0,43 | 0,34 |
| 3 | 13038742 | P | S | 0,87 | 0,50 | 0,71 | 0,39 |
| 3 | 13047833 | P | S | 0,94 | 0,44 | 0,78 | 0,38 |
| 3 | 13038587 | P | S | 0,88 | 0,43 | 0,70 | 0,22 |
| 3 | 13038442 | S | S | 0,96 | 0,75 | 0,85 | 0,67 |
| 3 | 13038241 | S | S | 0,91 | 0,62 | 0,84 | 0,61 |
| 3 | 13047826 | T | S | 0,96 | 0,79 | 0,82 | 0,77 |
| 3 | 13038383 | D | T | 0,75 | 0,47 | 0,54 | 0,20 |
| 3 | 13038707 | E | T | 0,94 | 0,85 | 0,84 | 0,85 |
| 3 | 13047931 | E | T | 0,89 | 0,84 | 0,82 | 0,64 |
| 3 | 13038731 | G | T | 0,76 | 0,58 | 0,54 | 0,53 |
| 3 | 13038733 | P | T | 0,77 | 0,57 | 0,61 | 0,19 |
| 3 | 13038244 | F | V | 0,90 | 0,89 | 0,58 | 0,44 |
| 3 | 13047668 | L | V | 0,74 | 0,79 | 0,41 | 0,35 |
| 3 | 13047757 | L | V | 0,72 | 0,69 | 0,39 | 0,33 |
| 3 | 13047972 | L | V | 0,73 | 0,69 | 0,37 | 0,31 |
| 3 | 13048012 | N | V | 0,96 | 0,90 | 0,89 | 0,59 |
| 3 | 13038651 | P | V | 0,67 | 0,69 | 0,58 | 0,21 |
| 3 | 13038420 | T | V | 0,94 | 0,85 | 0,68 | 0,84 |
| 3 | 13038330 | S | W | 0,65 | 0,00 | 0,50 | 0,00 |
| 3 | 13047717 | K | Y | 0,69 | 0,36 | 0,00 | 0,00 |
| 3 | 13047497 | N | Y | 0,91 | 0,64 | 0,33 | 0,05 |
| 3 | 13038378 | R | Y | 0,71 | 0,45 | 0,00 | 0,00 |
| 3 | 13047866 | S | Y | 0,69 | 0,36 | 0,00 | 0,34 |
| 3 | 13047636 | W | Y | 0,71 | 0,19 | 0,13 | 0,05 |

Figure 5d

| position array | Clone ID | a.a pos12 | a.a pos13 | A | C | G | T |
|---|---|---|---|---|---|---|---|
| 4 | 12901649 | G | A | 0,59 | 0,25 | 0,10 | 0,71 |
| 4 | 12901600 | H | A | 0,85 | 0,85 | 0,80 | 0,85 |
| 4 | 12901866 | D | C | 0,78 | 0,50 | 0,22 | 0,26 |
| 4 | 12901856 | E | C | 0,77 | 0,81 | 0,58 | 0,69 |
| 4 | 12902057 | I | C | 0,72 | 0,79 | 0,35 | 0,81 |
| 4 | 12901793 | I | C | 0,72 | 0,76 | 0,22 | 0,74 |
| 4 | 12901951 | R | C | 0,81 | 0,67 | 0,50 | 0,54 |
| 4 | 12901790 | Y | C | 0,84 | 0,86 | 0,66 | 0,67 |
| 4 | 12901853 | C | D | 0,68 | 0,84 | 0,00 | 0,54 |
| 4 | 12901500 | K | D | 0,70 | 0,87 | 0,00 | 0,59 |
| 4 | 12901633 | N | D | 0,78 | 0,93 | 0,24 | 0,63 |
| 4 | 12901505 | Q | D | 0,32 | 0,82 | 0,00 | 0,24 |
| 4 | 12854265 | Y | D | 0,54 | 0,86 | 0,00 | 0,41 |
| 4 | 12854278 | Y | D | 0,51 | 0,85 | 0,00 | 0,41 |
| 4 | 12901619 | A | E | 0,73 | 0,80 | 0,00 | 0,34 |
| 4 | 12853998 | E | E | 0,42 | 0,76 | 0,00 | 0,09 |
| 4 | 12901597 | H | E | 0,77 | 0,87 | 0,41 | 0,64 |
| 4 | 12901831 | H | E | 0,74 | 0,87 | 0,40 | 0,61 |
| 4 | 12853866 | Q | E | 0,67 | 0,77 | 0,00 | 0,10 |
| 4 | 12901745 | V | E | 0,45 | 0,77 | 0,00 | 0,41 |
| 4 | 12854164 | Y | E | 0,57 | 0,74 | 0,00 | 0,33 |
| 4 | 12901554 | Y | E | 0,53 | 0,75 | 0,00 | 0,24 |
| 4 | 12901521 | P | F | 0,78 | 0,25 | 0,00 | 0,00 |
| 4 | 12901722 | M | G | 0,79 | 0,73 | 0,45 | 0,82 |
| 4 | 12901610 | N | G | 0,80 | 0,69 | 0,55 | 0,88 |
| 4 | 12901735 | N | G | 0,80 | 0,70 | 0,51 | 0,86 |
| 4 | 12901746 | P | G | 0,68 | 0,52 | 0,09 | 0,81 |
| 4 | 12901653 | P | G | 0,83 | 0,78 | 0,62 | 0,79 |
| 4 | 12901699 | Q | G | 0,78 | 0,76 | 0,55 | 0,84 |
| 4 | 12854198 | V | G | 0,60 | 0,21 | 0,12 | 0,84 |
| 4 | 12901772 | V | G | 0,58 | 0,26 | 0,11 | 0,83 |
| 4 | 12901806 | R | H | 0,76 | 0,52 | 0,82 | 0,28 |
| 4 | 12901787 | C | I | 0,89 | 0,63 | 0,53 | 0,66 |
| 4 | 12901638 | I | I | 0,65 | 0,00 | 0,00 | 0,23 |
| 4 | 12854162 | S | I | 0,81 | 0,43 | 0,58 | 0,62 |
| 4 | 12901646 | T | I | 0,81 | 0,42 | 0,23 | 0,67 |
| 4 | 12853891 | Y | I | 0,85 | 0,33 | 0,49 | 0,00 |
| 4 | 12854090 | Y | I | 0,81 | 0,22 | 0,39 | 0,00 |

Figure 6a

| position array | Clone ID | a.a pos12 | a.a pos13 | A | C | G | T |
|---|---|---|---|---|---|---|---|
| 4 | 12901721 | A | K | 0,89 | 0,00 | 0,92 | 0,75 |
| 4 | 12854020 | D | K | 0,60 | 0,00 | 0,74 | 0,00 |
| 4 | 12854134 | D | K | 0,58 | 0,00 | 0,71 | 0,00 |
| 4 | 12854232 | H | K | 0,97 | 0,11 | 0,99 | 0,86 |
| 4 | 12854189 | N | K | 0,96 | 0,00 | 0,99 | 0,64 |
| 4 | 12854264 | P | K | 0,83 | 0,00 | 0,86 | 0,11 |
| 4 | 12854092 | Q | K | 0,82 | 0,00 | 0,93 | 0,39 |
| 4 | 12901491 | Q | K | 0,73 | 0,08 | 0,82 | 0,26 |
| 4 | 12854359 | R | K | 0,93 | 0,00 | 0,99 | 0,80 |
| 4 | 12853933 | S | K | 0,87 | 0,08 | 0,91 | 0,87 |
| 4 | 12854116 | T | K | 0,69 | 0,00 | 0,89 | 0,71 |
| 4 | 12854329 | V | K | 0,49 | 0,00 | 0,88 | 0,67 |
| 4 | 12854282 | V | K | 0,56 | 0,00 | 0,90 | 0,65 |
| 4 | 12901546 | V | K | 0,48 | 0,00 | 0,86 | 0,62 |
| 4 | 12901791 | H | L | 0,80 | 0,00 | 0,10 | 0,00 |
| 4 | 12901871 | I | L | 0,58 | 0,16 | 0,00 | 0,00 |
| 4 | 12901615 | K | L | 0,76 | 0,00 | 0,00 | 0,00 |
| 4 | 12902048 | N | L | 0,82 | 0,00 | 0,00 | 0,00 |
| 4 | 12902050 | N | L | 0,79 | 0,00 | 0,00 | 0,00 |
| 4 | 12901692 | N | L | 0,76 | 0,00 | 0,00 | 0,00 |
| 4 | 12901578 | N | L | 0,76 | 0,00 | 0,00 | 0,00 |
| 4 | 12854228 | S | L | 0,67 | 0,11 | 0,00 | 0,09 |
| 4 | 12854110 | S | L | 0,74 | 0,14 | 0,00 | 0,00 |
| 4 | 12901623 | C | M | 0,73 | 0,65 | 0,00 | 0,29 |
| 4 | 12853893 | N | M | 0,88 | 0,78 | 0,00 | 0,43 |
| 4 | 12901512 | N | M | 0,84 | 0,75 | 0,00 | 0,27 |
| 4 | 12854239 | Q | M | 0,72 | 0,46 | 0,00 | 0,21 |
| 4 | 12854263 | S | M | 0,71 | 0,62 | 0,00 | 0,38 |
| 4 | 12854220 | Y | M | 0,78 | 0,58 | 0,00 | 0,00 |
| 4 | 12854014 | Y | M | 0,76 | 0,62 | 0,00 | 0,00 |
| 4 | 12853901 | A | N | 0,82 | 0,34 | 0,87 | 0,09 |
| 4 | 12854040 | A | N | 0,82 | 0,22 | 0,89 | 0,00 |
| 4 | 12853930 | E | N | 0,77 | 0,18 | 0,79 | 0,00 |
| 4 | 12901849 | F | N | 0,74 | 0,00 | 0,76 | 0,00 |
| 4 | 12901717 | G | N | 0,70 | 0,00 | 0,71 | 0,00 |
| 4 | 12901804 | H | N | 0,87 | 0,60 | 0,87 | 0,00 |
| 4 | 12854057 | M | N | 0,60 | 0,00 | 0,63 | 0,00 |
| 4 | 12901680 | P | N | 0,85 | 0,52 | 0,83 | 0,00 |
| 4 | 12853997 | S | N | 0,83 | 0,24 | 0,89 | 0,11 |
| 4 | 12853912 | T | N | 0,69 | 0,00 | 0,76 | 0,12 |
| 4 | 12854288 | T | N | 0,62 | 0,00 | 0,68 | 0,00 |
| 4 | 12853871 | W | N | 0,87 | 0,09 | 0,86 | 0,00 |
| 4 | 12854175 | Y | N | 0,79 | 0,18 | 0,84 | 0,00 |
| 4 | 12854142 | Y | N | 0,78 | 0,19 | 0,83 | 0,00 |

Figure 6b

| position array | Clone ID | a.a pos12 | a.a pos13 | A | C | G | T |
|---|---|---|---|---|---|---|---|
| 4 | 12901763 | C | P | 0,65 | 0,61 | 0,28 | 0,84 |
| 4 | 12854165 | F | P | 0,53 | 0,27 | 0,13 | 0,76 |
| 4 | 12854402 | H | P | 0,82 | 0,76 | 0,67 | 0,83 |
| 4 | 12853869 | L | P | 0,22 | 0,00 | 0,00 | 0,78 |
| 4 | 12854161 | M | P | 0,41 | 0,08 | 0,29 | 0,75 |
| 4 | 12901810 | Q | P | 0,68 | 0,52 | 0,11 | 0,79 |
| 4 | 12854015 | T | P | 0,64 | 0,42 | 0,09 | 0,82 |
| 4 | 12901634 | T | P | 0,59 | 0,30 | 0,09 | 0,81 |
| 4 | 12902052 | H | Q | 0,87 | 0,83 | 0,88 | 0,80 |
| 4 | 12901809 | H | Q | 0,86 | 0,83 | 0,84 | 0,63 |
| 4 | 12901525 | H | Q | 0,84 | 0,87 | 0,90 | 0,63 |
| 4 | 12901930 | H | Q | 0,81 | 0,81 | 0,86 | 0,61 |
| 4 | 12901531 | K | Q | 0,74 | 0,80 | 0,88 | 0,68 |
| 4 | 12870175 | N | Q | 0,80 | 0,82 | 0,83 | 0,49 |
| 4 | 12901916 | P | Q | 0,69 | 0,58 | 0,63 | 0,14 |
| 4 | 12901724 | Q | Q | 0,71 | 0,62 | 0,84 | 0,26 |
| 4 | 12901601 | R | Q | 0,80 | 0,78 | 0,84 | 0,55 |
| 4 | 12901811 | S | Q | 0,74 | 0,74 | 0,81 | 0,59 |
| 4 | 12853999 | V | Q | 0,56 | 0,66 | 0,79 | 0,69 |
| 4 | 12901494 | K | R | 0,85 | 0,00 | 0,78 | 0,78 |
| 4 | 12854017 | M | R | 0,37 | 0,00 | 0,25 | 0,57 |
| 4 | 12854222 | N | R | 0,88 | 0,00 | 0,89 | 0,85 |
| 4 | 12901725 | N | R | 0,89 | 0,00 | 0,89 | 0,85 |
| 4 | 12854021 | Q | R | 0,72 | 0,00 | 0,60 | 0,70 |
| 4 | 12853861 | S | R | 0,96 | 0,37 | 0,81 | 0,90 |
| 4 | 12853981 | S | R | 0,82 | 0,22 | 0,81 | 0,89 |
| 4 | 12854000 | S | R | 0,86 | 0,25 | 0,75 | 0,86 |
| 4 | 12853905 | S | R | 0,85 | 0,23 | 0,80 | 0,84 |
| 4 | 12854117 | V | R | 0,42 | 0,00 | 0,53 | 0,87 |
| 4 | 12854362 | D | S | 0,67 | 0,35 | 0,60 | 0,44 |
| 4 | 12853951 | D | S | 0,71 | 0,19 | 0,61 | 0,43 |
| 4 | 12853910 | I | S | 0,43 | 0,23 | 0,11 | 0,69 |
| 4 | 12902062 | P | S | 0,77 | 0,72 | 0,60 | 0,25 |
| 4 | 12901817 | Q | S | 0,80 | 0,62 | 0,75 | 0,70 |
| 4 | 12854297 | S | S | 0,87 | 0,36 | 0,86 | 0,10 |
| 4 | 12854187 | V | S | 0,67 | 0,56 | 0,51 | 0,72 |
| 4 | 12854255 | D | T | 0,73 | 0,24 | 0,65 | 0,45 |
| 4 | 12901618 | I | T | 0,70 | 0,64 | 0,33 | 0,75 |
| 4 | 12853968 | L | T | 0,72 | 0,38 | 0,49 | 0,53 |
| 4 | 12853964 | P | T | 0,78 | 0,40 | 0,64 | 0,09 |
| 4 | 12901691 | F | V | 0,77 | 0,59 | 0,57 | 0,11 |
| 4 | 12854060 | P | V | 0,77 | 0,07 | 0,44 | 0,00 |
| 4 | 12854294 | Q | V | 0,83 | 0,56 | 0,63 | 0,47 |
| 4 | 12901640 | V | V | 0,80 | 0,76 | 0,60 | 0,73 |
| 4 | 12901857 | V | V | 0,77 | 0,70 | 0,61 | 0,65 |
| 4 | 12901501 | H | Y | 0,85 | 0,66 | 0,00 | 0,00 |

Figure 6c

REPEAT VARIABLE DIRESIDUES FOR TARGETING NUCLEOTIDES

FIELD OF THE INVENTION

The present invention relates to polypeptides and more particularly to Transcription Activator-Like Effector derived proteins that allow to efficiently target and/or process nucleic acids. The present invention also concerns methods to use these proteins. The present invention also relates to vectors, compositions and kits in which Repeat Variable Diresidue (RVD) domains and Transcription Activator-Like Effector (TALE) proteins of the present invention are used.

BACKGROUND OF THE INVENTION

The DNA binding domain of a recently discovered new class of protein derived from Transcription Activator-Like Effectors (TALE), has been widely used for several applications in the field of genome engineering. The sequence specificity of this family of proteins used in the infection process by plant pathogens of the Xanthomonas genus is driven by an array of motifs of 33-35 amino acids repeats, differing essentially by the two positions 12 and 13 (Boch, Scholze et al. 2009; Moscou and Bogdanove 2009). The recent achievement of the high resolution structure of TAL effectors bound to DNA showed that each single base of the same strand in the DNA target is contacted by a single repeat (Deng, Yan et al. 2012; Mak, Bradley et al. 2012), with the specificity resulting from the two polymorphic amino acids of the repeat; the so-called RVDs (Repeat Variable Diresidue). The modularity of these DNA binding domains has been confirmed to a certain extent by assembly of designed TALE-derived protein with new specificities.

TAL effectors fused to a nuclease catalytic head (TALE-nuclease) to create new tools, especially for genome engineering applications have been shown to be active to various extents in cell-based assays in yeast, mammalian cells and plants (Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Elsaesser et al. 2011; Mussolino, Morbitzer et al. 2011; Sander, Cade et al. 2011; Tesson, Usal et al. 2011; Weber, Gruetzner et al. 2011; Zhang, Cong et al. 2011; Li, Piatek et al. 2012; Mahfouz, Li et al. 2012).

Despite the description in the literature of a dozen of natural RVDs and their predicted partner bases, researchers are mainly focusing on using four different RVD/base couples NI/A, HD/C, NN/G, and NG/T [(Huang, Xiao et al. 2011; Mahfouz, Li et al. 2011; Morbitzer, Elsaesser et al. 2011; Mussolino, Morbitzer et al. 2011; Mahfouz, Li et al. 2012; Mak, Bradley et al. 2012)]. In a previous study, the DNA binding specificity of alternative RVDs which target the base at the $6^{th}$ position have been tested (WO 2011/146121).

Moreover, up to now, researchers have only published successful use of TALE-nucleases without reporting how frequently a TALE-nuclease fails to work. The designs of these arrays still only relay on the published code (Boch, Scholze et al. 2009; Moscou and Bogdanove 2009) and in fact lead to a certain amount of inactive or weakly active molecules. There remains a need for designing new RVDs obeying to an improved code, allowing governing TALE/DNA interactions with high specificity and/or flexibility.

Here, the inventors have made the conjecture that new RVDs could replace existing ones by testing their binding to nucleotide bases at the first to the fourth positions of a TALE recognition domain and that this replacement could improve the overall specificity TALE nucleic acid recognition. By proceeding accordingly, the inventors identified a set of new RVDs with useful activity and specificity.

BRIEF SUMMARY OF THE INVENTION

In a general aspect, the present invention relates to polypeptides that allow to efficiently target and/or process nucleic acids. More particularly the present invention relates to Transcription Activator-Like Effector derived proteins and particularly to repeat sequences comprising highly specific Repeat Variable-Diresidue (RVD) that allow to efficiently target and process nucleic acids. The present invention also concerns methods to use these RVDs and Transcription Activator-Like Effector proteins or chimeric proteins comprising these repeat sequences with RVDs. The present invention also relates to vectors, compositions and kits in which RVDs and Transcription Activator-Like Effector proteins of the present invention are used.

BRIEF DESCRIPTION OF THE FIGURES AND TABLES

In addition to the preceding features, the invention further comprises other features which will emerge from the description which follows, as well as to the appended drawings. A more complete appreciation of the invention and many of the attendant advantages thereof will be readily obtained as the same becomes better understood by reference to the following Figures in conjunction with the detailed description below.

FIG. 1: Schematic representation of the solid support method for synthesizing RVDs arrays used to prepare the libraries 1 to 8.

Figure 2:
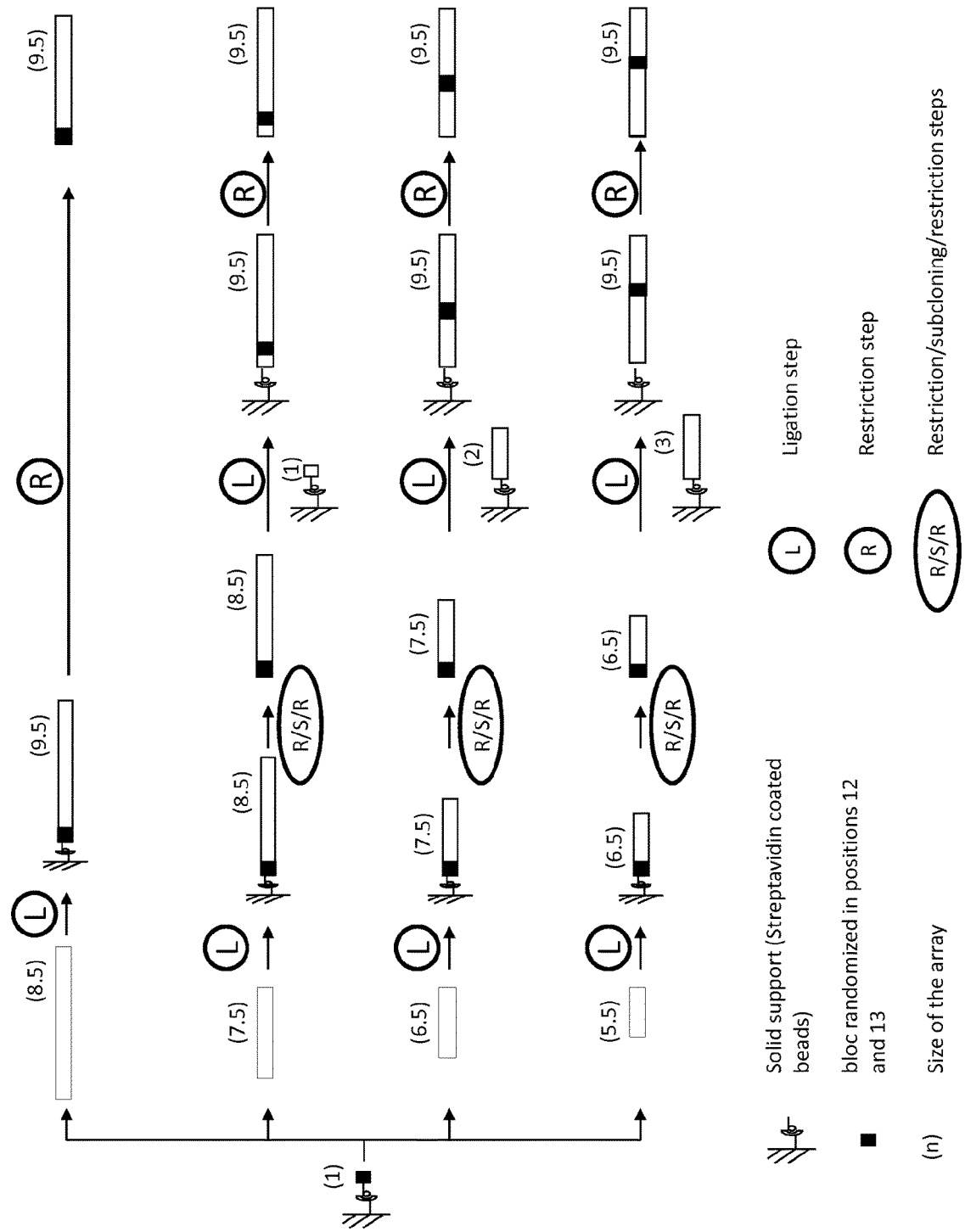

FIG. 2: Schematic representation of the solid support method for synthesizing RVDs arrays used to prepare the libraries A, B, C and D.

FIG. 3: a-c: TALE-Nuclease cleavage activity levels of individual clones of the library A on their respective targets (SEQ ID NO: 94 to SEQ ID NO: 97) containing A, C, G or T at the position 1 of the TALE array in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006). Values are comprised between 0 and 1. Maximal value is 1.

FIG. 4: a-c: TALE-Nuclease cleavage activity levels of individual clones of the library B on their respective targets (SEQ ID NO: 98 to SEQ ID NO: 101) containing A, C, G or T at the position 2 of the TALE array in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006). Values are comprised between 0 and 1. Maximal value is 1.

FIG. 5: a-d: TALE-Nuclease cleavage activity levels of individual clones of the library C on their respective targets (SEQ ID NO: 102 to SEQ ID NO: 105) containing A, C, G or T at the position 3 of the TALE array our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006). Values are comprised between 0 and 1. Maximal value is 1.

FIG. 6: a-c: TALE-Nuclease cleavage activity levels of individual clones of the library D on their respective targets (SEQ ID NO: 106 to SEQ ID NO: 109) containing A, C, G or T at the position 4 of the TALE array our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006). Values are comprised between 0 and 1. Maximal value is 1.

Table 1: List of oligonucleotides (5'→3') used to introduce diversity in positions 12 and 13 in libraries of a HD bloc in example 1.

Table 2: Target collections for libraries screening in example 1.

Table 3: Mean activities of three clones with one RVD randomized on a series of targets (SEQ ID NO: 62-77) in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 30° C. − indicates no detectable activity, + indicates low activity, ++ medium activity and +++ high activity.

Table 4: List of oligonucleotides (5'→3') used to introduce diversity in position 12 and 13 of a NG bloc in example 2.

Table 5: List of pseudo-palindromic sequences targets (two identical recognition sequences are placed facing each other on both DNA strands) in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 30° C., used for activity screens in yeast of libraries A, B, C and D.

Table 6: List of heterodimeric sequences targets (two different recognition sequences are placed facing each other on both DNA strands) in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 37° C., used for activity screens in yeast of NM/LP and SD/VG containing half-TALE-Nuclease.

Table 7: Activities of the three TALE-Nuclease pairs on heterodimeric sequence target A and B (two identical recognition sequences are placed facing each other on both DNA strands) in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 30° C. ++ indicates medium activity and +++ high activity.

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The present invention allows governing TALE/nucleic acid interactions in several directions by using arrays of particular RVDs in the repeat sequences of a TALE. The present invention allows to increase the specificity of a RVD array to one target compared to all other possible targets therefore reducing the off-target TALE/DNA interactions by using highly specific RVDs compared to natural RVDs.

New RVDs according to the present invention are selected from the group consisting of:
  II, TI, YI, PI, SI, CL, DL FL, GL, HL, IL, KL, LL, YL, MM, WY, PV, SW, XF for recognizing A, wherein X represents one amino acid residue selected from the group of A, G, V, L, I, M, S, T, C, P, D, E, F, Y, W, Q, N, H, R and K;
  RE, QD for recognizing C
  NK, RK, ER, FR, GR, LR, QR, RR, VR, WK, YK for recognizing G
  PG, AP, LP, MP, VP for recognizing T
  CD, DD, FD, LD, TD, AE, EE, KE, QE, YE, CM, IM, NM, PM, QM, SM, YM, VM, FY, GY, KY, MY, NY, RY, SY, YY, HY for recognizing A or C
  RG, PH, VH, CK, FK, PK, QK, TK, DN, EN FN, GN, KN, PN, RN, TN, YN, WN, FQ, GQ, HQ, IQ, QQ, TQ, FT, LT, VT, PR, DS, SS, FV for recognizing A or G
  MG, PL, VP for recognizing A or T.

As a non-limiting illustrative example, RVD "IL" can be used as a highly specific or recognizing a nucleotide A in a nucleic acid target sequence. The present invention also allows to increase the flexibility of a RVD array therefore targeting more than one target or only a desired set of desired targets by locally decreasing the specificity of a RVD; as a non-limiting illustrative example, RVD "VT" can be used as a flexible RVD which is able to recognize A or G in a nucleic acid target sequence. The present invention also allows to increase or decrease the activity of a RVD array on a nucleic acid target sequence; as a non-limiting illustrative example, RVD "SW" can be used as a specific RVD for recognize a nucleotide A in a target sequence as A is the only nucleotide it recognizes but with less strength than a RVD "IL" which specifically and strongly recognizes a nucleotide A (Table 3; SEQ ID: 19-25). Several applications may result from the present invention; as a non-limiting example, several allelic polymorphisms (Single Nucleotide Polymorphisms or SNPs) differing by one or a few nucleotides substitutions at a particular genomic locus can be targeted by the same array of RVDs according to the present invention, by using more or less specific and/or more or less flexible and/or more or less active RVDs according to the present invention. A method that could result from the present invention allows the treatment of a particular genetic disease by constructing and administering one unique TALE derived protein or chimeric protein according to the invention to every subjects in need thereof, whatever SNPs profiles around said mutation responsible for genetic disease in these subjects. Hence, said method of the present invention avoids the need to construct and administer one personalized TALE derived protein or chimeric protein for each subject in need thereof that takes into account each SNP profile around the mutation to cure. As another non-limiting example, flexible and/or specific and/or active RVDs can be used to target a particular gene in different species whatever minor variations in gene sequence can exist in each targeted species.

I. TALE Derived Protein Comprising New RVD(s)

In a general aspect, the present invention relates to proteins that allow to efficiently target and/or process nucleic acids. In a particular aspect, the present invention relates to a protein comprising a repeat domain (also named TALE array) wherein the repeat domain comprises at least one repeat sequence (or repeat unit) derived from a Transcription Activator-Like Effector (TALE) wherein at least one repeat sequence comprises one or more Repeat Variable Diresidue region (RVD) according to the present invention which is responsible for the binding of one specific nucleotide in nucleic acid target sequence.

In an embodiment, said repeat domain comprises a plurality of repeat sequences derived from a TALE. In another embodiment, said repeat domain comprises a plurality of repeat sequences derived from a TALE and at least another repeat sequence not derived from a TALE. In another embodiment, said repeat domain contains a plurality of repeat sequences derived from a TALE and at least another repeat sequence partially derived from a TALE. In another embodiment, said repeat domain contains a plurality of repeat sequences partially derived from a TALE. In another embodiment, said repeat sequences partially derived from a TALE can be obtained using substitution matrix for sequence alignment proteins. Non-limiting examples of substitution matrix for sequence alignment proteins include, for example, BLOSUM (Yakubovskaya, Mejia et al. 2010) or PAM Matrices (Dayhoff, M. O., Schwartz, R. and Orcutt, B. C. 1978). As non-limiting illustrative examples, repeat sequences obtained using BLOSUM substitution matrix are given by SEQ ID NO: 6 to 8. In another embodiment, said repeat sequences partially derived from a TALE can be obtained using homologous protein structures. Non-limiting examples of homologous protein structures include, for example, MTERF1 (mitochondria transcription terminator1) (Henikoff and Henikoff 1992) or tetratricopeptide repeat (TPR)-like domain (Murakami, M. T. et al. 2010). Non-limiting illustrative examples of repeat sequences partially derived from MTERF1 structures are given by SEQ ID NO: 15 to 18. In another embodiment, said repeat sequences not derived (partially derived) from a TALE can be obtained by modifying, as non-limiting examples, loop and/or helices regions. Non-limiting illustrative examples are given by SEQ ID NO: 1-5 and 9-14.

In a preferred embodiment, said repeat domain contains between 8 and 30 repeat sequences derived from a TALE, more preferably between 8 and 20, again more preferably 15. More preferably, repeat sequences of a TALE DNA binding domain according to the present invention comprising 8, 9, 10, 11, 12, 13, 14, 15, 16, 17, 18, 19, 20, 21, 22, 23, 24, 25, 26, 27, 28, 29, or 30 repeat sequences.

In another embodiment, said repeat sequences (or repeat units) are made of 30 to 42 amino acids, more preferably 33 to 35 amino acids, again more preferably 33 or 34 wherein two critical amino acids located at positions 12 and 13, i.e. Repeat Variable-Diresidue (RVD), mediates the recognition of one nucleotide in said nucleic acid target sequence. In another embodiment, RVDs comprise any known amino acid residues in positions 12 and 13. In a preferred embodiment, RVDs comprise one amino acid residue from the group consisting of A, G, V, L, I, M, S, T, C, P, D, E, F, Y, W, Q, N, H, R and K in position 12 according to amino acid one-letter code. In another preferred embodiment, RVDs comprise one amino acid residue from the group consisting of A, G, V, L, I, M, S, T, C, P, D, E, F, Y, W, Q, N, H, R and K in position 13 according to amino acid one-letter code. In another embodiment, RVDs comprise a combination of amino acid residues A, G, V, L, I, M, S, T, C, P, D, E, F, Y, W, Q, N, H, R and K according to amino acid one-letter code in positions 12 and 13 for recognizing nucleotides A, C, G and T in a nucleic acid target sequence. In a preferred embodiment, one or more RVD of repeat sequences is selected from the group consisting of:

II, TI, YI, PI, SI, CL, DL FL, GL, HL, IL, KL, LL, YL, MM, WY, PV, SW, XF for recognizing A, wherein X represents one amino acid residue selected from the group consisting of A, G, V, L, I, M, S, T, C, P, D, E, F, Y, W, Q, N, H, R and K;

RE, QD for recognizing C

NK, RK, ER, FR, GR, LR, QR, RR, VR, WK, YK for recognizing G

PG, AP, LP, MP, VP for recognizing T

CD, DD, FD, LD, TD, AE, EE, KE, QE, YE, CM, IM, NM, PM, QM, SM, YM, VM, FY, GY, KY, MY, NY, RY, SY, YY, HY for recognizing A or C RG, PH, VH, CK, FK, PK, QK, TK, DN, EN FN, GN, KN, PN, RN, TN, YN, WN, FQ, GQ, HQ, IQ, QQ, TQ, FT, LT, VT, PR, DS, SS, FV for recognizing A or G MG, PL, VP for recognizing A or T More particularly, the present invention relates to a Transcription Activator-Like Effector (TALE) DNA binding domain specific for a nucleic acid target sequence comprising a plurality of TALE repeat sequences (also named repeat units) containing each one a Repeat Variable Diresidue region (RVD) as described above which is responsible for the binding of one specific nucleotide pair in said nucleic acid target sequence. In a particular embodiment, further amino acid substitutions in positions 11 and 14 of one or several repeat sequences of said Transcription Activator-Like Effector (TALE) DNA binding domain specific for a nucleic acid target sequence can be present. Repeat sequences according to the invention can comprise a mutation on residue 14. In another embodiment, repeat sequences comprise one amino acid residue from the group consisting of A, G, V, L, I, M, S, T, C, P, D, E, F, Y, W, Q, N, H, R and K in position 14 according to amino acid one-letter code for recognizing nucleotides A, C, G and T. In another embodiment, RVDs comprise a combination of amino acid residues A, G, V, L, I, M, S, T, C, P, D, E, F, Y, W, Q, N, H, R and K according to amino acid one-letter code in positions 12, 13 and 14 for recognizing nucleotides A, C, G and T in a nucleic acid target sequence. In other words, the scope of the present invention encompasses Repeat Variable Triresidue responsible for the binding of one nucleotide in a nucleic acid target sequence.

In a further embodiment, repeat sequences comprise a mutation on residue 11 of the repeat sequence and can comprise one amino acid residue from the group consisting of A, G, V, L, I, M, S, T, C, P, D, E, F, Y, W, Q, N, H, R and K in position 11 according to amino acid one-letter code. In another embodiment, RVDs comprise a combination of amino acid residues A, G, V, L, I, M, 5, T, C, P, D, E, F, Y, W, Q, N, H, R and K according to amino acid one-letter code in positions 11, 12, 13 and 14 for recognizing nucleotides A, C, G and T in a nucleic acid target sequence. In other words, the present invention encompasses Repeat Variable Quadriresidue responsible for the binding of one nucleotide in a nucleic acid target sequence. In another embodiment, repeat sequences comprise a combination of amino acid residues A, G, V, L, I, M, S, T, C, P, D, E, F, Y, W, Q, N, H, R and K according to amino acid one-letter code in positions 11, 12 and 14, in positions 11, 13 and 14 or in positions 11, 12 and 13 for recognizing nucleotides A, C, G and T in a nucleic acid target sequence. In another embodiment, repeat sequences comprise a combination of amino acid residues A, G, V, L, I, M, S, T, C, P, D, E, F, Y, W, Q, N, H, R and K according to amino acid one-letter code in positions 12 and 14, 13 and 14, 11 and 14, 11 and 13 or in positions 11 and 12 for recognizing nucleotides A, C, G and T in a nucleic acid target sequence.

In another embodiment, the combination of amino acid residues present in positions 12 and 13 of a RVD "n" influences the combination of amino acid residues present in positions 12 and 13 of a RVD "n−1" or "n+1" in the repeat domain of the polypeptides of the present invention. In another embodiment, further amino acid substitutions in positions 11 and 14 of a RVD "n" can influence the combination of amino acid residues present in positions 12 and 13 of a RVD "n−1" or "n+1" in the repeat domain of the polypeptides of the present invention.

In preferred particular embodiment, repeat domain of the polypeptides of the present invention contains specific pairs of RVDs for recognizing specific pairs of nucleotides A, C, G and T in a nucleic acid target sequence. In another preferred embodiment, said specific pairs of RVDs for recognizing specific pairs of nucleotides A, C, G and T in a nucleic acid target sequence are different from the two RVDs able to individually recognize nucleotides composing said pair of nucleotides; in other words, said pairs of RVDs contain combinations of amino acid residues in positions 12 and 13 that are different from the combinations of amino acid residues present in positions 12 and 13 of the individual RVDs. As a non-limiting example, in the polypeptides of the present invention a pair of RVDs for recognizing nucleotides sequence "AG" can comprise amino acid residues in positions 12 and 13 different from pairs "TL-VT" or "VT-VT" that would result from the teaching of individual RVDs recognizing successive nucleotides A and G (Table 3; SEQ ID: 19-25). In another embodiment, further amino acid substitutions in positions 11 and 14 of one or two RVDs of a specific pair of RVDs for recognizing specific pairs of nucleotides A, C, G and T in a nucleic acid target sequence can be present.

In another particular embodiment, repeat domain of the polypeptides of the present invention contains specific triplets of RVDs for recognizing specific triplets of nucleotides A, C, G and T in a nucleic acid target sequence. In another preferred embodiment, said specific triplets of RVDs for recognizing specific triplets of nucleotides A, C, G and T in a nucleic acid target sequence are different from the three RVDs able to individually recognize nucleotides composing said triplet of nucleotides; in other words, said triplets of RVDs contain combinations of amino acid residues in positions 12 and 13 that are different from the combinations of amino acid residues present in positions 12 and 13 of the individual RVDs. As a non-limiting example, in the polypeptides of the present invention a triplet of RVDs for recognizing nucleotides sequence "AGG" can comprise amino acid residues in positions 12 and 13 different from triplets "IL-VT-VT" or "VT-VT-VT" that would result from the teaching of individual RVDs recognizing successive nucleotides A and G (Table 3; SEQ ID: 19-25). In another embodiment, further amino acid substitutions in positions 11 and 14 of one or two or three RVDs of a specific triplet of RVDs for recognizing specific triplets of nucleotides A, C, G and T in a nucleic acid target sequence can be present.

II. Chimeric TALE Derived Protein Comprising New RVD(s)

In another embodiment the present invention relates to a chimeric protein derived from a TALE corresponding to a fusion between a TALE DNA binding domain as mentioned above and an additional protein domain to process the nucleic acid within or adjacent to the specific nucleic acid target sequence. In other words, said polypeptide of the present invention is a chimeric protein derived from a TALE comprising:

(a) A Transcription Activator-Like Effector (TALE) DNA binding domain specific for a nucleic acid target sequence comprising a plurality of TALE repeat sequences comprising each one a Repeat Variable Diresidue region (RVD) which is responsible for the binding of one specific nucleotide in said nucleic acid target sequence; wherein one or more RVD is selected from the group consisting of:
II, TI, YI, PI, SI, CL, DL FL, GL, HL, IL, KL, LL, YL, MM, WY, PV, SW, XF for recognizing A, wherein X represents one amino acid residue selected from the group consisting of A, G, V, L, I, M, 5, T, C, P, D, E, F, Y, W, Q, N, H, R and K;
RE, QD for recognizing C
NK, RK, ER, FR, GR, LR, QR, RR, VR, WK, YK for recognizing G
PG, AP, LP, MP, VP for recognizing T
CD, DD, FD, LD, TD, AE, EE, KE, QE, YE, CM, IM, NM, PM, QM, SM, YM, VM, FY, GY, KY, MY, NY, RY, SY, YY, HY for recognizing A or C
RG, PH, VH, CK, FK, PK QK TK, DN, EN FN, GN, KN, PN, RN, TN, YN, WN, FQ, GQ, HQ, IQ, QQ, TQ, FT, LT, VT, PR, DS, SS, FV for recognizing A or G
MG, PL, VP for recognizing A or T
(b) An additional domain to process the nucleic acid within or adjacent to the specific nucleic acid target sequence.

In another embodiment, said chimeric protein according to the present invention can comprise at least one peptidic linker to fuse said TALE DNA binding domain and said additional protein domain processing the nucleic acid. In a preferred embodiment, said peptidic linker is flexible. In another preferred embodiment, said peptidic linker is structured.

In a particular embodiment, the additional protein domain of the chimeric protein of the present invention can be a transcription activator or repressor (i.e. a transcription regulator), or a protein that interacts with or modifies other proteins implicated in DNA processing. Non-limiting examples of DNA processing activities of said chimeric protein of the present invention include, for example, creating or modifying epigenetic regulatory elements, making site-specific insertions, deletions, or repairs in DNA, controlling gene expression, and modifying chromatin structure.

In another particular embodiment, said additional protein domain has catalytic activity selected from the group consisting of nuclease activity, polymerase activity, kinase activity, phosphatase activity, methylase activity, topoisomerase activity, integrase activity, transposase activity, ligase activity, helicase activity, recombinase activity. In a preferred embodiment, said additional protein domain is a nuclease, preferably an endonuclease; in another preferred embodiment, said protein domain is an exonuclease.

When comprising an endonuclease, said chimeric protein of the present invention derived from a TALE is a TALE-nuclease; in other words, in the scope of the present invention is a TALE-nuclease comprising:

(a) A Transcription Activator-Like Effector (TALE) DNA binding domain specific for a nucleic acid target sequence comprising a plurality of TALE repeat sequences comprising each one a Repeat Variable Diresidue region (RVD) which is responsible for the binding of one specific nucleotide in said nucleic acid target sequence, wherein one or more RVDs is selected from the group consisting of:
II, TI, YI, PI, SI, CL, DL FL, GL, HL, IL, KL, LL, YL, MM, WY, PV, SW, XF for recognizing A, wherein X represents one amino acid residue selected from the group consisting of A, G, V, L, I, M, S, T, C, P, D, E, F, Y, W, Q, N, H, R and K;
RE, QD for recognizing C
NK, RK, ER, FR, GR, LR, QR, RR, VR, WK, YK for recognizing G
PG, AP, LP, MP, VP for recognizing T
CD, DD, FD, LD, TD, AE, EE, KE, QE, YE, CM, IM, NM, PM, QM, SM, YM, VM, FY, GY, KY, MY, NY, RY, SY, YY, HY for recognizing A or C
RG, PH, VH, CK, FK, PK, QK, TK, DN, EN, FN, GN, KN, PN, RN, TN, YN, WN, FQ, GQ, HQ, IQ, QQ, TQ, FT, LT, VT, PR, DS, SS, FV for recognizing A or G
MG, PL, VP for recognizing A or T;

(b) An endonuclease domain to cleave the nucleic acid within or adjacent to the specific nucleic acid target sequence.

In another embodiment, further amino acid substitutions in positions 11 and 14 of one or several RVDs of said chimeric protein or TALE-nuclease according to the present invention can be present.

In a preferred embodiment, said TALE-nuclease according to the present invention can comprise at least one peptidic linker to fuse said TALE DNA binding domain and said endonuclease domain. In a preferred embodiment, said peptidic linker is flexible. In another preferred embodiment, said peptidic linker is structured.

Depending on the endonuclease domain that constitutes said TALE-nuclease according to the present invention, cleavage in the nucleic acid within or adjacent to the specific nucleic acid target sequence corresponds to either a double-stranded break or a single-stranded break.

As non limiting example, said endonuclease can be a type IIS FokI endonuclease domain or functional variant thereof which functions independently of the DNA binding domain and induces nucleic acid double-stranded cleavage as a dimer (Li, Wu et al. 1992; Kim, Cha et al. 1996). Amino acid sequence of FokI variants can be prepared by mutations in the DNA, which encodes the catalytic domain. Such variants include, for example, deletions from, or insertions or substitutions of, residues within the amino acid sequence. Any combination of deletion, insertion, and substitution may also be made to arrive at the final construct, provided that the final construct possesses the desired activity. Said nuclease domain of FokI variant according to the present invention comprises a fragment of a protein sequence having at least 80%, more preferably 90%, again more preferably 95% amino acid sequence identity with the protein sequence of FokI. In particular embodiment, a first and a second chimeric proteins can function respectively as monomer to act together as a dimer to process the nucleic acid within or adjacent to a specific nucleic acid target. As a non-limiting example, the two monomers can recognize different adjacent nucleic acid target sequences and the two protein domains constituting each chimeric protein derived from a TALE, function as subdomains that need to interact in order to process the nucleic acid within or adjacent to said specific nucleic acid target sequence.

In another particular embodiment, said chimeric protein is a monomeric TALE-nuclease that does not require dimerization for specific recognition and cleavage. As non limiting example, such monomeric TALE-nuclease comprises a TALE DNA binding domain fused to the catalytic domain of 1-TevI or a variant thereof.

It is understood that RVDs, DNA binding domains, TALE-nucleases, chimeric protein and polypeptides according to the present invention can also comprise single or plural additional amino acid substitutions or amino acid insertion or amino acid deletion introduced by mutagenesis process well known in the art. Is also encompassed in the scope of the present invention variants, functional mutants and derivatives from RVDs, DNA binding domains, TALE-nucleases, chimeric protein and polypeptides according to the present invention. Are also encompassed in the scope of the present invention RVDs, DNA binding domains, TALE-nucleases, chimeric proteins and polypeptides which present a sequence with high percentage of identity or high percentage of homology with sequences of RVDs, DNA binding domains, TALE-nucleases, chimeric proteins and polypeptides according to the present invention, at nucleotidic or polypeptidic levels. By high percentage of identity or high percentage of homology it is intended 70%, more preferably 75%, more preferably 80%, more preferably 85%, more preferably 90%, more preferably 95, more preferably 97%, more preferably 99% or any integer comprised between 70% and 99%.

In another aspect of the present invention are polynucleotides encoding for or comprising a coding sequence for the polypeptides, TALE DNA binding domain, chimeric protein derived from a TALE and TALE-nuclease according to the present invention. Is also encompassed a vector comprising such polynucleotides.

Is also encompassed in the scope of the present invention a host cell which comprises a vector and/or a recombinant polynucleotide encoding for or comprising a coding sequence for the polypeptides, TALE DNA binding domain, chimeric protein derived from a TALE and TALE-nuclease according to the present invention.

Is also encompassed in the scope of the present invention a non-human transgenic animal comprising a vector and/or a recombinant polynucleotide encoding for or comprising a coding sequence for the polypeptides, TALE DNA binding domain, chimeric protein derived from a TALE and TALE-nuclease according to the present invention.

Is also encompassed in the scope of the present invention a transgenic plant comprising a vector and/or a recombinant polynucleotide encoding for or comprising a coding sequence for the polypeptides, TALE DNA binding domain, chimeric protein derived from a TALE and TALE-nuclease according to the present invention.

The present invention also relates to a kit comprising a polypeptide or a TALE DNA binding domain or a chimeric protein derived from a TALE or a TALE-nuclease according to the present invention or a vector and/or a recombinant polynucleotide encoding for or comprising a coding sequence for such recombinant molecules and instructions for use said kit.

The present invention also relates to a composition comprising a polypeptide or a TALE DNA binding domain or a chimeric protein derived from a TALE or a TALE-nuclease according to the present invention or a vector and/or a recombinant polynucleotide encoding for or comprising a coding sequence for such recombinant molecules and a carrier. More preferably, is a pharmaceutical composition comprising such recombinant molecules and a pharmaceutically active carrier. For purposes of therapy, the chimeric protein according to the present invention and a pharmaceutically acceptable excipient are administered in a therapeutically effective amount. Such a combination is said to be administered in a "therapeutically effective amount" if the amount administered is physiologically significant. An agent is physiologically significant if its presence results in a detectable change in the physiology of the recipient. In the present context, an agent is physiologically significant if its presence results in a decrease in the severity of one or more symptoms of the targeted disease and in a genome correction of the lesion or abnormality.

III. Methods

In another aspect, the present invention also relates to methods for use of protein comprising TALE domain according to the present invention for various applications ranging from targeted nucleic acid cleavage to targeted gene regulation.

More particularly, the present invention relates to a method for binding a nucleic acid target sequence comprising:
(a) Selecting a nucleic acid target sequence;
(b) Engineering a protein comprising at least one Transcription Activator-Like Effector (TALE) domain wherein said TALE domain comprises a plurality of TALE repeat sequences comprising each one a Repeat Variable Diresidue region (RVD) which is responsible for the binding of one specific nucleotide in the nucleic acid target sequence, wherein one or more RVD is selected from the group consisting of:
II, TI, YI, PI, SI, CL, DL, FL, GL, HL, IL, KL, LL, YL, MM, WY, PV, SW, XF for recognizing A, wherein X represents one amino acid residue selected from the group consisting of A, G, V, L, I, M, S, T, C, P, D, E, F, Y, W, Q, N, H, R and K;
RE, QD for recognizing C
NK, RK, ER, FR, GR, LR, QR, RR, VR, WK, YK for recognizing G
PG, AP, LP, MP, VP for recognizing T
CD, DD, FD, LD, TD, AE, EE, KE, QE, YE, CM, IM, NM, PM, QM, SM, YM, VM, FY, GY, KY, MY, NY, RY, SY, YY, HY for recognizing A or C
RG, PH, VH, CK, FK, PK, QK, TK, DN, EN, FN, GN, KN, PN, RN, TN, YN, WN, FQ, GQ, HQ, IQ, QQ, TQ, FT, LT, VT, PR, DS, SS, FV for recognizing A or G
MG, PL, VP for recognizing A or T
(c) Contacting said engineered protein with said nucleic acid target sequence such that the engineered protein binds to said nucleic acid target sequence.

In particular embodiment, the present invention relates to a method for processing a genetic material in a cell comprising:
(a) Providing a cell comprising a nucleic acid target sequence;
(b) Engineering a protein comprising at least one Transcription Activator-Like Effector (TALE) domain wherein said TALE domain comprises a plurality of TALE repeat sequences comprising each one a Repeat Variable Diresidue region (RVD) which is responsible for the binding of one specific nucleotide in the nucleic acid target sequence, wherein one or more RVD is selected from the group consisting of:
II, TI, YI, PI, SI, CL, DL FL, GL, HL, IL, KL, LL, YL, MM, WY, PV, SW, XF for recognizing A, wherein X represents one amino acid residue selected from the group consisting of A, G, V, L, I, M, S, T, C, P, D, E, F, Y, W, Q, N, H, R and K;
RE, QD for recognizing C
NK, RK, ER, FR, GR, LR, OR, RR, VR, WK, YK for recognizing G
PG, AP, LP, MP, VP for recognizing T
CD, DD, FD, LD, TD, AE, EE, KE, QE, YE, CM, IM, NM, PM, QM, SM, YM, VM, FY, GY, KY, MY, NY, RY, SY, YY, HY for recognizing A or C
RG, PH, VH, CK, FK, PK, QK, TK, DN, EN, FN, GN, KN, PN, RN, TN, YN, WN, FQ, GQ, HQ, IQ, QQ, TQ, FT, LT, VT, PR, DS, SS, FV for recognizing A or G
MG, PL, VP for recognizing A or T
(c) Introducing said protein into a cell.

The term "processing" as used herein means that the sequence is considered modified simply by the binding of the protein. Any nucleic acid target sequence can be processed by the present methods. For example, the nucleic acid target sequence can be chromosomal, mitochondrial or chloroplast sequences.

In a more particular embodiment, said engineered protein of step (b) is a chimeric protein as described above further comprising an additional protein domain fused to the TALE domain. In a particular embodiment, the additional protein domain of the chimeric protein of the present invention can be a transcription activator or repressor (i.e. a transcription regulator), or a protein that interacts with or modifies other proteins implicated in DNA processing. Non-limiting examples of DNA processing activities of said chimeric protein of the present invention include, for example, creating or modifying epigenetic regulatory elements, making site-specific insertions, deletions, or repairs in DNA, controlling gene expression, and modifying chromatin structure.

In another embodiment, said additional protein domain has catalytic activity selected from the group consisting of nuclease activity, polymerase activity, kinase activity, phosphatase activity, methylase activity, topoisomerase activity, integrase activity, transposase activity, ligase activity, helicase activity, recombinase activity. In a preferred embodiment, said protein domain is a nuclease, preferably an endonuclease; in another preferred embodiment, said protein domain is an exonuclease.

The present invention more particularly relates to a method for modifying the genetic material of a cell within or adjacent to a nucleic acid target sequence. The double strand breaks caused by endonucleases are commonly repaired through non-homologous end joining (NHEJ). NHEJ comprises at least two different processes. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. The present invention relates to a method for modifying the genetic material in a cell within or adjacent to a nucleic acid target sequence by using chimeric protein, preferably a TALE-nuclease according to the present invention that allows nucleic acid cleavage that will lead to the loss of genetic information and any NHEJ pathway will produce targeted mutagenesis. In a preferred embodiment, the present invention related to a method for modifying the genetic material of a cell within or adjacent to a nucleic acid target sequence by generating at least one nucleic acid cleavage and a loss of genetic information around said nucleic acid target sequence thus preventing any scarless re-ligation by NHEJ. Said modification may be a deletion of the genetic material, insertion of nucleotides in the genetic material or a combination of both deletion and insertion of nucleotides.

The present invention also relates to a method for modifying nucleic acid target sequence further comprising the step of expressing an additional catalytic domain into a host cell. In a more preferred embodiment, the present invention relates to a method to increase mutagenesis wherein said additional catalytic domain is a DNA end-processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise of a protein domain or catalytically active derivate of the protein domain selected from the group consisting of hExoI (EXO1_HUMAN), Yeast ExoI (EXO1_YEAST), *E. coli* ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a preferred embodiment, said additional catalytic domain has a 3'-5'-exonuclease activity, and in a more preferred embodiment, said additional catalytic domain has TREX exonuclease activity, more preferably TREX2 activity. In another preferred embodiment, said catalytic domain is encoded by a single chain TREX polypeptide. Said additional catalytic domain may be fused to the chimeric protein according to the invention optionally by a peptide linker. It has been found that the coupling of the enzyme TREX2 with an endonuclease such as a TALE-nuclease ensures high frequency of targeted mutagenesis (WO2012/058458)

In a preferred embodiment, the present invention relates to a method for modifying the genetic material of a cell comprising:
(a) Providing a cell comprising a nucleic acid target sequence;
(b) Introducing a protein comprising at least:
  (i) A Transcription Activator-Like Effector (TALE) DNA binding domain specific for a nucleic acid target sequence comprising a plurality of TALE repeat sequences comprising each one a Repeat Variable Diresidue region (RVD) which is responsible for the binding of one specific nucleotide in said nucleic acid target sequence and wherein said TALE DNA binding domain comprises one or more RVDs selected from the group consisting of:
  II, TI, YI, PI, SI, CL, DL FL, GL, HL, IL, KL, LL, YL, MM, WY, PV, SW, XF for recognizing A, wherein X represents one amino acid residue selected from the group consisting of A, G, V, L, I, M, S, T, C, P, D, E, F, Y, W, Q, N, H, R and K;
  RE, QD for recognizing C
  NK, RK, ER, FR, GR, LR, QR, RR, VR, WK, YK for recognizing G
  PG, AP, LP, MP, VP for recognizing T
  CD, DD, FD, LD, TD, AE, EE, KE, QE, YE, CM, IM, NM, PM, QM, SM, YM, VM, FY, GY, KY, MY, NY, RY, SY, YY, HY for recognizing A or C
  RG, PH, VH, CK, FK, PK, QK, TK, DN, EN, FN, GN, KN, PN, RN, TN, YN, WN, FQ, GQ, HQ, IQ, QQ, TQ, FT, LT, VT, PR, DS, SS, FV for recognizing A or G
  MG, PL, VP for recognizing A or T
  (ii) An endonuclease,
(c) Inducing the expression of protein of (b);
(d) Selecting the cells in which cleavage within or adjacent to the specific nucleic acid target sequence has occurred.

In another embodiment, cells in which said protein has been introduced is selected by a selection method well-known in the art. As non-limiting example, said protein or chimeric protein can be introduced as a transgene encoded by a plasmidic vector; said plasmidic vector contains a selection marker which allows to identify and/or select cells which received said vector. Said protein expression can be induced in selected cells and said TALE domain of the protein bind nucleic acid target sequence in selected cells, thereby obtaining cells in which TALE domain binds a specific nucleic acid target sequence. The methods of the invention involve introducing a polynucleotide encoding engineered protein or chimeric protein into a cell. Vectors comprising targeting nucleic acid and/or nucleic acid encoding engineered protein or chimeric protein according to the present invention can be introduced into a cell by a variety of methods (e.g., injection, direct uptake, projectile bombardment, liposomes, electroporation). Engineered protein or chimeric proteins according to the present invention can be stably or transiently expressed into cells using expression vectors. Techniques of expression in eukaryotic cells are well known to those in the art. (See Current Protocols in Human Genetics: Chapter 12 "Vectors For Gene Therapy" & Chapter 13 "Delivery Systems for Gene Therapy"). The protein may be synthesized in situ in the cell as a result of the introduction of polynucleotide encoding protein into the cell. Alternatively, the protein could be produced outside the cell and then introduced thereto by well known method of the art.

Cells in which a cleavage-induced mutagenesis event, i.e. a mutagenesis event consecutive to an NHEJ event, has occurred can be identified and/or selected by well-known method in the art. As a non-limiting example, deep-sequencing analysis can be generated from the targeted cell genome around the targeted locus. Insertion/deletion events (mutagenesis events) can be therefore detected. As another non-limiting example, assays based on T7 endonuclease that recognizes non-perfectly matched DNA can be used, to quantify from a locus specific PCR on genomic DNA from provided cells, mismatches between reannealed DNA strands coming from cleaved/non-cleaved DNA molecules.

Endonucleolytic breaks are known to stimulate the rate of homologous recombination. Therefore, in another embodiment, the present invention relates to a method for inducing homologous gene targeting in the nucleic acid target sequence further comprising introducing into the cell an exogeneous nucleic acid comprising at least a sequence homologous to a portion of the nucleic acid target sequence, such that homologous recombination occurs between the target nucleic acid sequence and the exogeneous nucleic acid. In other words, following cleavage of the nucleic acid target sequence, a homologous recombination event is stimulated between the nucleic acid target sequence and the exogenous nucleic acid. By nucleic acid homologous sequence it is meant a nucleic acid sequence with enough identity to another one to lead to homologous recombination between sequences, more particularly having at least 80% identity, preferably at least 90% identity and more preferably at least 95%, and even more preferably 98% identity.

In another embodiment, said exogenous nucleic acid comprises two sequences homologous to portions or adjacent portions of said nucleic acid target sequence flanking a sequence to introduce in the nucleic acid target sequence. Preferably, said exogenous nucleic acid comprises first and second portions which are homologous to region 5' and 3' of the nucleic acid target, respectively. In another embodiment, said exogenous sequence allows introducing new genetic material into a cell. Said exogenous nucleic acid in this embodiment also comprises a third portion positioned between the first and the second portion which comprises no homology with the regions 5' and 3' of the nucleic acid target sequence. Said new genetic material introduced into a cell can confer a selective or a commercial advantage to said cell. In another embodiment, said exogenous sequence allows to replace genetic material into a cell. In another embodiment, said exogenous sequence allows to repair genetic material into a cell.

Preferably, homologous sequences of at least 50 bp, preferably more than 100 bp and more preferably more than 200 bp are used within said donor matrix. Therefore, the exogenous nucleic acid is preferably from 200 bp to 6000 bp, more preferably from 1000 bp to 2000 bp. Indeed, shared nucleic acid homologies are located in regions flanking upstream and downstream the site of the cleavage and the nucleic acid sequence to be introduced should be located between the two arms.

In particular embodiments, said exogenous nucleic acid can comprise a positive selection marker between the two homology arms and eventually a negative selection marker upstream of the first homology arm or downstream of the second homology arm. The marker(s) allow(s) the selection of the cells having inserted the sequence of interest by homologous recombination at the target site. Depending on the location of the targeted genome sequence wherein break event has occurred, such exogenous nucleic acid can be used to knock-out a gene, e.g. when exogenous nucleic acid is located within the open reading frame of said gene, or to introduce new sequences or genes of interest. Sequence insertions by using such exogenous nucleic acid can be used to modify a targeted existing gene, by correction or replacement of said gene (allele swap as a non-limiting example), or to up- or down-regulate the expression of the targeted gene (promoter swap as non-limiting example), said targeted gene correction or replacement. In a particular embodiment, the exogenous nucleic acid is included in a vector encoding the TALE-derived protein or chimeric protein or alternatively, in a different vector. In another particular embodiment, the exogenous nucleic acid is a single- or double stranded oligonucleotide.

Cells in which a homologous recombination event has occurred can be selected by methods well-known in the art. As a non-limiting example, PCR analysis using one oligonucleotide matching within the exogenous nucleic acid sequence and one oligonucleotide matching the genomic nucleic acid of cells outside said exogenous nucleic acid but close to the targeted locus can be performed. Therefore, cells in which methods of the invention allowed a mutagenesis event or a homologous recombination event to occur can be selected.

In another embodiment, said exogenous sequence to be introduced into a cell can be optimized in order to be not cleavable by the protein used to generate the initial double-stranded break. In other words, in the case where a nucleic acid target sequence has to be corrected by replacement consecutively to a double-stranded break generated by a protein or a chimeric protein according to the present invention, exogenous replacement sequence can be modified in order to be not cleavable again by the original protein or chimeric protein. Said modifications include as non-limiting example silent mutations when targeted sequence is in a coding sequence of a gene or mutations when targeted sequence is in a non-coding sequence of a gene.

Another aspect of the invention is a method for producing one Transcription Activator-Like Effector (TALE) domain comprising:
(a) Determining a nucleic acid target sequence;
(b) Synthesizing a repeat sequence domain specific for a nucleic acid target sequence comprising a plurality of TALE repeat sequences comprising each one a Repeat Variable Diresidue region (RVD) which is responsible for the binding of one specific nucleotide in said nucleic acid target sequence, wherein one or more RVD is selected from the group consisting of:
II, TI, YI, PI, SI, CL, DL FL, GL, HL, IL, KL, LL, YL, MM, WY, PV, SW, XF for recognizing A, wherein X represents one amino acid residue selected from the group consisting of A, G, V, L, I, M, S, T, C, P, D, E, F, Y, W, Q, N, H, R and K;
RE, QD for recognizing C;
NK, RK, ER, FR, GR, LR, QR, RR, VR, WK, YK for recognizing G;
PG, AP, LP, MP, VP for recognizing T;
CD, DD, FD, LD, TD, AE, EE, KE, QE, YE, CM, IM, NM, PM, QM, SM, YM, VM, FY, GY, KY, MY, NY, RY, SY, YY, HY for recognizing A or C;
RG, PH, VH, CK, FK, PK, QK, TK, DN, EN, FN, GN, KN, PN, RN, TN, YN, WN, FQ, GQ, HQ, IQ, QQ, TQ, FT, LT, VT, PR, DS, SS, FV for recognizing A or G;
MG, PL, VP for recognizing A or T.

In a particular embodiment, the present invention relates to a method for producing a chimeric protein further comprising:
(c) Providing an additional protein domain to process the nucleic acid within or adjacent to the specific nucleic acid target sequence;
(d) Optionally designing a peptidic linker to link TALE domain with said additional protein domain;
(e) Assembling said chimeric protein.

The scope of the present invention also encompasses a chimeric protein obtainable by a method comprising at least the steps of:
(a) Determining a nucleic acid target sequence;
(b) Synthesizing a repeat sequence domain specific for a nucleic acid target sequence comprising a plurality of TALE repeat sequences comprising each one a Repeat Variable Diresidue region (RVD) which is responsible for the binding of one specific nucleotide in said nucleic acid target sequence, wherein one or more RVD is selected from the group consisting of:
II, TI, VI, PI, SI, CL, DL, FL, GL, HL, IL, KL, LL, YL, MM, WY, PV, SW, XF for recognizing A, wherein X represents one amino acid residue selected from the group consisting of A, G, V, L, I, M, S, T, C, P, D, E, F, Y, W, Q, N, H, R and K;

RE, QD for recognizing C
NK, RK, ER, FR, GR, LR, QR, RR, VR, WK, YK for recognizing G
PG, AP, LP, MP, VP for recognizing T
CD, DD, FD, LD, TD, AE, EE, KE, QE, YE, CM, IM, NM, PM, QM, SM, YM, VM, FY, GY, KY, MY, NY, RY, SY, YY, HY for recognizing A or C
RG, PH, VH, CK, FK, PK, QK, TK, DN, EN FN, GN, KN, PN, RN, TN, YN, WN, FQ, GQ, HQ, IQ, QQ, TQ, FT, LT, VT, PR, DS, SS, FV for recognizing A or G
MG, PL, VP for recognizing A or T (c) Providing an additional protein domain to process the nucleic acid within or adjacent to the specific nucleic acid target sequence;
(d) Optionally designing a peptidic linker to link polypeptides obtained in b) and c);
(e) Assembling said chimeric protein;
(f) Testing the activity of said chimeric protein.

In a further embodiment, synthesis step b) can be done using a solid support method composed of consecutive restriction/ligation/washing steps as shown in FIG. 1 and examples section; step c) can be done by cloning said protein domain of interest into a plasmidic vector; in the case where said chimeric protein according to the invention is a TALE-nuclease, as non-limiting example, said protein domain can be cloned together in a same vector with chosen peptidic linker and eventual additional N and C terminal backbones for a RVD. Assembling step e) can be done by cloning repeat sequence domain of step b) in the vector resulting from step e). Testing step f) can be done, in the case where said chimeric protein is a TALE-Nuclease as a non-limiting example, in yeast by using a yeast target reporter plasmid containing the nucleic acid target sequence as previously described (International PCT Applications WO 2004/067736 and in (Epinat, Arnould et al. 2003; Chames, Epinat et al. 2005; Arnould, Chames et al. 2006; Smith, Grizot et al. 2006). The activity of said TALE-nuclease can be tested at 30° C. and 37° C. in a yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006)

In another embodiment, the cell targeted or modified by the methods of the present invention is a eukaryotic cell preferably a mammalian cell, a plant cell or an algal cell.

In another embodiment, the nucleic acid sequence targeted or modified by the methods of the present invention is a chromosomal sequence or an episomal sequence. In another embodiment, said sequence is an organelle sequence.

The present invention also related to a method for generating a plant comprising providing a plant cell comprising a nucleic acid target sequence into which it is desired to introduce a genetic modification; generating a cleavage within or adjacent to the nucleic acid target sequence by introducing a chimeric protein such as a TALE-nuclease according to the present invention; and generating a plant from the cell or progeny thereof, in which cleavage has occurred. Progeny includes descendants of a particular plant or plant line. In a particular embodiment, the method for generating a plant further comprises introducing an exogenous nucleic acid as desired. Said exogenous nucleic acid comprises a sequence homologous to at least a portion of the nucleic acid target sequence, such that homologous recombination occurs between said exogenous nucleic acid and the nucleic acid target sequence in the cell or progeny thereof. Plant cells produced using methods can be grown to generate plants having in their genome a modified nucleic acid target sequence. Seeds from such plants can be used to generate plants having a phenotype such as, for example, an altered growth characteristic, altered appearance, or altered compositions with respect to unmodified plants.

The polypeptides of the invention are useful to engineer genomes and to reprogram cells, especially induced Pluripotent Stem cells (iPS) and embryonic stem (ES) cells, preferably non human ES cells.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

DNA or nucleic acid processing activity refers to a particular/given enzymatic activity of a protein domain comprised in a chimeric protein or a polypeptide according to the invention such as in the expression "an additional protein domain to process the nucleic acid within or adjacent to the specific nucleic acid target sequence". Said DNA or nucleic acid processing activity can refer to a cleavage activity, either a cleavase activity either a nickase activity, more broadly a nuclease activity but also a polymerase activity, a kinase activity, a phosphatase activity, a methylase activity, a topoisomerase activity, an integrase activity, a transposase activity, a ligase, a helicase or recombinase activity as non-limiting examples.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

by "peptide linker" or "peptidic linker" it is intended to mean a peptide sequence which allows the connection of different monomers or different parts comprised in a fusion protein such as between a TALE DNA binding domain and a protein domain in a chimeric protein or a polypeptide according to the present invention and which allows the adoption of a correct conformation for said chimeric protein activity and/or specificity. Peptide linkers can be of various sizes, from 3 amino acids to 50 amino acids as a non limiting indicative range. Peptide linkers can also be qualified as structured or unstructured. Peptide linkers can be qualified as active linkers when they comprise active domains that are able to change their structural conformation under appropriate stimulation.

by "subdomain" or "domain" it is intended a protein subdomain or a protein part that interacts with another protein subdomain or protein part to form an active entity and/or a catalytic active entity bearing nucleic acid or DNA processing activity of said chimeric protein or polypeptide according to the invention.

by "DNA target", "DNA target sequence", "target DNA sequence", "nucleic acid target sequence", "target nucleic acid sequence", "target sequence", or "processing site" is intended a polynucleotide sequence that can be processed by a TALE derived protein or chimeric protein according to the present invention. These terms refer to a specific nucleic acid location, preferably a genomic location in a cell, but also a portion of genetic material that can exist independently to the main body of genetic material such as plasmids, episomes, virus, transposons or in organelles such as mitochondria or chloroplasts as non-limiting examples. The nucleic acid target sequence is defined by the 5' to 3' sequence of one strand of said target, as indicated for SEQ ID NO: 62-77 in table 2 and SES ID NO: 94-109 in table 5 as a non-limiting example.

Adjacent is used to distinguish between 1) the nucleic acid sequence recognized and bound by a set of specific RVDs comprised in the TALE DNA binding domain of a polypeptide or a chimeric protein according to the present invention and 2) the nucleic acid target sequence to be processed by said polypeptide or chimeric protein according to the invention, said nucleic sequences 1) and 2) being adjacent.

By "delivery vector" or "delivery vectors" is intended any delivery vector which can be used in the present invention to put into cell contact (i.e. "contacting") or deliver inside cells or subcellular compartments agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consist of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell.

At the opposite by "non integrative lentiviral vectors (or NILV)" is meant efficient gene delivery vectors that do not integrate the genome of a target cell through the action of the virus integrase.

One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors. A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art. Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracyclin, rifampicin or ampicillin resistance in *E. coli*. Preferably said vectors are expression vectors, wherein a sequence encoding a polypeptide of interest is placed under control of appropriate transcriptional and translational control elements to permit production or synthesis of said polypeptide. Therefore, said polynucleotide is comprised in an expression cassette. More particularly, the vector comprises a replication origin, a promoter operatively linked to said encoding polynucleotide, a ribosome binding site, a RNA-splicing site (when genomic DNA is used), a polyadenylation site and a transcription termination site. It also can comprise an enhancer or silencer elements. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-

D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

Inducible promoters may be induced by pathogens or stress, more preferably by stress like cold, heat, UV light, or high ionic concentrations (reviewed in Potenza C et al. 2004, In vitro Cell Dev Biol 40:1-22). Inducible promoter may be induced by chemicals (reviewed in (Moore, Samalova et al. 2006); (Padidam 2003); (Wang, Zhou et al. 2003); (Zuo and Chua 2000).

Delivery vectors and vectors can be associated or combined with any cellular permeabilization techniques such as sonoporation or electroporation or derivatives of these techniques.

By cell or cells is intended any prokaryotic or eukaryotic living cells, cell lines derived from these organisms for in vitro cultures, primary cells from animal or plant origin.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

In the frame of the present invention, "eukaryotic cells" refer to a fungal, plant or animal cell or a cell line derived from the organisms listed below and established for in vitro culture. More preferably, the fungus is of the genus *Aspergillus, Penicillium, Acremonium, Trichoderma, Chrysoporium, Mortierella, Kluyveromyces* or *Pichia*; More preferably, the fungus is of the species *Aspergillus niger, Aspergillus nidulans, Aspergillus oryzae, Aspergillus terreus, Penicillium chrysogenum, Penicillium citrinum, Acremonium Chrysogenum, Trichoderma reesei, Mortierella alpine, Chrysosporium lucknowense, Kluyveromyces lactis, Pichia pastoris* or *Pichia ciferrii*.

More preferably the plant is of the genus *Arabidospis, Nicotiana, Solanum, Iactuca, Brassica, Oryza, Asparagus, Pisum, Medicago, Zea, Hordeum, Secale, Triticum, Capsicum, Cucumis, Cucurbita, Citrullis, Citrus, Sorghum*; More preferably, the plant is of the species *Arabidospis thaliana, Nicotiana tabaccum, Solanum lycopersicum, Solanum tuberosum, Solanum melongena, Solanum esculentum, Lactuca saliva, Brassica napus, Brassica oleracea, Brassica rapa, Oryza glaberrima, Oryza sativa, Asparagus officinalis, Pisum sativum, Medicago sativa, Zea mays, Hordeum vulgare, Secale cereal, Triticum aestivum, Triticum durum, Capsicum sativus, Cucurbita pepo, Citrullus lanatus, Cucumis melo, Citrus aurantifolia, Citrus maxima, Citrus medica, Citrus reticulata*.

More preferably the animal cell is of the genus *Homo, Rattus, Mus, Sus, Bos, Danio, Canis, Felis, Equus, Salmo, Oncorhynchus, Gallus, Meleagris, Drosophila, Caenorhabditis*; more preferably, the animal cell is of the species *Homo sapiens, Rattus norvegicus, Mus musculus, Sus scrofa, Bos taurus, Danio rerio, Canis lupus, Felis catus, Equus caballus, Salmo salar, Oncorhynchus mykiss, Gallus gallus, Meleagris gallopavo, Drosophila melanogaster, Caenorhabditis elegans*.

In the present invention, the cell can be a plant cell, a mammalian cell, a fish cell, an insect cell or cell lines derived from these organisms for in vitro cultures or primary cells taken directly from living tissue and established for in vitro culture. As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

In the frame of the present invention, the expression "cleavage-induced mutagenesis", preferably Double-Strand Break (DSB)-induced mutagenesis refers to a mutagenesis event consecutive to an NHEJ event following an endonuclease-induced cleavage, leading to insertion/deletion at the cleavage site of an endonuclease.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a nucleic acid sequence (e.g. of a gene) on a chromosome. The term "locus" usually refers to the specific physical location of a protein or chimeric protein's nucleic acid target sequence on a chromosome. Such a locus can comprise a target sequence that is recognized and/or cleaved by a protein or a chimeric protein according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria or chloroplasts as non-limiting examples.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

By "chimeric protein" according to the present invention is meant any fusion protein comprising at least one RVD to bind a nucleic acid sequence and one additional protein domain to process a nucleic acid target sequence within or adjacent to said bound nucleic acid sequence.

By "additional protein domain" or "protein domain" is meant the nucleic acid target sequence processing part of said chimeric protein according to the present invention. Said protein domain can provide any catalytical activity as classified and named according to the reaction they catalyze [Enzyme Commission number (EC number) at http://www.chem.qmul.ac.uk/iubmb/enzyme/]. Said protein domain can be a catalytically active entity by itself. Said protein domain can be a protein subdomain that needs to interact with another protein subdomain to form a dimeric protein domain active entity.

By a "TALE-nuclease" (TALEN) is intended a fusion protein consisting of a DNA-binding domain derived from a Transcription Activator Like Effector (TALE) and one nuclease catalytic domain to cleave a nucleic acid target sequence. Said TALE-nuclease is a subclass of chimeric protein according to the present invention.

by "variant(s)", it is intended a RVD variant, a chimeric protein variant, a DNA binding variant, a TALE-nuclease variant, a polypeptide variant obtained by replacement of at least one residue in the amino acid sequence of the parent molecule.

by "functional mutant" is intended a catalytically active mutant of a protein or a protein domain; such mutant can have the same activity compared to its parent protein or protein domain or additional properties. This definition applies to chimeric proteins or protein domains that constitute chimeric proteins according to the present invention. Are also encompassed in the scope of this definition "derivatives" of these proteins or protein domains that comprise the entirety or part of these proteins or protein domains fused to other proteic or chemical parts such as tags, antibodies, polyethylene glycol as non-limiting examples.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

A first characterization of the activity, in yeast, of libraries having position 12 and/or 13 randomized (based on a HD scaffold, SEQ ID NO: 19) was performed. The randomization was performed on the RVD in position 1 and/or on the RVDs in position 1 and 2 according to the target.

Libraries on Position 12 and 13

Eight libraries (lib1 to 8) which contain only a subset of the possible 20 natural amino acids and one library (lib9) containing the 20 possible amino acids were first used. The randomization of positions 12 and 13 was performed using degenerated oligonucleotides (Table 1; SEQ ID NO: 26-39) and conventional Overlap Extension (OE) PCR techniques using a HD mono-RVD in a pAPG10 plasmid (SEQ ID NO: 40) as template.

TABLE 1

List of oligonucleotides (5'→3') used to introduce diversity in positions 12 and 13 in libraries of a HD bloc.

| Library | Oligo-nucleo-tides | Sequences 5'->3' | SEQ ID NO: | Diversity Mono-RVD | Di-RVD |
|---|---|---|---|---|---|
|  | A1 | cccagtcacgacgttgtaaaac | 26 |  |  |
| Lib 1 | B1 | gtctccagcgcctgcttgccgcccHNSaYgctggcgatggccacctgctc | 27 | 48 | 2304 |
| Lib 2 | B2 | gtctccagcgcctgcttgccgccaBNSaYgctggcgatggccacctgctc | 28 | 48 | 2304 |
| Lib 3 | B3 | gtctccagcgcctgcttgccgcccHNaSYgctggcgatggccacctgctc | 29 | 48 | 2304 |
| Lib 4 | B4 | gtctccagcgcctgcttgccgccHBNSaYgctggcgatggccacctgctc | 30 | 144 | 20736 |
| Lib 5 | B5 | gtctccagcgcctgcttgccgccGWDMHagctggcgatggccacctgctc | 31 | 36 | 1296 |

TABLE 1-continued

List of oligonucleotides (5'→3') used to introduce diversity
in positions 12 and 13 in libraries of a HD bloc.

| Library | Oligo-nucleotides | Sequences 5'->3' | SEQ ID NO: | Diversity Mono-RVD | Di-RVD |
|---|---|---|---|---|---|
| Lib 6 | B6 | gtctccagcgcctgcttgccgccMHaMHagctggcgatggccacctgctc | 32 | 36 | 1296 |
| Lib 7 | B7 | gtctccagcgcctgcttgccgccaSYcHNgctggcgatggccacctgctc | 33 | 48 | 2304 |
| Lib 8 | B8 | gtctccagcgcctgcttgccgccMTYcHNgctggcgatggccacctgctc | 34 | 48 | 2304 |
| | C1 | cacaggaaacagctatgaccatg | 35 | | |
| | D1 | ggcaagcaggcgctggagacgg | 36 | | |
| Lib 9 | B9 | gtctccagcgcctgcttgccgccMNNMNNgctggcgatggccacctgctc | 37 | 1024 | |
| | A2 | cccagtcacgacgttgtaaaac | 38 | | |
| | C2 | cccggtaccgcatctcgagg | 39 | | |

All DNA fragments used in the different steps were purified by gel extraction. In brief, for the smaller libraries (lib1-8) the 8 DNA fragment containing the randomized 6 base pairs are generated using oligonucleotides A1 (SEQ ID NO: 26) combined with B1-138 (SEQ ID NO: 27 to 34) and the complementary fragment was generated using oligonucleotides C1 (SEQ ID NO: 35) combined with D1 (SEQ ID NO: 36). The assembly PCRs were performed using oligonucleotides A1 and C1. To prepare the starting biotinylated RVD block library used for the array synthesis, the assembly PCR is amplified by PCR using primers A2 (SEQ ID NO: 38) and C2 (SEQ ID NO: 39). The PCR product is purified and digested with SfaNI. To prepare the RVD block library to be used in position 2, the assembly PCR is purified and digested with BbvI. The use of type IIS restriction enzyme allows creation of compatible overhang between blocks. For the fully randomized library, mono-RVDs were prepared as described for smaller libraries except using oligonucleotide A2 (SEQ ID NO: 38) with B9 (SEQ ID NO: 37) and C2 (SEQ ID NO: 39) instead of C1 (SEQ ID NO: 35) for the first PCR and the subsequent assembly PCR.

The final RVD arrays libraries containing 1 or 2 randomized blocks (SEQ ID NO: 41 to 58) were synthesized using a solid support method composed of consecutive restriction/ligation/washing steps as shown in FIG. 1. In brief the first library block was immobilized on a solid support through biotin/streptavidin interaction, the second library block is ligated to the first and after SfaNI digestion, the remaining of the array (i.e the RVD array out of RVD from library, SEQ ID NO: 59) pre-synthesized by the same method was ligated to the libraries. Due to the choice of the synthesis conditions, it is expected to recover up to 50% of mono-RVD libraries, the fraction of array not having a library is expected to be neglectable. The RVD arrays libraries were first cloned in a shuttle pAPG10 plasmid. The plasmid was transformed in *E. coli*, colonies representing between 5 and 50% of the total library diversity were scrapped from the petri dishes, and DNA recovered by standard miniprep techniques. The insert of interest is recovered by restriction (BbvI and SfaNI) followed gel extraction and cloning into a yeast expression plasmids.

Cloning of the RVD Array Collection in the TAL Backbone

The amino acid sequences of the N-terminal, C-terminal domains and RVDS were based on the AvrBs3 TAL (ref: GenBank: X16130.1, SEQ ID NO: 78). The TAL backbone used in these experiment (pCLS9944, SEQ ID NO: 60) was derived from the previously described pCLS7183 (SEQ ID NO: 61). This backbone, pCLS9944, contains an additional N-terminal NLS sequence followed by an HA tag compared to the original pCLS7183. The C-terminal and the N-terminal domains are separated by two BsmBI restriction sites. The RVD arrays libraries (SEQ ID NO: 41 to 58) were subcloned in the pCLS9944 using type IIs restriction enzymes BsmBI for the receiving plasmid and BbvI and SfaNI for the inserted RVD sequence, leading to the nine libraries. Colonies were scrapped and DNA recovered by standard miniprep techniques.

TALE-Nuclease Activities in Yeast

All the libraries (558 clones after yeast transformation) were screened on a target set containing the 16 possible bases in position 1/2, allowing using the same target set for libraries having 1 or 2 RVDs randomized. All the yeast target reporter plasmids containing the TALE-Nuclease DNA target collection sequences were constructed as previously described (International PCT Applications WO 2004/067736 and in (Epinat, Arnould et al. 2003; Chames, Epinat et al. 2005; Arnould, Chames et al. 2006; Smith, Grizot et al. 2006). The collections of TALE-Nuclease were tested at 37° C. and 30° C. in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) as pseudo-palindromic sequences (two identical recognition sequences are placed facing each other on both DNA strands) on their target collections (SEQ ID NO: 62 to 77, Table 2).

TABLE 2

Target collections for libraries screening.

| Name | Sequence | SEQ ID NO: |
|---|---|---|
| AAG_RAGT2L10 | TAAGCACTTATatgtgtgtaacaggt ATAAGTGCTTA | 62 |
| ACG_RAGT2L10 | TACGCACTTATatgtgtgtaacaggt ATAAGTGCGTA | 63 |

TABLE 2-continued

Target collections for libraries screening.

| Name | Sequence | SEQ ID NO: |
|---|---|---|
| AGG_RAGT2L10 | TAGGCACTTATatgtgtgtaacaggtATAAGTGCCTA | 64 |
| ATG_RAGT2L10 | TATGCACTTATatgtgtgtaacaggtATAAGTGCATA | 65 |
| CAG_RAGT2L10 | TCAGCACTTATatgtgtgtaacaggtATAAGTGCTGA | 66 |
| CCG_RAGT2L10 | TCCGCACTTATatgtgtgtaacaggtATAAGTGCGGA | 67 |
| CGG_RAGT2L10 | TCGGCACTTATatgtgtgtaacaggtATAAGTGCCGA | 68 |
| CTG_RAGT2L10 | TCTGCACTTATatgtgtgtaacaggtATAAGTGCAGA | 69 |
| GAG_RAGT2L10 | TGAGCACTTATatgtgtgtaacaggtATAAGTGCTCA | 70 |
| GCG_RAGT2L10 | TGCGCACTTATatgtgtgtaacaggtATAAGTGCGCA | 71 |
| GGG_RAGT2L10 | TGGGCACTTATatgtgtgtaacaggtATAAGTGCCCA | 72 |
| GTG_RAGT2L10 | TGTGCACTTATatgtgtgtaacaggtATAAGTGCACA | 73 |
| TAG_RAGT2L10 | TTAGCACTTATatgtgtgtaacaggtATAAGTGCTAA | 74 |
| TCG_RAGT2L10 | TTCGCACTTATatgtgtgtaacaggtATAAGTGCGAA | 75 |
| TGG_RAGT2L10 | TTGGCACTTATatgtgtgtaacaggtATAAGTGCCAA | 76 |
| TTG_RAGT2L10 | TTTGCACTTATatgtgtgtaacaggtATAAGTGCAAA | 77 |

TALE-Nuclease cleavage activity levels of individual clones of the library on the complete collection of targets in yeast were recorded. Plasmid DNA of clones having activity on at least one target was recovered using standard yeast biology techniques, transformed in E. coli and plasmid DNA from individual colonies were recovered by standard molecular biology techniques. The plasmid DNA were sequenced and retransformed in yeast for a secondary screen. Table 3 represents the mean activity (screen 1 and 2) of three clones in which RVD 1 was randomized (SEQ ID NO: 23 to 25) recovered from a subset of the libraries.

TABLE 3

Mean activities of three clones with one RVD randomized on a serie of targets (SEQ ID NO: 62-77) in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 30° C. – indicates no detectable activity, + indicates low activity, ++ medium activity and +++ high activity.

| | | Targeted base | | | |
|---|---|---|---|---|---|
| | | A | C | G | T |
| Varia-ble | Classical | HD (SEQ ID NO: 19) | ++ | ++ | + | +++ |
| | | NN (SEQ ID NO: 20) | +++ | +/- | +++ | - |

TABLE 3-continued

Mean activities of three clones with one RVD randomized on a serie of targets (SEQ ID NO: 62-77) in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 30° C. – indicates no detectable activity, + indicates low activity, ++ medium activity and +++ high activity.

| | | Targeted base | | | |
|---|---|---|---|---|---|
| | | A | C | G | T |
| di-residue | | NG (SEQ ID NO: 21) | ++ | +++ | +/- | - |
| | | NI (SEQ ID NO: 22) | +++ | +/- | + | - |
| | New | TL (SEQ ID NO: 23) | +++ | - | - | - |
| | | VT (SEQ ID NO: 24) | +++ | +/- | +++ | - |
| | | SW (SEQ ID NO: 25) | +/- | - | - | - |

Example 2

To design new RVD/target pairs (in the context of a TALE-nuclease) an extensive characterization of the activity in yeast of libraries having position 12 and/or 13 randomized was performed. The randomization was performed in NNK libraries on positions 12 and 13 of a repeat unit inserted at position 1 to 4 of the array of 9.5 repeat units.

The randomization of positions 12 and 13 was performed using degenerated oligonucleotides (Table 4, SEQ ID NO: 79-84) and conventional Overlap Extension (OE) PCR techniques using a NG mono-repeat unit (SEQ ID NO: 85) in a pAPG10 plasmid (SEQ ID NO: 86) as template. All DNA fragments used in the different steps were purified by appropriate techniques. In brief, the DNA fragment containing the randomized 6 base pairs are generated using oligonucleotide E1 (SEQ ID NO: 79) combined with E2 (SEQ ID NO: 80) leading to FRAG1 and the complementary fragment was generated using oligonucleotides F1 (SEQ ID NO: 81) combined with F2 (SEQ ID NO: 82) leading to FRAG2. The assembly PCR of FRAG1 and FRAG2 was performed using oligonucleotides G1 (SEQ ID NO: 83) and G2 (SEQ ID NO: 84) to allow biotinylation of the fragment. The PCR product are further purified and digested with SfaNI.

TABLE 4

List of oligonucleotides (5'→3') used to introduce diversity in position 12 and 13 of a NG bloc.

| Oligonucleotide Names | Sequences | SEQ ID NO: |
|---|---|---|
| Oligo E1 | cccagtcacgacgttgtaaaac | 79 |
| Oligo E2 | gtctccagcgcctgcttgccgccMNNMNNgctggcgatggccaccacctgctc | 80 |
| Oligo F1 | ggcaagcaggcgctggagacgg | 81 |
| Oligo F2 | cacaggaaacagctatgaccatg | 82 |
| Oligo G1 | Biotin-cccagtcacgacgttgtaaaac | 83 |
| Oligo G2 | cccggtaccgcatctcgagg | 84 |

Library a in Position 1 of the Array

For this collection in position 1 of the TALE array, the desired building block coding for TALE array A2-A10 (SEQ ID NO: 87) was pre-prepared (BbvI digested) and coupled (ligated) to the immobilized bloc (randomized in positions 12 and 13) via a solid support technology (FIG. 2). The final product was recovered using enzymatic restriction (SfaNI and BbvI digestions) and cloned in a yeast pCLS9944 expression plasmid (SEQ ID NO: 60). After transformation in *E. coli*, 1200 colonies were individually picked, grown overnight and plasmid DNA extracted using standard procedures.

Libraries B, C and D in Position 2, 3 and 4 of the Array

For these libraries in position 2, 3 and 4 of the TALE array, the desired building blocks coding for RVD array B03-B10 (SEQ ID NO: 88) for library B, C04-C10 (SEQ ID NO: 89) for library C and D05-D10 (SEQ ID NO: 90) for library D were pre-prepared and coupled to the randomized bloc via a solid support technology and steps of enzymatic restrictions and digestions. The coupled intermediate products were then subcloned in the shuttle pAGG10 plasmid. Colonies (at least 4 time the diversity of the libraries) were scraped from the agarose plates, plasmid DNA were extracted using standard techniques and the intermediate array constructs containing the randomized bloc in position 1 were recovered using enzymatic restriction (BbvI and SfiI). These intermediate array constructs containing the randomized bloc in position 1 were coupled (ligated) to immobilized blocs coding for, B01 (SEQ ID NO: 91) for library B, C01-C002 (SEQ ID NO: 92) for library C and D01-D03 (SEQ ID NO: 93) for library D, via a solid support technology (FIG. 2). The final products were recovered using enzymatic restriction (SfaNI and BbvI digestions) and cloned in a yeast expression plasmid pCLS9944 (SEQ ID NO: 60). After transformation in *E. coli*, 1200 colonies were individually picked, grown overnight and plasmid DNA extracted using standard procedures.

TALE-Nuclease Library Activities in Yeast

DNA plasmids coding for all members of the libraries, were individually transformed in yeast cells, leading to 1144, 1149, 1148 and 1150 transformants for the library A, B, C and D respectively.

All the yeast target reporter plasmids containing the TALE-Nuclease DNA target collection sequences were constructed as previously described (International PCT Applications WO 2004/067736 and in (Epinat, Arnould et al. 2003; Chames, Epinat et al. 2005; Arnould, Chames et al. 2006; Smith, Grizot et al. 2006). The libraries of TALE-Nuclease were tested at 37° C. and 30° C. in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) as pseudo-palindromic sequences (two identical recognition sequences are placed facing each other on both DNA strands) on their respective targets (containing A, C, G or T at the position of the library bloc, Table 5, SEQ ID NO: 94 to SEQ ID NO: 109).

TABLE 5

| Target Names | Target Sequences | SEQ ID NO: |
|---|---|---|
| Target position 1 A | TAGTTACTTATatgtgtgtaacaggt ATAAGTAACTA | 94 |
| target position 1 C | TCGTTACTTATatgtgtgtaacaggt ATAAGTAACGA | 95 |
| target position 1 G | TGGTTACTTATatgtgtgtaacaggt ATAAGTAACCA | 96 |
| target position 1 T | TTGTTACTTATatgtgtgtaacaggt ATAAGTAACAA | 97 |
| target position 2 A | TTAGCACTTATatgtgtgtaacaggt ATAAGTGCTAA | 98 |
| target position 2 C | TTCGCACTTATatgtgtgtaacaggt ATAAGTGCGAA | 99 |
| target position 2 G | TTGGCACTTATatgtgtgtaacaggt ATAAGTGCCAA | 100 |
| target position 2 T | TTTGCACTTATatgtgtgtaacaggt ATAAGTGCAAA | 101 |
| target position 3 A | TGGATACTTATatgtgtgtaacaggt ATAAGTATCCA | 102 |
| target position 3 C | TGGCTACTTATatgtgtgtaacaggt ATAAGTAGCCA | 103 |
| target position 3 G | TGGGTACTTATatgtgtgtaacaggt ATAAGTACCCA | 104 |
| target position 3 T | TGGTTACTTATatgtgtgtaacaggt ATAAGTAACCA | 105 |
| target position 4 A | TGGTAACTTATatgtgtgtaacaggt ATAAGTTACCA | 106 |
| target position 4 C | TGGTCACTTATatgtgtgtaacaggt ATAAGTGACCA | 107 |

TABLE 5-continued

| Target Names | Target Sequences | SEQ ID NO: |
|---|---|---|
| target position 4 G | TGGTGACTTATatgtgtgtaacaggt ATAAGTCACCA | 108 |
| target position 4 T | TGGTTACTTATatgtgtgtaacaggt ATAAGTAACCA | 109 |

List of pseudo-palindromic sequences targets (two identical recognition sequences are placed facing each other on both DNA strands) in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 30° C., used for activity screens in yeast of libraries A, B, C and D.

TALE-Nuclease cleavage activities were recorded for all members of the libraries and are summarized in FIGS. 3, 4, 5 and 6 for the libraries A, B, C and D respectively. DNA of 101, 105, 136 and 128 (for the library A, B, C and D respectively) clones was sequenced.

Insertion of Non-Natural RVDs in 15.5 Repeats Arrays and Activities in Yeast

DNA coding for arrays containing non-natural RVDs in position 7 and 11 of the arrays was synthesized and subcloned in a pAPG10 plasmid (GeneCust) (SEQ ID NO: 86) leading to array pCLS19101 (NM in position 7 and LP in position 11) (SEQ ID NO: 110) and array pCLS19102 (SD in position 7 and VG in position 11) (SEQ ID NO: 111). The repeats containing arrays were then subcloned in a yeast expression plasmid pCLS9944 (SEQ ID NO: 60) using BsmBI restriction enzyme and standard molecular biology procedures leading to respectively half-TALE-Nuclease pCLS20349 (SEQ ID NO: 112) and pCLS20350 (SEQ ID NO: 113). The pendant of these two half-TALE-Nuclease containing only the canonical 4 RVDs (NI, HD, NG and NN) as well as the second half-TALE-Nuclease allowing the formation of an heterodimeric TALE-Nuclease were synthesized using solid support methods and subcloned in a yeast expression plasmid pCLS9944 (SEQ ID NO: 60) leading to respectively pCLS20735 (SEQ ID NO: 114) and pCLS20736 (SEQ ID NO: 115).

All the yeast target reporter plasmids were constructed as previously described (International PCT Applications WO 2004/067736 and in (Epinat, Arnould et al. 2003; Chames, Epinat et al. 2005; Arnould, Chames et al. 2006; Smith, Grizot et al. 2006). The TALE-Nucleases were tested at 37° C. in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) as heterodimeric sequences (two different recognition sequences are placed facing each other on both DNA strands) on 2 targets (A and B) varying at bases 7 and 11 (respective to the $T_0$) (Table 6, SEQ ID NO: 116 to SEQ ID NO: 117).

TABLE 6

| Target Names | Target sequences | SEQ ID NO: |
|---|---|---|
| Target A | TCTGACACAACTGTGTTcactagcaacctcaa ACAGACACCATGGTGCA | 116 |
| Target B | TCTGACATAACAGTGTTcactagcaacctcaa ACAGACACCATGGTGCA | 117 |

List of heterodimeric sequences targets A and B varying at bases 7 and 11 (two different recognition sequences are placed facing each other on both DNA strands) in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 37° C., used for activity screens in yeast of NM/LP and SD/VG containing half-TALE-Nuclease TALE-Nuclease cleavage activities were recorded for all three pairs pCLS20349/pCLS20736; pCLS20350/pCLS20736 and pCLS20735/pCLS20736 (Table 7). These results confirm that the news RVDs characterized in the present invention have a higher specificity than RVDs previously described (WO2011/146121).

TABLE 7

Activities of the three TALE-Nuclease pairs on heterodimeric sequence target A and B (two identical recognition sequences are placed facing each other on both DNA strands) in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 30° C. ++ indicates medium activity and +++ high activity.

|  | Target A | Target B |
|---|---|---|
| pCLS20349/pCLS20736 | +++ | ++ |
| pCLS20350/pCLS20736 | +++ | +++ |
| pCLS20735/pCLS20736 | +++ | +++ |

LIST OF CITED REFERENCES

Arnould, S., P. Chames, et al. (2006). "Engineering of large numbers of highly specific homing endonucleases that induce recombination on novel DNA targets." *J Mol Biol* 355(3): 443-58.

Boch, J., H. Scholze, et al. (2009). "Breaking the code of DNA binding specificity of TAL-type III effectors." *Science* 326(5959): 1509-12.

Bogdanove, A. J., S. Schornack, et al. (2010). "TAL effectors: finding plant genes for disease and defense." *Curr Opin Plant Biol* 13(4): 394-401.

Cermak, T., E. L. Doyle, et al. (2011). "Efficient design and assembly of custom TALEN and other TAL effector-based constructs for DNA targeting." *Nucleic Acids Res* 39(12): e82.

Chames, P., J. C. Epinat, et al. (2005). "In vivo selection of engineered homing endonucleases using double-strand break induced homologous recombination." *Nucleic Acids Res* 33(20): e178.

Christian, M., T. Cermak, et al. (2010). "Targeting DNA double-strand breaks with TAL effector nucleases." *Genetics* 186(2): 757-61.

Dayhoff, M. O., Schwartz, R. and Orcutt, B. C. (1978). "A model of Evolutionary Change in Proteins". *Atlas of protein sequence and structure* (volume 5, supplement 3 ed.). Nat. Biomed. Res. Found. pp. 345-358

Deng, D., C. Yan, et al. (2012). "Structural basis for sequence-specific recognition of DNA by TAL effectors." *Science* 335(6069): 720-3.

Epinat, J. C., S. Arnould, et al. (2003). "A novel engineered meganuclease induces homologous recombination in yeast and mammalian cells." *Nucleic Acids Res* 31(11): 2952-62.

Geissler, R., H. Scholze, et al. (2011). "Transcriptional activators of human genes with programmable DNA-specificity." *PLoS One* 6(5): e19509.

Henikoff, S, and J. G. Henikoff (1992). "Amino acid substitution matrices from protein blocks." *Proc Natl Acad Sci USA* 89(22): 10915-9.

Huang, P., A. Xiao, et al. (2011). "Heritable gene targeting in zebrafish using customized TALENs." *Nat Biotechnol* 29(8): 699-700.

Li, L., M. J. Piatek, et al. (2012). "Rapid and highly efficient construction of TALE-based transcriptional regulators and nucleases for genome modification." *Plant Mol Biol* 78(4-5): 407-16.

Li, T., S. Huang, et al. (2011). "TAL nucleases (TALNs): hybrid proteins composed of TAL effectors and FokI DNA-cleavage domain." *Nucleic Acids Res* 39(1): 359-72.

Mahfouz, M. M., L. Li, et al. (2012). "Targeted transcriptional repression using a chimeric TALE-SRDX repressor protein." *Plant Mol Biol* 78(3): 311-21.

Mahfouz, M. M., L. Li, et al. (2011). "De novo-engineered transcription activator-like effector (TALE) hybrid nuclease with novel DNA binding specificity creates double-strand breaks." *Proc Natl Acad Sci USA* 108(6): 2623-8.

Mak, A. N., P. Bradley, et al. (2012). "The crystal structure of TAL effector PthXo1 bound to its DNA target." *Science* 335(6069): 716-9.

Miller, J. C., S. Tan, et al. (2011). "A TALE nuclease architecture for efficient genome editing." *Nat Biotechnol* 29(2): 143-8.

Morbitzer, R., J. Elsaesser, et al. (2011). "Assembly of custom TALE-type DNA binding domains by modular cloning." *Nucleic Acids Res* 39(13): 5790-9.

Moscou, M. J. and A. J. Bogdanove (2009). "A simple cipher governs DNA recognition by TAL effectors." *Science* 326(5959): 1501.

Murakami, M. T. et al. The repeat domain of the type Ill effector protein PthA shows a TPR-like structure and undergoes conformational changes upon DNA interaction. *Proteins* 78, 3386-3395 (2010)

Mussolino, C., R. Morbitzer, et al. (2011). "A novel TALE nuclease scaffold enables high genome editing activity in combination with low toxicity." *Nucleic Acids Res* 39(21): 9283-93.

Sander, J. D., L. Cade, et al. (2011). "Targeted gene disruption in somatic zebrafish cells using engineered TAL-ENs." *Nat Biotechnol* 29(8): 697-8.

Smith, J., S. Grizot, et al. (2006). "A combinatorial approach to create artificial homing endonucleases cleaving chosen sequences." *Nucleic Acids Res.*

Tesson, L., C. Usal, et al. (2011). "Knockout rats generated by embryo microinjection of TALENs." *Nat Biotechnol* 29(8): 695-6.

Weber, E., R. Gruetzner, et al. (2011). "Assembly of designer TAL effectors by Golden Gate cloning." *PLoS One* 6(5): e19722.

Yakubovskaya, E., E. Mejia, et al. (2010). "Helix unwinding and base flipping enable human MTERF1 to terminate mitochondrial transcription." *Cell* 141(6): 982-93.

Zhang, F., L. Cong, et al. (2011). "Efficient construction of sequence-specific TAL effectors for modulating mammalian transcription." *Nat Biotechnol* 29(2): 149-53.

---

The invention claimed is:

1. A method for modifying the genetic material of a cell comprising:
   (a) selecting a nucleic acid target sequence present on a chromosome of a mammalian cell;
   (b) engineering a protein comprising at least:
      (i) one Transcription Activator-Like Effector (TALE) domain wherein said TALE domain comprises a plurality of TALE repeat sequences comprising each one a Repeat Variable Diresidue region (RVD) which is responsible for the binding to one specific nucleotide in the nucleic acid target sequence present on a chromosome of the mammalian cell, wherein one or more RVD is selected from the group consisting of:
      PI, DL, FL, GL, IL, KL, LL, YL, MM, WY, PV, SW, XF for recognizing A, wherein X represents one amino acid residue selected from the group consisting of A, G, V, L, I, M, S, T, C, P, D, E, F, Y, W, Q, N, and K;
      RE for recognizing C;
      ER, FR, GR, LR, QR, VR for recognizing G; and
      (ii) an endonuclease domain to cleave genetic material within the nucleic acid target sequence;
   (c) contacting said engineered protein with said nucleic acid target sequence in the mammalian cell such that the engineered protein binds to the nucleic acid target sequence and cleaves the chromosome within the nucleic acid target sequence to create a double strand break,
      wherein the double strand break is repaired by the cell through non-homologous end joining (NHEJ) resulting in a genetic modification in the chromosome.

2. A method for inducing homologous gene targeting in a mammalian cell comprising:
   (a) providing a mammalian cell comprising a nucleic acid target sequence present on a chromosome;
   (b) engineering a chimeric protein comprising at least:
      (i) one Transcription Activator-Like Effector (TALE) domain wherein said TALE domain comprises a plurality of TALE repeat sequences comprising each one a Repeat Variable Diresidue region (RVD) which is responsible for the binding to one specific nucleotide in the nucleic acid target sequence present on a chromosome of the mammalian cell, wherein one or more RVD is selected from the group consisting of:
      PI, DL, FL, GL, IL, KL, LL, YL, MM, WY, PV, SW, XF for recognizing A, wherein X represents one amino acid residue selected from the group consisting of A, G, V, L, I, M, S, T, C, P, D, E, F, Y, W, Q, N, and K;
      RE for recognizing C;
      ER, FR, GR, LR, QR, VR for recognizing G; and
      (ii) an endonuclease domain to cleave genetic material within the nucleic acid target sequence; and
   (c) introducing said chimeric protein into said mammalian cell such that the engineered protein binds to the nucleic acid target sequence and cleaves the chromosome within the nucleic acid target sequence to create a double strand break,
   (d) introducing into the cell an exogenous nucleic acid comprising a sequence homologous to at least a portion of the nucleic acid target sequence,
      wherein homologous recombination occurs between said exogenous nucleic acid and the nucleic acid target sequence processes genetic material within or adjacent to the specific nucleic acid target sequence.

3. A method for generating an animal comprising:
   (a) providing a cell comprising a nucleic acid target sequence into which it is desired to introduce a genetic modification;
   (b) modifying the genetic material of a cell according to the method of claim 1;
   (c) generating an animal from the cell or progeny thereof, in which a genetic modification has occurred.

4. The method according to claim 2, wherein the cell is a human cell.

5. The method of claim 2, wherein one or more RVD is selected from the group consisting of:
PI, DL, FL, GL, IL, KL, LL, YL, MM, WY, PV, SW, XF for recognizing A.

6. The method of claim 2, wherein one or more RVD is selected from the group consisting of:
RE for recognizing C.

7. The method of claim 2, wherein one or more RVD is selected from the group consisting of:
ER, FR, GR, LR, QR, VR for recognizing G.

8. The method of claim 1, wherein one or more RVD is selected from the group consisting of:
PI, DL FL, GL, IL, KL, LL, YL, MM, WY, PV, SW, XF for recognizing A.

9. The method of claim 1, wherein one or more RVD is selected from the group consisting of:

RE for recognizing C.

10. The method of claim 1, wherein one or more RVD is selected from the group consisting of:

ER, FR, GR, LR, QR, VR for recognizing G.

11. The method of claim 1, wherein the genetic modification is a deletion.

12. The method of claim 1, wherein the genetic modification is an insertion.

13. The method of claim 1, wherein the genetic modification is a combination of both a deletion and an insertion.

* * * * *

SEQUENCE LISTING

<160> NUMBER OF SEQ ID NOS: 117

<210> SEQ ID NO 1
<211> LENGTH: 28
<212> TYPE: PRT
<213> ORGANISM: artificial sequence
<220> FEATURE:
<223> OTHER INFORMATION: Repeat sequence with loop modification

<400> SEQUENCE: 1

Leu Thr Pro Glu Gln Val Val Ala Ile Ala Ser Asn Gly Gly Gly Lys
1               5                   10                  15

Gln Ala Leu Glu Pro Val Leu Cys Gln Ala His Gly
            20                  25

<210> SEQ ID NO 2
<211> LENGTH: 27
<212> TYPE: PRT
<213> ORGANISM: artificial sequence
<220> FEATURE:
<223> OTHER INFORMATION: Repeat sequence with loop modification

<400> SEQUENCE: 2

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro
            20                  25

<210> SEQ ID NO 3
<211> LENGTH: 26
<212> TYPE: PRT
<213> ORGANISM: artificial sequence
<220> FEATURE:
<223> OTHER INFORMATION: Repeat sequence with loop modification

<400> SEQUENCE: 3

Leu Thr Pro Glu Gln Val Val Ala Ile Ala Ser Asn Gly Gly Gly Lys
1               5                   10                  15

Gln Ala Leu Glu Gly Ser Gly Ser Gly Ser
            20                  25

<210> SEQ ID NO 4
<211> LENGTH: 34
<212> TYPE: PRT
<213> ORGANISM: artificial sequence
<220> FEATURE:
<223> OTHER INFORMATION: Repeat sequence with loop modification

<400> SEQUENCE: 4

Leu Thr Pro Glu Gln Val Val Ala Ile Ala Ser Asn Gly Gly Gly Lys
1               5                   10                  15

Gln Ala Leu Glu Thr Val Gln Gly Ser Gly Ser Gly Ser Gly Ser Gly
            20                  25                  30

Gly Ser

<210> SEQ ID NO 5
<211> LENGTH: 34
<212> TYPE: PRT
<213> ORGANISM: artificial sequence
<220> FEATURE:
<223> OTHER INFORMATION: Repeat sequence with loop modification

<400> SEQUENCE: 5

Leu Thr Pro Glu Gln Val Val Ala Ile Ala Ser Asn Gly Gly Gly Lys
1               5                   10                  15

Gln Ala Leu Glu Thr Val Gln Gly Gly Ser Gly Gly Ser Lys Gly
            20                  25                  30

Gly Ser

<210> SEQ ID NO 6
<211> LENGTH: 34
<212> TYPE: PRT
<213> ORGANISM: artificial sequence
<220> FEATURE:
<223> OTHER INFORMATION: Repeat sequence from BLOSUM80 matrix

<400> SEQUENCE: 6

Leu Thr Pro Asp Glu Ile Ile Ser Met Ser Ser Asn Gly Gly Gly Arg
1               5                   10                  15

Glu Ser Met Asp Ser Ile His Lys Ile Val Pro Leu Val Cys His Val
            20                  25                  30

Tyr Gly

<210> SEQ ID NO 7
<211> LENGTH: 34

```
<212> TYPE: PRT
<213> ORGANISM: artificial sequence
<220> FEATURE:
<223> OTHER INFORMATION: Repeat sequence from BLOSUM80 matrix

<400> SEQUENCE: 7

Leu Thr Pro Asp Glu Leu Leu Thr Met Gln Ser Asn Gly Gly Gly Arg
1               5                   10                  15

Asn Val Met Glu Ser Ile Gln Lys Ala Leu Pro Ile Ala Ser Asn Val
            20                  25                  30

Gln Gly

<210> SEQ ID NO 8
<211> LENGTH: 34
<212> TYPE: PRT
<213> ORGANISM: artificial sequence
<220> FEATURE:
<223> OTHER INFORMATION: Repeat sequence from BLOSUM80 matrix

<400> SEQUENCE: 8

Leu Thr Pro Asp Glu Val Val Ala Ile Ala Ser Asn Gly Gly Gly Lys
1               5                   10                  15

Gln Ala Leu Glu Ser Ile His Lys Ile Val Pro Leu Val Cys His Val
            20                  25                  30

Tyr Gly

<210> SEQ ID NO 9
<211> LENGTH: 340
<212> TYPE: PRT
<213> ORGANISM: artificial sequence
<220> FEATURE:
<223> OTHER INFORMATION: Repeat sequence with loop modification

<400> SEQUENCE: 9

Leu Thr Pro Glu Gln Val Val Ala Ile Ala Ser Asn Asn Gly Gly Lys
1               5                   10                  15

Gln Ala Leu Glu Thr Pro Gly Ser Gly Ser Gly Ser Gly Ser Gly Ser
            20                  25                  30

Gly Ser Leu Thr Pro Glu Gln Val Val Ala Ile Ala Ser Asn Asn Gly
            35                  40                  45

Gly Lys Gln Ala Leu Glu Thr Pro Gly Ser Gly Ser Gly Ser Gly Ser
    50                  55                  60

Gly Ser Gly Ser Leu Thr Pro Glu Gln Val Val Ala Ile Ala Ser Asn
65                  70                  75                  80

Gly Gly Gly Lys Gln Ala Leu Glu Thr Pro Gly Ser Gly Ser Gly Ser
                85                  90                  95

Gly Ser Gly Ser Gly Ser Leu Thr Pro Glu Gln Val Val Ala Ile Ala
            100                 105                 110

Ser Asn Gly Gly Gly Lys Gln Ala Leu Glu Thr Pro Gly Ser Gly Ser
        115                 120                 125

Gly Ser Gly Ser Gly Ser Gly Ser Leu Thr Pro Glu Gln Val Val Ala
    130                 135                 140

Ile Ala Ser Asn Ile Gly Gly Lys Gln Ala Leu Glu Thr Pro Gly Ser
145                 150                 155                 160

Gly Ser Gly Ser Gly Ser Gly Ser Gly Ser Leu Thr Pro Glu Gln Val
                165                 170                 175

Val Ala Ile Ala Ser His Asp Gly Gly Lys Gln Ala Leu Glu Thr Pro
            180                 185                 190
```

```
Gly Ser Gly Ser Gly Ser Gly Ser Gly Ser Leu Thr Pro Glu
            195                 200                 205

Gln Val Val Ala Ile Ala Ser Asn Gly Gly Lys Gln Ala Leu Glu
210                 215                 220

Thr Pro Gly Ser Gly Ser Gly Ser Gly Ser Gly Ser Leu Thr
225             230                 235                 240

Pro Glu Gln Val Val Ala Ile Ala Ser Asn Gly Gly Lys Gln Ala
                245                 250                 255

Leu Glu Thr Pro Gly Ser Gly Ser Gly Ser Gly Ser Gly Ser
            260                 265                 270

Leu Thr Pro Glu Gln Val Val Ala Ile Ala Ser Asn Ile Gly Gly Lys
        275                 280                 285

Gln Ala Leu Glu Thr Pro Gly Ser Gly Ser Gly Ser Gly Ser
        290                 295                 300

Gly Ser Leu Thr Pro Glu Gln Val Val Ala Ile Ala Ser Asn Gly Gly
305                 310                 315                 320

Gly Lys Gln Ala Leu Glu Thr Pro Gly Ser Gly Ser Gly Ser
            325                 330                 335

Gly Ser Gly Ser
            340

<210> SEQ ID NO 10
<211> LENGTH: 340
<212> TYPE: PRT
<213> ORGANISM: artificial sequence
<220> FEATURE:
<223> OTHER INFORMATION: Repeat sequence with loop modification

<400> SEQUENCE: 10

Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Ala Ile Ala Ser Asn Asn Gly
        35                  40                  45

Gly Lys Gln Ala Leu Glu Thr Pro Gly Ser Gly Ser Gly Ser Gly Ser
    50                  55                  60

Gly Ser Gly Ser Leu Thr Pro Glu Gln Val Val Ala Ile Ala Ser Asn
65                  70                  75                  80

Gly Gly Gly Lys Gln Ala Leu Glu Thr Pro Gly Ser Gly Ser Gly Ser
                85                  90                  95

Gly Ser Gly Ser Gly Ser Leu Thr Pro Glu Gln Val Val Ala Ile Ala
            100                 105                 110

Ser Asn Gly Gly Gly Lys Gln Ala Leu Glu Thr Pro Gly Ser Gly Ser
        115                 120                 125

Gly Ser Gly Ser Gly Ser Gly Ser Leu Thr Pro Glu Gln Val Val Ala
    130                 135                 140

Ile Ala Ser Asn Ile Gly Gly Lys Gln Ala Leu Glu Thr Pro Gly Ser
145                 150                 155                 160

Gly Ser Gly Ser Gly Ser Gly Ser Gly Ser Leu Thr Pro Glu Gln Val
                165                 170                 175

Val Ala Ile Ala Ser His Asp Gly Gly Lys Gln Ala Leu Glu Thr Pro
            180                 185                 190

Gly Ser Gly Ser Gly Ser Gly Ser Gly Ser Gly Ser Leu Thr Pro Glu
        195                 200                 205
```

```
Gln Val Val Ala Ile Ala Ser Asn Gly Gly Lys Gln Ala Leu Glu
    210                 215                 220

Thr Pro Gly Ser Gly Ser Gly Ser Gly Ser Gly Ser Leu Thr
225                 230                 235                 240

Pro Glu Gln Val Val Ala Ile Ala Ser Asn Gly Gly Lys Gln Ala
                245                 250                 255

Leu Glu Thr Pro Gly Ser Gly Ser Gly Ser Gly Ser Gly Ser
            260                 265                 270

Leu Thr Pro Glu Gln Val Val Ala Ile Ala Ser Asn Ile Gly Gly Lys
        275                 280                 285

Gln Ala Leu Glu Thr Pro Gly Ser Gly Ser Gly Ser Gly Ser
    290                 295                 300

Gly Ser Leu Thr Pro Glu Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly
            340

<210> SEQ ID NO 11
<211> LENGTH: 280
<212> TYPE: PRT
<213> ORGANISM: artificial sequence
<220> FEATURE:
<223> OTHER INFORMATION: Repeat sequence with loop modification

<400> SEQUENCE: 11

Leu Thr Pro Glu Gln Val Val Ala Ile Ala Ser Asn Asn Gly Gly Lys
1               5                   10                  15

Gln Ala Leu Glu Thr Pro Gly Ser Gly Ser Gly Ser Leu Thr Pro Glu
            20                  25                  30

Gln Val Val Ala Ile Ala Ser Asn Asn Gly Gly Lys Gln Ala Leu Glu
        35                  40                  45

Thr Pro Gly Ser Gly Ser Gly Ser Leu Thr Pro Glu Gln Val Val Ala
    50                  55                  60

Ile Ala Ser Asn Gly Gly Gly Lys Gln Ala Leu Glu Thr Pro Gly Ser
65                  70                  75                  80

Gly Ser Gly Ser Leu Thr Pro Glu Gln Val Val Ala Ile Ala Ser Asn
                85                  90                  95

Gly Gly Gly Lys Gln Ala Leu Glu Thr Pro Gly Ser Gly Ser Gly Ser
            100                 105                 110

Leu Thr Pro Glu Gln Val Val Ala Ile Ala Ser Asn Ile Gly Gly Lys
        115                 120                 125

Gln Ala Leu Glu Thr Pro Gly Ser Gly Ser Gly Ser Leu Thr Pro Glu
    130                 135                 140

Gln Val Val Ala Ile Ala Ser His Asp Gly Gly Lys Gln Ala Leu Glu
145                 150                 155                 160

Thr Pro Gly Ser Gly Ser Gly Ser Leu Thr Pro Glu Gln Val Val Ala
                165                 170                 175

Ile Ala Ser Asn Gly Gly Gly Lys Gln Ala Leu Glu Thr Pro Gly Ser
            180                 185                 190

Gly Ser Gly Ser Leu Thr Pro Glu Gln Val Val Ala Ile Ala Ser Asn
        195                 200                 205

Gly Gly Gly Lys Gln Ala Leu Glu Thr Pro Gly Ser Gly Ser Gly Ser
    210                 215                 220
```

```
Leu Thr Pro Glu Gln Val Val Ala Ile Ala Ser Asn Ile Gly Gly Lys
225                 230                 235                 240

Gln Ala Leu Glu Thr Pro Gly Ser Gly Ser Gly Ser Leu Thr Pro Glu
                245                 250                 255

Gln Val Val Ala Ile Ala Ser Asn Gly Gly Gly Lys Gln Ala Leu Glu
            260                 265                 270

Thr Pro Gly Ser Gly Ser Gly Ser
        275                 280

<210> SEQ ID NO 12
<211> LENGTH: 292
<212> TYPE: PRT
<213> ORGANISM: artificial sequence
<220> FEATURE:
<223> OTHER INFORMATION: Repeat sequence with loop modification

<400> SEQUENCE: 12

Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser Asn Asn Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser Asn
65                  70                  75                  80

Gly Gly Gly Lys Gln Ala Leu Glu Thr Pro Gly Ser Gly Ser Gly Ser
                85                  90                  95

Leu Thr Pro Glu Gln Val Val Ala Ile Ala Ser Asn Gly Gly Gly Lys
            100                 105                 110

Gln Ala Leu Glu Thr Pro Gly Ser Gly Ser Gly Ser Leu Thr Pro Glu
        115                 120                 125

Gln Val Val Ala Ile Ala Ser Asn Ile Gly Gly Lys Gln Ala Leu Glu
    130                 135                 140

Thr Pro Gly Ser Gly Ser Gly Ser Leu Thr Pro Glu Gln Val Val Ala
145                 150                 155                 160

Ile Ala Ser His Asp Gly Gly Lys Gln Ala Leu Glu Thr Pro Gly Ser
                165                 170                 175

Gly Ser Gly Ser Leu Thr Pro Glu Gln Val Val Ala Ile Ala Ser Asn
            180                 185                 190

Gly Gly Gly Lys Gln Ala Leu Glu Thr Pro Gly Ser Gly Ser Gly Ser
        195                 200                 205

Leu Thr Pro Glu Gln Val Val Ala Ile Ala Ser Asn Gly Gly Gly Lys
    210                 215                 220

Gln Ala Leu Glu Thr Pro Gly Ser Gly Ser Gly Ser Leu Thr Pro Glu
225                 230                 235                 240

Gln Val Val Ala Ile Ala Ser Asn Ile Gly Gly Lys Gln Ala Leu Glu
                245                 250                 255

Thr Pro Gly Ser Gly Ser Gly Ser Leu Thr Pro Glu Gln Val Val Ala
            260                 265                 270

Ile Ala Ser Asn Gly Gly Gly Lys Gln Ala Leu Glu Thr Pro Gly Ser
        275                 280                 285

Gly Ser Gly Ser
    290
```

<210> SEQ ID NO 13
<211> LENGTH: 340
<212> TYPE: PRT
<213> ORGANISM: artificial sequence
<220> FEATURE:
<223> OTHER INFORMATION: Repeat sequence with loop modification

<400> SEQUENCE: 13

```
Leu Thr Pro Glu Gln Val Val Ala Ile Ala Ser Asn Asn Gly Gly Lys
1               5                   10                  15

Gln Ala Leu Glu Thr Pro Gln Arg Leu Leu Pro Gly Ser Gly Ser Gly
                20                  25                  30

Ser Gly Ser Gly Pro Glu Gln Val Val Ala Ile Ala Ser Asn Asn Gly
            35                  40                  45

Gly Lys Gln Ala Leu Glu Thr Pro Gln Arg Leu Leu Pro Gly Ser Gly
50                  55                  60

Ser Gly Ser Gly Ser Gly Pro Glu Gln Val Val Ala Ile Ala Ser Asn
65                  70                  75                  80

Asn Gly Gly Lys Gln Ala Leu Glu Thr Pro Gln Arg Leu Leu Pro Gly
                85                  90                  95

Ser Gly Ser Gly Ser Gly Ser Gly Pro Glu Gln Val Val Ala Ile Ala
            100                 105                 110

Ser Asn Gly Gly Lys Gln Ala Leu Glu Thr Pro Gln Arg Leu Leu
            115                 120                 125

Pro Gly Ser Gly Ser Gly Ser Gly Ser Gly Pro Glu Gln Val Val Ala
            130                 135                 140

Ile Ala Ser Asn Ile Gly Gly Lys Gln Ala Leu Glu Thr Pro Gln Arg
145                 150                 155                 160

Leu Leu Pro Gly Ser Gly Ser Gly Ser Gly Ser Gly Pro Glu Gln Val
                165                 170                 175

Val Ala Ile Ala Ser His Asp Gly Gly Lys Gln Ala Leu Glu Thr Pro
            180                 185                 190

Gln Arg Leu Leu Pro Gly Ser Gly Ser Gly Ser Gly Ser Gly Pro Glu
            195                 200                 205

Gln Val Val Ala Ile Ala Ser Asn Gly Gly Lys Gln Ala Leu Glu
            210                 215                 220

Thr Pro Gln Arg Leu Leu Pro Gly Ser Gly Ser Gly Ser Gly Ser Gly
225                 230                 235                 240

Pro Glu Gln Val Val Ala Ile Ala Ser Asn Gly Gly Lys Gln Ala
            245                 250                 255

Leu Glu Thr Pro Gln Arg Leu Leu Pro Gly Ser Gly Ser Gly Ser Gly
                260                 265                 270

Ser Gly Pro Glu Gln Val Val Ala Ile Ala Ser Asn Ile Gly Gly Lys
            275                 280                 285

Gln Ala Leu Glu Thr Pro Gln Arg Leu Leu Pro Gly Ser Gly Ser Gly
            290                 295                 300

Ser Gly Ser Gly Pro Glu Gln Val Val Ala Ile Ala Ser Asn Gly Gly
305                 310                 315                 320

Gly Lys Gln Ala Leu Glu Thr Pro Gln Arg Leu Leu Pro Gly Ser Gly
                325                 330                 335

Ser Gly Ser Gly
            340
```

<210> SEQ ID NO 14
<211> LENGTH: 298

```
<212> TYPE: PRT
<213> ORGANISM: artificial sequence
<220> FEATURE:
<223> OTHER INFORMATION: Repeat sequence with loop modification

<400> SEQUENCE: 14

Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Asn Gly
        35                  40                  45

Gly Lys Gln Ala Leu Glu Thr Val Gln Arg Leu Leu Pro Val Leu Cys
50                  55                  60

Gln Ala His Gly Ser Gly Pro Ser Gly Pro Ala Ile Ala Ser Asn
65                  70                  75                  80

Gly Gly Gly Lys Gln Ala Leu Glu Thr Pro Gly Ser Gly Ser Gly Ser
                85                  90                  95

Ser Gly Pro Gly Ser Gly Pro Ala Ile Ala Ser Asn Gly Gly Gly Lys
            100                 105                 110

Gln Ala Leu Glu Thr Pro Gly Ser Gly Ser Gly Ser Gly Pro Gly
            115                 120                 125

Ser Gly Pro Ala Ile Ala Ser Asn Ile Gly Gly Lys Gln Ala Leu Glu
            130                 135                 140

Thr Pro Gly Ser Gly Ser Gly Ser Gly Pro Gly Ser Gly Pro Ala
145                 150                 155                 160

Ile Ala Ser His Asp Gly Gly Lys Gln Ala Leu Glu Thr Pro Gly Ser
                165                 170                 175

Gly Ser Gly Ser Ser Gly Pro Gly Ser Gly Pro Ala Ile Ala Ser Asn
            180                 185                 190

Gly Gly Gly Lys Gln Ala Leu Glu Thr Pro Gly Ser Gly Ser Gly Ser
            195                 200                 205

Ser Gly Pro Gly Ser Gly Pro Ala Ile Ala Ser Asn Gly Gly Gly Lys
            210                 215                 220

Gln Ala Leu Glu Thr Pro Gly Ser Gly Ser Gly Ser Ser Gly Pro Gly
225                 230                 235                 240

Ser Gly Pro Ala Ile Ala Ser Asn Ile Gly Gly Lys Gln Ala Leu Glu
                245                 250                 255

Thr Pro Gly Ser Gly Ser Gly Ser Leu Thr Pro Glu Gln Val Val Ala
            260                 265                 270

Ile Ala Ser Asn Gly Gly Gly Lys Gln Ala Leu Glu Thr Val Gln Arg
            275                 280                 285

Leu Leu Pro Val Leu Cys Gln Ala His Gly
        290                 295

<210> SEQ ID NO 15
<211> LENGTH: 360
<212> TYPE: PRT
<213> ORGANISM: artificial sequence
<220> FEATURE:
<223> OTHER INFORMATION: Repeat structure derived from MTERF1 structure

<400> SEQUENCE: 15

Asn Ile Ser Ile Ser Gln Ile Ile Glu Asn Ala Ile Ala Ser Asn Asn
1               5                   10                  15

Gly Gly Ile Ser Thr Leu Lys Ser Arg Ile Lys Glu Leu Val Asn Ala
            20                  25                  30
```

```
Gly Cys Asn Leu Asn Ile Ser Ile Ser Gln Ile Ile Glu Asn Ala Ile
            35                  40                  45

Ala Ser Asn Asn Gly Gly Ile Ser Thr Leu Lys Ser Arg Ile Lys Glu
 50                  55                  60

Leu Val Asn Ala Gly Cys Asn Leu Asn Ile Ser Ile Ser Gln Ile Ile
 65                  70                  75                  80

Glu Asn Ala Ile Ala Ser Asn Gly Gly Gly Ile Ser Thr Leu Lys Ser
                 85                  90                  95

Arg Ile Lys Glu Leu Val Asn Ala Gly Cys Asn Leu Asn Ile Ser Ile
            100                 105                 110

Ser Gln Ile Ile Glu Asn Ala Ile Ala Ser Asn Gly Gly Gly Ile Ser
            115                 120                 125

Thr Leu Lys Ser Arg Ile Lys Glu Leu Val Asn Ala Gly Cys Asn Leu
130                 135                 140

Asn Ile Ser Ile Ser Gln Ile Ile Glu Asn Ala Ile Ala Ser Asn Ile
145                 150                 155                 160

Gly Gly Ile Ser Thr Leu Lys Ser Arg Ile Lys Glu Leu Val Asn Ala
                165                 170                 175

Gly Cys Asn Leu Asn Ile Ser Ile Ser Gln Ile Ile Glu Asn Ala Ile
            180                 185                 190

Ala Ser His Asp Gly Gly Ile Ser Thr Leu Lys Ser Arg Ile Lys Glu
            195                 200                 205

Leu Val Asn Ala Gly Cys Asn Leu Asn Ile Ser Ile Ser Gln Ile Ile
            210                 215                 220

Glu Asn Ala Ile Ala Ser Asn Gly Gly Gly Ile Ser Thr Leu Lys Ser
225                 230                 235                 240

Arg Ile Lys Glu Leu Val Asn Ala Gly Cys Asn Leu Asn Ile Ser Ile
                245                 250                 255

Ser Gln Ile Ile Glu Asn Ala Ile Ala Ser Asn Gly Gly Gly Ile Ser
                260                 265                 270

Thr Leu Lys Ser Arg Ile Lys Glu Leu Val Asn Ala Gly Cys Asn Leu
            275                 280                 285

Asn Ile Ser Ile Ser Gln Ile Ile Glu Asn Ala Ile Ala Ser Asn Ile
            290                 295                 300

Gly Gly Ile Ser Thr Leu Lys Ser Arg Ile Lys Glu Leu Val Asn Ala
305                 310                 315                 320

Gly Cys Asn Leu Asn Ile Ser Ile Ser Gln Ile Ile Glu Asn Ala Ile
                325                 330                 335

Ala Ser Asn Gly Gly Gly Ile Ser Thr Leu Lys Ser Arg Ile Lys Glu
            340                 345                 350

Leu Val Asn Ala Gly Cys Asn Leu
            355                 360

<210> SEQ ID NO 16
<211> LENGTH: 356
<212> TYPE: PRT
<213> ORGANISM: artificial sequence
<220> FEATURE:
<223> OTHER INFORMATION: Repeat structure derived from MTERF1 structure

<400> SEQUENCE: 16

Leu Thr Pro Glu Gln Val Val Ala Ile Ala Ser Asn Asn Gly Gly Lys
 1               5                  10                  15

Gln Ala Leu Glu Thr Val Gln Arg Leu Leu Pro Val Leu Cys Gln Ala
                20                  25                  30
```

```
His Gly Asn Ile Ser Ile Ser Gln Ile Ile Glu Asn Ala Ile Ala Ser
        35                  40                  45

Asn Asn Gly Gly Ile Ser Thr Leu Lys Ser Arg Ile Lys Glu Leu Val
50                  55                  60

Asn Ala Gly Cys Asn Leu Asn Ile Ser Ile Ser Gln Ile Ile Glu Asn
65                  70                  75                  80

Ala Ile Ala Ser Asn Gly Gly Gly Ile Ser Thr Leu Lys Ser Arg Ile
                85                  90                  95

Lys Glu Leu Val Asn Ala Gly Cys Asn Leu Asn Ile Ser Ile Ser Gln
            100                 105                 110

Ile Ile Glu Asn Ala Ile Ala Ser Asn Gly Gly Gly Ile Ser Thr Leu
            115                 120                 125

Lys Ser Arg Ile Lys Glu Leu Val Asn Ala Gly Cys Asn Leu Asn Ile
        130                 135                 140

Ser Ile Ser Gln Ile Ile Glu Asn Ala Ile Ala Ser Asn Ile Gly Gly
145                 150                 155                 160

Ile Ser Thr Leu Lys Ser Arg Ile Lys Glu Leu Val Asn Ala Gly Cys
                165                 170                 175

Asn Leu Asn Ile Ser Ile Ser Gln Ile Ile Glu Asn Ala Ile Ala Ser
            180                 185                 190

His Asp Gly Gly Ile Ser Thr Leu Lys Ser Arg Ile Lys Glu Leu Val
            195                 200                 205

Asn Ala Gly Cys Asn Leu Asn Ile Ser Ile Ser Gln Ile Ile Glu Asn
        210                 215                 220

Ala Ile Ala Ser Asn Gly Gly Gly Ile Ser Thr Leu Lys Ser Arg Ile
225                 230                 235                 240

Lys Glu Leu Val Asn Ala Gly Cys Asn Leu Asn Ile Ser Ile Ser Gln
                245                 250                 255

Ile Ile Glu Asn Ala Ile Ala Ser Asn Gly Gly Gly Ile Ser Thr Leu
            260                 265                 270

Lys Ser Arg Ile Lys Glu Leu Val Asn Ala Gly Cys Asn Leu Asn Ile
        275                 280                 285

Ser Ile Ser Gln Ile Ile Glu Asn Ala Ile Ala Ser Asn Ile Gly Gly
        290                 295                 300

Ile Ser Thr Leu Lys Ser Arg Ile Lys Glu Leu Val Asn Ala Gly Cys
305                 310                 315                 320

Asn Leu Leu Thr Pro Glu Gln Val Val Ala Ile Ala Ser Asn Gly Gly
                325                 330                 335

Gly Lys Gln Ala Leu Glu Thr Val Gln Arg Leu Leu Pro Val Leu Cys
            340                 345                 350

Gln Ala His Gly
        355

<210> SEQ ID NO 17
<211> LENGTH: 330
<212> TYPE: PRT
<213> ORGANISM: artificial sequence
<220> FEATURE:
<223> OTHER INFORMATION: Repeat structure derived from MTERF1 structure

<400> SEQUENCE: 17

Glu Glu Val Gln Lys Phe Val Leu Ser Asn Asn Gly Gly Lys Gln Glu
1               5                   10                  15

Lys Lys Phe Asn Asp Lys Ile Asp Cys Leu Met Glu Glu Asn Ile Ser
            20                  25                  30
```

```
Ile Glu Glu Val Gln Lys Phe Val Leu Ser Asn Asn Gly Gly Lys Gln
            35                  40                  45

Glu Lys Lys Phe Asn Asp Lys Ile Asp Cys Leu Met Glu Glu Asn Ile
 50                  55                  60

Ser Ile Glu Glu Val Gln Lys Phe Val Leu Ser Asn Gly Gly Gly Lys
 65                  70                  75                  80

Gln Glu Lys Lys Phe Asn Asp Lys Ile Asp Cys Leu Met Glu Glu Asn
            85                  90                  95

Ile Ser Ile Glu Glu Val Gln Lys Phe Val Leu Ser Asn Gly Gly Gly
           100                 105                 110

Lys Gln Glu Lys Lys Phe Asn Asp Lys Ile Asp Cys Leu Met Glu Glu
           115                 120                 125

Asn Ile Ser Ile Glu Glu Val Gln Lys Phe Val Leu Ser Asn Ile Gly
           130                 135                 140

Gly Lys Gln Glu Lys Lys Phe Asn Asp Lys Ile Asp Cys Leu Met Glu
145                 150                 155                 160

Glu Asn Ile Ser Ile Glu Glu Val Gln Lys Phe Val Leu Ser His Asp
                165                 170                 175

Gly Gly Lys Gln Glu Lys Lys Phe Asn Asp Lys Ile Asp Cys Leu Met
           180                 185                 190

Glu Glu Asn Ile Ser Ile Glu Glu Val Gln Lys Phe Val Leu Ser Asn
           195                 200                 205

Gly Gly Gly Lys Gln Glu Lys Lys Phe Asn Asp Lys Ile Asp Cys Leu
           210                 215                 220

Met Glu Glu Asn Ile Ser Ile Glu Glu Val Gln Lys Phe Val Leu Ser
225                 230                 235                 240

Asn Gly Gly Gly Lys Gln Glu Lys Lys Phe Asn Asp Lys Ile Asp Cys
                245                 250                 255

Leu Met Glu Glu Asn Ile Ser Ile Glu Glu Val Gln Lys Phe Val Leu
           260                 265                 270

Ser Asn Ile Gly Gly Lys Gln Glu Lys Lys Phe Asn Asp Lys Ile Asp
           275                 280                 285

Cys Leu Met Glu Glu Asn Ile Ser Ile Glu Glu Val Gln Lys Phe Val
           290                 295                 300

Leu Ser Asn Gly Gly Gly Lys Gln Glu Lys Lys Phe Asn Asp Lys Ile
305                 310                 315                 320

Asp Cys Leu Met Glu Glu Asn Ile Ser Ile
           325                 330

<210> SEQ ID NO 18
<211> LENGTH: 332
<212> TYPE: PRT
<213> ORGANISM: artificial sequence
<220> FEATURE:
<223> OTHER INFORMATION: Repeat structure derived from MTERF1 structure

<400> SEQUENCE: 18

Leu Thr Pro Glu Gln Val Val Ala Ile Ala Ser Asn Asn Gly Gly Lys
 1               5                  10                  15

Gln Ala Leu Glu Thr Val Gln Arg Leu Leu Pro Val Leu Cys Gln Ala
            20                  25                  30

His Gly Glu Glu Val Gln Lys Phe Val Leu Ser Asn Asn Gly Gly Lys
            35                  40                  45

Gln Glu Lys Lys Phe Asn Asp Lys Ile Asp Cys Leu Met Glu Glu Asn
 50                  55                  60
```

```
Ile Ser Ile Glu Glu Val Gln Lys Phe Val Leu Ser Asn Gly Gly
 65                  70                  75                  80

Lys Gln Glu Lys Lys Phe Asn Asp Lys Ile Asp Cys Leu Met Glu Glu
                 85                  90                  95

Asn Ile Ser Ile Glu Glu Val Gln Lys Phe Val Leu Ser Asn Gly Gly
            100                 105                 110

Gly Lys Gln Glu Lys Lys Phe Asn Asp Lys Ile Asp Cys Leu Met Glu
            115                 120                 125

Glu Asn Ile Ser Ile Glu Glu Val Gln Lys Phe Val Leu Ser Asn Ile
130                 135                 140

Gly Gly Lys Gln Glu Lys Lys Phe Asn Asp Lys Ile Asp Cys Leu Met
145                 150                 155                 160

Glu Glu Asn Ile Ser Ile Glu Glu Val Gln Lys Phe Val Leu Ser His
                165                 170                 175

Asp Gly Gly Lys Gln Glu Lys Lys Phe Asn Asp Lys Ile Asp Cys Leu
            180                 185                 190

Met Glu Glu Asn Ile Ser Ile Glu Glu Val Gln Lys Phe Val Leu Ser
            195                 200                 205

Asn Gly Gly Gly Lys Gln Glu Lys Lys Phe Asn Asp Lys Ile Asp Cys
210                 215                 220

Leu Met Glu Glu Asn Ile Ser Ile Glu Glu Val Gln Lys Phe Val Leu
225                 230                 235                 240

Ser Asn Gly Gly Gly Lys Gln Glu Lys Lys Phe Asn Asp Lys Ile Asp
                245                 250                 255

Cys Leu Met Glu Glu Asn Ile Ser Ile Glu Glu Val Gln Lys Phe Val
            260                 265                 270

Leu Ser Asn Ile Gly Gly Lys Gln Glu Lys Lys Phe Asn Asp Lys Ile
            275                 280                 285

Asp Cys Leu Met Glu Glu Asn Ile Ser Ile Leu Thr Pro Glu Gln Val
            290                 295                 300

Val Ala Ile Ala Ser Asn Gly Gly Lys Gln Ala Leu Glu Thr Val
305                 310                 315                 320

Gln Arg Leu Leu Pro Val Leu Cys Gln Ala His Gly
                325                 330
```

<210> SEQ ID NO 19
<211> LENGTH: 34
<212> TYPE: PRT
<213> ORGANISM: artificial sequence
<220> FEATURE:
<223> OTHER INFORMATION: RVD HD

<400> SEQUENCE: 19

```
Leu Thr Pro Glu Gln Val Val Ala Ile Ala Ser His Asp Gly Gly Lys
 1               5                  10                  15

Gln Ala Leu Glu Thr Val Gln Arg Leu Leu Pro Val Leu Cys Gln Ala
                20                  25                  30

His Gly
```

<210> SEQ ID NO 20
<211> LENGTH: 34
<212> TYPE: PRT
<213> ORGANISM: artificial sequence
<220> FEATURE:
<223> OTHER INFORMATION: RVD NN

<400> SEQUENCE: 20

```
Leu Thr Pro Gln Gln Val Val Ala Ile Ala Ser Asn Gly Gly Lys
1               5                   10                  15

Gln Ala Leu Glu Thr Val Gln Arg Leu Pro Val Leu Cys Gln Ala
            20                  25                  30

His Gly

<210> SEQ ID NO 21
<211> LENGTH: 34
<212> TYPE: PRT
<213> ORGANISM: artificial sequence
<220> FEATURE:
<223> OTHER INFORMATION: RVD NG

<400> SEQUENCE: 21

Leu Thr Pro Gln Gln Val Val Ala Ile Ala Ser Asn Gly Gly Lys
1               5                   10                  15

Gln Ala Leu Glu Thr Val Gln Arg Leu Pro Val Leu Cys Gln Ala
            20                  25                  30

His Gly

<210> SEQ ID NO 22
<211> LENGTH: 34
<212> TYPE: PRT
<213> ORGANISM: artificial sequence
<220> FEATURE:
<223> OTHER INFORMATION: RVD NI

<400> SEQUENCE: 22

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly

<210> SEQ ID NO 23
<211> LENGTH: 34
<212> TYPE: PRT
<213> ORGANISM: artificial sequence
<220> FEATURE:
<223> OTHER INFORMATION: RVD TL

<400> SEQUENCE: 23

Leu Thr Pro Gln Gln Val Val Ala Ile Ala Ser Thr Leu Gly Gly Lys
1               5                   10                  15

Gln Ala Leu Glu Thr Val Gln Arg Leu Pro Val Leu Cys Gln Ala
            20                  25                  30

His Gly

<210> SEQ ID NO 24
<211> LENGTH: 34
<212> TYPE: PRT
<213> ORGANISM: artificial sequence
<220> FEATURE:
<223> OTHER INFORMATION: RVD VT

<400> SEQUENCE: 24

Leu Thr Pro Glu Gln Val Val Ala Ile Ala Ser Val Thr Gly Gly Lys
1               5                   10                  15

Gln Ala Leu Glu Thr Val Gln Arg Leu Pro Val Leu Cys Gln Ala
            20                  25                  30
```

His Gly

<210> SEQ ID NO 25
<211> LENGTH: 34
<212> TYPE: PRT
<213> ORGANISM: artificial sequence
<220> FEATURE:
<223> OTHER INFORMATION: RVD SW

<400> SEQUENCE: 25

Leu Thr Pro Gln Gln Val Val Ala Ile Ala Ser Ser Trp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 26
<211> LENGTH: 22
<212> TYPE: DNA
<213> ORGANISM: artificial sequence
<220> FEATURE:
<223> OTHER INFORMATION: oligo A1

<400> SEQUENCE: 26
cccagtcacg acgttgtaaa ac                                          22

<210> SEQ ID NO 27
<211> LENGTH: 50
<212> TYPE: DNA
<213> ORGANISM: artificial sequence
<220> FEATURE:
<223> OTHER INFORMATION: oligo B1
<220> FEATURE:
<221> NAME/KEY: misc_feature
<222> LOCATION: (25)
<223> OTHER INFORMATION: h is a or c or t
<220> FEATURE:
<221> NAME/KEY: misc_feature
<222> LOCATION: (26)
<223> OTHER INFORMATION: n is a or c or t or g
<220> FEATURE:
<221> NAME/KEY: misc_feature
<222> LOCATION: (27)
<223> OTHER INFORMATION: s is c or g
<220> FEATURE:
<221> NAME/KEY: misc_feature
<222> LOCATION: (29)
<223> OTHER INFORMATION: y is c or t

<400> SEQUENCE: 27
gtctccagcg cctgcttgcc gcchnsayg ctggcgatgg ccacctgctc              50

<210> SEQ ID NO 28
<211> LENGTH: 50
<212> TYPE: DNA
<213> ORGANISM: artificial sequence
<220> FEATURE:
<223> OTHER INFORMATION: oligo B2
<220> FEATURE:
<221> NAME/KEY: misc_feature
<222> LOCATION: (25)
<223> OTHER INFORMATION: b is c or g or t
<220> FEATURE:
<221> NAME/KEY: misc_feature
<222> LOCATION: (26)
<223> OTHER INFORMATION: n is a or c or t or g
<220> FEATURE:
<221> NAME/KEY: misc_feature
<222> LOCATION: (27)
<223> OTHER INFORMATION: s is c or g

```
<220> FEATURE:
<221> NAME/KEY: misc_feature
<222> LOCATION: (29)
<223> OTHER INFORMATION: y is c or t

<400> SEQUENCE: 28
gtctccagcg cctgcttgcc gccabnsayg ctggcgatgg ccacctgctc          50

<210> SEQ ID NO 29
<211> LENGTH: 50
<212> TYPE: DNA
<213> ORGANISM: artificial sequence
<220> FEATURE:
<223> OTHER INFORMATION: oligo B3
<220> FEATURE:
<221> NAME/KEY: misc_feature
<222> LOCATION: (25)
<223> OTHER INFORMATION: h is a or c or t
<220> FEATURE:
<221> NAME/KEY: misc_feature
<222> LOCATION: (26)
<223> OTHER INFORMATION: n is a or c or t or g
<220> FEATURE:
<221> NAME/KEY: misc_feature
<222> LOCATION: (28)
<223> OTHER INFORMATION: s is c or g
<220> FEATURE:
<221> NAME/KEY: misc_feature
<222> LOCATION: (29)
<223> OTHER INFORMATION: y is c or t

<400> SEQUENCE: 29
gtctccagcg cctgcttgcc gccchnsayg ctggcgatgg ccacctgctc          50

<210> SEQ ID NO 30
<211> LENGTH: 50
<212> TYPE: DNA
<213> ORGANISM: artificial sequence
<220> FEATURE:
<223> OTHER INFORMATION: oligo B4
<220> FEATURE:
<221> NAME/KEY: misc_feature
<222> LOCATION: (24)
<223> OTHER INFORMATION: h is a or c or t
<220> FEATURE:
<221> NAME/KEY: misc_feature
<222> LOCATION: (25)
<223> OTHER INFORMATION: b is c or g or t
<220> FEATURE:
<221> NAME/KEY: misc_feature
<222> LOCATION: (26)
<223> OTHER INFORMATION: n is a or c or t or g
<220> FEATURE:
<221> NAME/KEY: misc_feature
<222> LOCATION: (27)
<223> OTHER INFORMATION: s is c or g
<220> FEATURE:
<221> NAME/KEY: misc_feature
<222> LOCATION: (29)
<223> OTHER INFORMATION: y is c or t

<400> SEQUENCE: 30
gtctccagcg cctgcttgcc gcchbnsayg ctggcgatgg ccacctgctc          50

<210> SEQ ID NO 31
<211> LENGTH: 50
<212> TYPE: DNA
<213> ORGANISM: artificial sequence
<220> FEATURE:
<223> OTHER INFORMATION: oligo B5
<220> FEATURE:
<221> NAME/KEY: misc_feature
<222> LOCATION: (25)
```

<223> OTHER INFORMATION: w is a or t
<220> FEATURE:
<221> NAME/KEY: misc_feature
<222> LOCATION: (26)
<223> OTHER INFORMATION: d is a or g or t
<220> FEATURE:
<221> NAME/KEY: misc_feature
<222> LOCATION: (27)
<223> OTHER INFORMATION: m is a or c
<220> FEATURE:
<221> NAME/KEY: misc_feature
<222> LOCATION: (28)
<223> OTHER INFORMATION: h is a or c or t

<400> SEQUENCE: 31
gtctccagcg cctgcttgcc gccgwdmhag ctggcgatgg ccacctgctc        50

<210> SEQ ID NO 32
<211> LENGTH: 50
<212> TYPE: DNA
<213> ORGANISM: artificial sequence
<220> FEATURE:
<223> OTHER INFORMATION: oligo B6
<220> FEATURE:
<221> NAME/KEY: misc_feature
<222> LOCATION: (24)
<223> OTHER INFORMATION: m is a or c
<220> FEATURE:
<221> NAME/KEY: misc_feature
<222> LOCATION: (25)
<223> OTHER INFORMATION: h is a or c or t
<220> FEATURE:
<221> NAME/KEY: misc_feature
<222> LOCATION: (27)
<223> OTHER INFORMATION: m is a or c
<220> FEATURE:
<221> NAME/KEY: misc_feature
<222> LOCATION: (28)
<223> OTHER INFORMATION: h is a or c or t

<400> SEQUENCE: 32
gtctccagcg cctgcttgcc gccmhamhag ctggcgatgg ccacctgctc        50

<210> SEQ ID NO 33
<211> LENGTH: 50
<212> TYPE: DNA
<213> ORGANISM: artificial sequence
<220> FEATURE:
<223> OTHER INFORMATION: oligo B7
<220> FEATURE:
<221> NAME/KEY: misc_feature
<222> LOCATION: (25)
<223> OTHER INFORMATION: s is c or g
<220> FEATURE:
<221> NAME/KEY: misc_feature
<222> LOCATION: (26)
<223> OTHER INFORMATION: y is c or t
<220> FEATURE:
<221> NAME/KEY: misc_feature
<222> LOCATION: (28)
<223> OTHER INFORMATION: h is a or c or t
<220> FEATURE:
<221> NAME/KEY: misc_feature
<222> LOCATION: (29)
<223> OTHER INFORMATION: n is a or c or t or g

<400> SEQUENCE: 33
gtctccagcg cctgcttgcc gccasychng ctggcgatgg ccacctgctc        50

<210> SEQ ID NO 34
<211> LENGTH: 50
<212> TYPE: DNA
<213> ORGANISM: artificial sequence

```
<220> FEATURE:
<223> OTHER INFORMATION: oligo B8
<220> FEATURE:
<221> NAME/KEY: misc_feature
<222> LOCATION: (24)
<223> OTHER INFORMATION: m is a or c
<220> FEATURE:
<221> NAME/KEY: misc_feature
<222> LOCATION: (26)
<223> OTHER INFORMATION: y is c or t
<220> FEATURE:
<221> NAME/KEY: misc_feature
<222> LOCATION: (28)
<223> OTHER INFORMATION: h is a or c or t
<220> FEATURE:
<221> NAME/KEY: misc_feature
<222> LOCATION: (29)
<223> OTHER INFORMATION: n is a or c or t or g

<400> SEQUENCE: 34
gtctccagcg cctgcttgcc gccmtychng ctggcgatgg ccacctgctc        50

<210> SEQ ID NO 35
<211> LENGTH: 23
<212> TYPE: DNA
<213> ORGANISM: artificial sequence
<220> FEATURE:
<223> OTHER INFORMATION: oligo C1

<400> SEQUENCE: 35
cacaggaaac agctatgacc atg                                    23

<210> SEQ ID NO 36
<211> LENGTH: 22
<212> TYPE: DNA
<213> ORGANISM: artificial sequence
<220> FEATURE:
<223> OTHER INFORMATION: oligo D1

<400> SEQUENCE: 36
ggcaagcagg cgctggagac gg                                     22

<210> SEQ ID NO 37
<211> LENGTH: 50
<212> TYPE: DNA
<213> ORGANISM: artificial sequence
<220> FEATURE:
<223> OTHER INFORMATION: oligo B9
<220> FEATURE:
<221> NAME/KEY: misc_feature
<222> LOCATION: (24)..(29)
<223> OTHER INFORMATION: m is a or c; n is a or c or t or g

<400> SEQUENCE: 37
gtctccagcg cctgcttgcc gccmnnmnng ctggcgatgg ccacctgctc        50

<210> SEQ ID NO 38
<211> LENGTH: 22
<212> TYPE: DNA
<213> ORGANISM: artificial sequence
<220> FEATURE:
<223> OTHER INFORMATION: biotinylated oligo A2

<400> SEQUENCE: 38
cccagtcacg acgttgtaaa ac                                     22

<210> SEQ ID NO 39
<211> LENGTH: 20
<212> TYPE: DNA
```

<213> ORGANISM: artificial sequence
<220> FEATURE:
<223> OTHER INFORMATION: oligo C2

<400> SEQUENCE: 39
cccggtaccg catctcgagg         20

<210> SEQ ID NO 40
<211> LENGTH: 3057
<212> TYPE: DNA
<213> ORGANISM: artificial sequence
<220> FEATURE:
<223> OTHER INFORMATION: pAPG10 plasmid with RVD HD

<400> SEQUENCE: 40

| | |
|---|---|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggctatggc ccactacagg caaccatca | 240 |
| ccctaatcaa gttttttggg gtcgaggtgc cgtaaagcac taaatcggaa ccctaaaggg | 300 |
| agccccgat ttagagcttg acggggaaag ccggcgaacg tggcgagaaa ggaagggaag | 360 |
| aaagcgaaag gagcgggcgc tagggcgctg gcaagtgtag cggtcacgct gcgcgtaacc | 420 |
| accacacccg ccgcgcttaa tgcgccgcta cagggcgctc ccattcgcca ttcaggctgc | 480 |
| gcaactgttg ggaagggcgt tcggtgcgg gcctcttcgc tattacgcca gctggcgaaa | 540 |
| gggggatgtg ctgcaaggcg attaagttgg gtaacgccag gttttccca gtcacgacgt | 600 |
| tgtaaaacga cggccagtga gcgcgacgta atacgactca ctatagggcg aattgggcgc | 660 |
| gcctcacagg ccggacgggc cgacgtccgc agcgacatgt tgaccccgga gcaggtggtg | 720 |
| gccatcgcca gccacgatgg cggcaagcag gcgctggaga cggtccagcg gctgttgccg | 780 |
| gtgctgtgcc aggcccacgg cttgacccctc gagatgcgt accggggcca ctggggcccc | 840 |
| tagccaaatt aattaacagc ttttgttccc tttagtgagg gttaattgac gcgcttggcg | 900 |
| taatcatggt catagctgtt tcctgtgtga aattgttatc cgctcacaat tccacacaac | 960 |
| atacgagccg gaagcataaa gtgtaaagcc tggggtgcct aatgagtgag ctaactcaca | 1020 |
| ttaattgcgt tgcgctcact gcccgctttc cagtcgggaa acctgtcgtg ccagctgcat | 1080 |
| taatgaatcg gccaacgcgc ggggagaggc ggtttgcgta ttgggcgctc tccgcttcct | 1140 |
| cgctcactga ctcgctgcgc tcggtcgttc ggctgcggcg agcggtatca gctcactcaa | 1200 |
| aggcggtaat acggttatcc acagaatcag gggataacgc aggaaagacc atgtgagcaa | 1260 |
| aaggccagca aaaggccagg aaccgtaaaa aggccgcgtt gctggcgttt ttccataggc | 1320 |
| tccgcccccc tgacgagcat cacaaaaatc gacgctcaag tcagaggtgg cgaaacccga | 1380 |
| caggactata aagataccag gcgtttcccc ctggaagctc cctcgtgcgc tctcctgttc | 1440 |
| cgaccctgcc gcttaccgga tacctgtccg cctttctccc ttcgggaagc gtggcgcttt | 1500 |
| ctcatagctc acgctgtagg tatctcagtt cggtgtaggt cgttcgctcc aagctgggct | 1560 |
| gtgtgcacga accccccgtt cagcccgacc gctgcgcctt atccggtaac tatcgtcttg | 1620 |
| agtccaaccc ggtaagacac gacttatcgc cactggcagc agccactggt aacaggatta | 1680 |
| gcagagcgag gtatgtaggc ggtgctacag agttcttgaa gtggtggcct aactacggct | 1740 |
| acactagaag aacagtattt ggtatctgcg ctctgctgaa gccagttacc ttcggaaaaa | 1800 |
| gagttggtag ctcttgatcc ggcaaacaaa ccaccgctgg tagcggtggt ttttttgttt | 1860 |

-continued

```
gcaagcagca gattacgcgc agaaaaaaag gatctcaaga agatcctttg atctttcta    1920 cggggtctga cgctcagtgg aacgaaaact cacgttaagg gattttggtc atgagattat    1980
caaaaaggat cttcacctag atcctttaa attaaaaatg aagttttaaa tcaatctaaa    2040
gtatatatga gtaaacttgg tctgacagtt accaatgctt aatcagtgag gcacctatct    2100
cagcgatctg tctatttcgt tcatccatag ttgcctgact ccccgtcgtg tagataacta    2160
cgatacggga gggcttacca tctggcccca gtgctgcaat gataccgcga gaaccacgct    2220
caccggctcc agatttatca gcaataaacc agccagccgg aagggccgag cgcagaagtg    2280
gtcctgcaac tttatccgcc tccatccagt ctattaattg ttgccgggaa gctagagtaa    2340
gtagttcgcc agttaatagt ttgcgcaacg ttgttgccat tgctacaggc atcgtggtgt    2400
cacgctcgtc gtttggtatg gcttcattca gctccggttc ccaacgatca aggcgagtta    2460
catgatcccc catgttgtgc aaaaaagcgg ttagctcctt cggtcctccg atcgttgtca    2520
gaagtaagtt ggccgcagtg ttatcactca tggttatggc agcactgcat aattctctta    2580
ctgtcatgcc atccgtaaga tgcttttctg tgactggtga gtactcaacc aagtcattct    2640
gagaatagtg tatgcggcga ccgagttgct cttgcccggc gtcaatacgg gataataccg    2700
cgccacatag cagaacttta aaagtgctca tcattggaaa acgttcttcg ggcgaaaac    2760 tctcaaggat cttaccgctg ttgagatcca gttcgatgta acccactcgt gcacccaact    2820
gatcttcagc atcttttact ttcaccagcg tttctgggtg agcaaaaaca ggaaggcaaa    2880
atgccgcaaa aaagggaata agggcgacac ggaaatgttg aatactcata ctcttccttt    2940
ttcaatatta ttgaagcatt tatcagggtt attgtctcat gagcggatac atatttgaat    3000
gtatttagaa aaataaacaa ataggggttc cgcgcacatt tccccgaaaa gtgccac      3057
```

<210> SEQ ID NO 41
<211> LENGTH: 876
<212> TYPE: DNA
<213> ORGANISM: artificial sequence
<220> FEATURE:
<223> OTHER INFORMATION: array lib1 1RVD
<220> FEATURE:
<221> NAME/KEY: misc_feature
<222> LOCATION: (34)
<223> OTHER INFORMATION: r is a or g
<220> FEATURE:
<221> NAME/KEY: misc_feature
<222> LOCATION: (36)
<223> OTHER INFORMATION: s is c or g
<220> FEATURE:
<221> NAME/KEY: misc_feature
<222> LOCATION: (37)
<223> OTHER INFORMATION: n is a or c or t or g
<220> FEATURE:
<221> NAME/KEY: misc_feature
<222> LOCATION: (38)
<223> OTHER INFORMATION: d is a or g or t

<400> SEQUENCE: 41

```
ttgaccccgg agcaggtggt ggccatcgcc agcrtsndgg gcggcaagca ggcgctggag      60
acggtccagc ggctgttgcc ggtgctgtgc caggcccacg gcttgacccc ccagcaggtg     120
gtggccatcg ccagcaataa tggtggcaag caggcgctgg agacggtcca gcggctgttg     180
ccggtgctgt gccaggccca cggcttgacc ccggagcagg tggtggccat cgccagccac     240 gatgcggca agcaggcgct ggagacggtc cagcggctgt tgccggtgct gtgccaggcc     300
cacggcttga ccccggagca ggtggtggcc atcgccagca atattggtgg caagcaggcg     360
```

```
ctggagacgg tgcaggcgct gttgccggtg ctgtgccagg cccacggctt gaccccggag      420
caggtggtgg ccatcgccag ccacgatggc ggcaagcagg cgctggagac ggtccagcgg      480
ctgttgccgg tgctgtgcca ggcccacggc ttgaccccc agcaggtggt ggccatcgcc       540
agcaatggcg gtggcaagca ggcgctggag acggtccagc ggctgttgcc ggtgctgtgc      600
caggcccacg gcttgacccc ccagcaggtg gtggccatcg ccagcaatgg cggtggcaag      660
caggcgctgg agacggtcca gcggctgttg ccggtgctgt gccaggccca cggcttgacc      720
ccggagcagg tggtggccat cgccagcaat attggtggca agcaggcgct ggagacggtg      780
caggcgctgt tgccggtgct gtgccaggcc cacggcttga cccctcagca ggtggtggcc      840
atcgccagca atggcggcgg caggccggcg ctggag                                876
```

<210> SEQ ID NO 42
<211> LENGTH: 876
<212> TYPE: DNA
<213> ORGANISM: artificial sequence
<220> FEATURE:
<223> OTHER INFORMATION: array lib2 1RVD
<220> FEATURE:
<221> NAME/KEY: misc_feature
<222> LOCATION: (34)
<223> OTHER INFORMATION: r is a or g
<220> FEATURE:
<221> NAME/KEY: misc_feature
<222> LOCATION: (36)
<223> OTHER INFORMATION: s is c or g
<220> FEATURE:
<221> NAME/KEY: misc_feature
<222> LOCATION: (37)
<223> OTHER INFORMATION: n is a or c or t or g
<220> FEATURE:
<221> NAME/KEY: misc_feature
<222> LOCATION: (38)
<223> OTHER INFORMATION: v is a or c or g

<400> SEQUENCE: 42

```
ttgaccccgg agcaggtggt ggccatcgcc agcrtsnvtg gcggcaagca ggcgctggag       60
acggtccagc ggctgttgcc ggtgctgtgc caggcccacg gcttgacccc ccagcaggtg      120
gtggccatcg ccagcaataa tggtggcaag caggcgctgg agacggtcca gcggctgttg      180
ccggtgctgt gccaggccca cggcttgacc ccggagcagg tggtggccat cgccagccac      240
gatggcggca agcaggcgct ggagacggtc agcggctgt tgccggtgct gtgccaggcc       300
cacggcttga ccccggagca ggtggtggcc atcgccagca atattggtgg caagcaggcg      360
ctggagacgg tgcaggcgct gttgccggtg ctgtgccagg cccacggctt gaccccggag      420
caggtggtgg ccatcgccag ccacgatggc ggcaagcagg cgctggagac ggtccagcgg      480
ctgttgccgg tgctgtgcca ggcccacggc ttgaccccc agcaggtggt ggccatcgcc       540
agcaatggcg gtggcaagca ggcgctggag acggtccagc ggctgttgcc ggtgctgtgc      600
caggcccacg gcttgacccc ccagcaggtg gtggccatcg ccagcaatgg cggtggcaag      660
caggcgctgg agacggtcca gcggctgttg ccggtgctgt gccaggccca cggcttgacc      720
ccggagcagg tggtggccat cgccagcaat attggtggca agcaggcgct ggagacggtg      780
caggcgctgt tgccggtgct gtgccaggcc cacggcttga cccctcagca ggtggtggcc      840
atcgccagca atggcggcgg caggccggcg ctggag                                876
```

<210> SEQ ID NO 43
<211> LENGTH: 876
<212> TYPE: DNA
<213> ORGANISM: artificial sequence

```
<220> FEATURE:
<223> OTHER INFORMATION: array lib3 1RVD
<220> FEATURE:
<221> NAME/KEY: misc_feature
<222> LOCATION: (34)
<223> OTHER INFORMATION: r is a or g
<220> FEATURE:
<221> NAME/KEY: misc_feature
<222> LOCATION: (35)
<223> OTHER INFORMATION: s is c or g
<220> FEATURE:
<221> NAME/KEY: misc_feature
<222> LOCATION: (37)
<223> OTHER INFORMATION: n is a or c or t or g
<220> FEATURE:
<221> NAME/KEY: misc_feature
<222> LOCATION: (38)
<223> OTHER INFORMATION: d is a or g or t

<400> SEQUENCE: 43
ttgaccccgg agcaggtggt ggccatcgcc agcrstndgg gcggcaagca ggcgctggag      60
acggtccagc ggctgttgcc ggtgctgtgc caggcccacg gcttgacccc ccagcaggtg     120
gtggccatcg ccagcaataa tggtggcaag caggcgctgg agacggtcca gcggctgttg     180
ccggtgctgt gccaggccca cggcttgacc ccggagcagg tggtggccat cgccagccac     240
gatggcggca agcaggcgct ggagacggtc cagcggctgt tgccggtgct gtgccaggcc     300
cacggcttga ccccggagca ggtggtggcc atcgccagca atattggtgg caagcaggcg     360
ctggagacgg tgcaggcgct gttgccggtg ctgtgccagg cccacggctt gaccccggag     420
caggtggtgg ccatcgccag ccacgatggc ggcaagcagg cgctggagac ggtccagcgg     480
ctgttgccgg tgctgtgcca ggcccacggc ttgaccccc agcaggtggt ggccatcgcc     540
agcaatggcg gtggcaagca ggcgctggag acggtccagc ggctgttgcc ggtgctgtgc     600
caggcccacg gcttgacccc ccagcaggtg gtggccatcg ccagcaatgg cggtggcaag     660
caggcgctgg agacggtcca gcggctgttg ccggtgctgt gccaggccca cggcttgacc     720
ccggagcagg tggtggccat cgccagcaat attggtggca agcaggcgct ggagacggtg     780
caggcgctgt tgccggtgct gtgccaggcc cacggcttga ccctcagca ggtggtggcc     840 atcgccagca atggcggcgg caggccggcg ctggag                                876

<210> SEQ ID NO 44
<211> LENGTH: 876
<212> TYPE: DNA
<213> ORGANISM: artificial sequence
<220> FEATURE:
<223> OTHER INFORMATION: array lib4 1RVD
<220> FEATURE:
<221> NAME/KEY: misc_feature
<222> LOCATION: (34)
<223> OTHER INFORMATION: r is a or g
<220> FEATURE:
<221> NAME/KEY: misc_feature
<222> LOCATION: (36)
<223> OTHER INFORMATION: s is c or g
<220> FEATURE:
<221> NAME/KEY: misc_feature
<222> LOCATION: (37)
<223> OTHER INFORMATION: n is a or c or t or g
<220> FEATURE:
<221> NAME/KEY: misc_feature
<222> LOCATION: (38)
<223> OTHER INFORMATION: v is a or c or g
<220> FEATURE:
<221> NAME/KEY: misc_feature
<222> LOCATION: (39)
<223> OTHER INFORMATION: d is a or g or t
```

<400> SEQUENCE: 44

```
ttgaccccgg agcaggtggt ggccatcgcc agcrtsnvdg gcggcaagca ggcgctggag      60
acggtccagc ggctgttgcc ggtgctgtgc caggcccacg gcttgacccc ccagcaggtg     120
gtggccatcg ccagcaataa tggtggcaag caggcgctgg agacggtcca gcggctgttg     180
ccggtgctgt gccaggccca cggcttgacc ccggagcagg tggtggccat cgccagccac     240
gatggcggca agcaggcgct ggagacggtc agcggctgt tgccggtgct gtgccaggcc      300
cacggcttga ccccggagca ggtggtggcc atcgccagca atattggtgg caagcaggcg     360
ctggagacgg tgcaggcgct gttgccggtg ctgtgccagg cccacggctt gaccccggag     420
caggtggtgg ccatcgccag ccacgatggc ggcaagcagg cgctggagac ggtccagcgg     480
ctgttgccgg tgctgtgcca ggcccacggc ttgacccccc agcaggtggt ggccatcgcc     540
agcaatggcg gtggcaagca ggcgctggag acggtccagc ggctgttgcc ggtgctgtgc     600
caggcccacg gcttgacccc ccagcaggtg gtggccatcg ccagcaatgg cggtggcaag     660
caggcgctgg agacggtcca gcggctgttg ccggtgctgt gccaggccca cggcttgacc     720
ccggagcagg tggtggccat cgccagcaat attggtggca agcaggcgct ggagacggtg     780
caggcgctgt tgccggtgct gtgccaggcc cacggcttga ccccctcagca ggtggtggcc     840 atcgccagca atggcggcgg caggccggcg ctggag                                876
```

<210> SEQ ID NO 45
<211> LENGTH: 876
<212> TYPE: DNA
<213> ORGANISM: artificial sequence
<220> FEATURE:
<223> OTHER INFORMATION: array lib5 1RVD
<220> FEATURE:
<221> NAME/KEY: misc_feature
<222> LOCATION: (35)
<223> OTHER INFORMATION: d is a or g or t
<220> FEATURE:
<221> NAME/KEY: misc_feature
<222> LOCATION: (36)
<223> OTHER INFORMATION: k is g or t
<220> FEATURE:
<221> NAME/KEY: misc_feature
<222> LOCATION: (37)
<223> OTHER INFORMATION: h is a or c or t
<220> FEATURE:
<221> NAME/KEY: misc_feature
<222> LOCATION: (38)
<223> OTHER INFORMATION: w is a or t

<400> SEQUENCE: 45

```
ttgaccccgg agcaggtggt ggccatcgcc agctdkhwcg gcggcaagca ggcgctggag      60
acggtccagc ggctgttgcc ggtgctgtgc caggcccacg gcttgacccc ccagcaggtg     120
gtggccatcg ccagcaataa tggtggcaag caggcgctgg agacggtcca gcggctgttg     180
ccggtgctgt gccaggccca cggcttgacc ccggagcagg tggtggccat cgccagccac     240
gatggcggca agcaggcgct ggagacggtc agcggctgt tgccggtgct gtgccaggcc      300
cacggcttga ccccggagca ggtggtggcc atcgccagca atattggtgg caagcaggcg     360
ctggagacgg tgcaggcgct gttgccggtg ctgtgccagg cccacggctt gaccccggag     420
caggtggtgg ccatcgccag ccacgatggc ggcaagcagg cgctggagac ggtccagcgg     480
ctgttgccgg tgctgtgcca ggcccacggc ttgacccccc agcaggtggt ggccatcgcc     540
agcaatggcg gtggcaagca ggcgctggag acggtccagc ggctgttgcc ggtgctgtgc     600
caggcccacg gcttgacccc ccagcaggtg gtggccatcg ccagcaatgg cggtggcaag     660
```

```
caggcgctgg agacggtcca gcggctgttg ccggtgctgt gccaggccca cggcttgacc      720
ccggagcagg tggtggccat cgccagcaat attggtggca agcaggcgct ggagacggtg      780
caggcgctgt tgccggtgct gtgccaggcc cacggcttga cccctcagca ggtggtggcc      840
atcgccagca atggcggcgg caggccggcg ctggag                                876
```

<210> SEQ ID NO 46
<211> LENGTH: 876
<212> TYPE: DNA
<213> ORGANISM: artificial sequence
<220> FEATURE:
<223> OTHER INFORMATION: array lib6 1RVD
<220> FEATURE:
<221> NAME/KEY: misc_feature
<222> LOCATION: (35)
<223> OTHER INFORMATION: d is a or g or t
<220> FEATURE:
<221> NAME/KEY: misc_feature
<222> LOCATION: (36)
<223> OTHER INFORMATION: k is g or t
<220> FEATURE:
<221> NAME/KEY: misc_feature
<222> LOCATION: (38)
<223> OTHER INFORMATION: d is a or g or t
<220> FEATURE:
<221> NAME/KEY: misc_feature
<222> LOCATION: (39)
<223> OTHER INFORMATION: k is g or t

<400> SEQUENCE: 46

```
ttgaccccgg agcaggtggt ggccatcgcc agctdktdkg gcggcaagca ggcgctggag       60
acggtccagc ggctgttgcc ggtgctgtgc caggcccacg gcttgacccc ccagcaggtg      120
gtggccatcg ccagcaataa tggtggcaag caggcgctgg agacggtcca gcggctgttg      180
ccggtgctgt gccaggccca cggcttgacc ccggagcagg tggtggccat cgccagccac      240
gatggcggca agcaggcgct ggagacggtc agcggctgt tgccggtgct gtgccaggcc      300
cacggcttga ccccggagca ggtggtggcc atcgccagca atattggtgg caagcaggcg      360
ctggagacgg tgcaggcgct gttgccggtc tgtgccagg cccacggctt gaccccggag      420
caggtggtgg ccatcgccag ccacgatggc ggcaagcagg cgctggagac ggtccagcgg      480
ctgttgccgg tgctgtgcca ggcccacggc ttgacccccc agcaggtggt ggccatcgcc      540
agcaatggcg gtggcaagca ggcgctggag acggtccagc ggctgttgcc ggtgctgtgc      600
caggcccacg gcttgacccc cagcaggtg gtggccatcg ccagcaatgg cggtggcaag      660
caggcgctgg agacggtcca gcggctgttg ccggtgctgt gccaggccca cggcttgacc      720
ccggagcagg tggtggccat cgccagcaat attggtggca agcaggcgct ggagacggtg      780
caggcgctgt tgccggtgct gtgccaggcc cacggcttga cccctcagca ggtggtggcc      840
atcgccagca atggcggcgg caggccggcg ctggag                                876
```

<210> SEQ ID NO 47
<211> LENGTH: 876
<212> TYPE: DNA
<213> ORGANISM: artificial sequence
<220> FEATURE:
<223> OTHER INFORMATION: array lib7 1RVD
<220> FEATURE:
<221> NAME/KEY: misc_feature
<222> LOCATION: (34)
<223> OTHER INFORMATION: n is a or c or t or g
<220> FEATURE:
<221> NAME/KEY: misc_feature
<222> LOCATION: (35)

```
<223> OTHER INFORMATION: d is a or g or t
<220> FEATURE:
<221> NAME/KEY: misc_feature
<222> LOCATION: (37)
<223> OTHER INFORMATION: r is a or g
<220> FEATURE:
<221> NAME/KEY: misc_feature
<222> LOCATION: (38)
<223> OTHER INFORMATION: s is c or g

<400> SEQUENCE: 47
ttgaccccgg agcaggtggt ggccatcgcc agcndgrstg gcggcaagca ggcgctggag      60
acggtccagc ggctgttgcc ggtgctgtgc caggcccacg gcttgacccc ccagcaggtg     120
gtggccatcg ccagcaataa tggtggcaag caggcgctgg agacggtcca gcggctgttg     180
ccggtgctgt gccaggccca cggcttgacc ccggagcagg tggtggccat cgccagccac     240
gatggcggca agcaggcgct ggagacggtc agcggctgt tgccggtgct gtgccaggcc     300
cacggcttga ccccggagca ggtggtggcc atcgccagca atattggtgg caagcaggcg     360
ctggagacgg tgcaggcgct gttgccggtg ctgtgccagg cccacggctt gaccccggag     420
caggtggtgg ccatcgccag ccacgatggc ggcaagcagg cgctggagac ggtccagcgg     480
ctgttgccgg tgctgtgcca ggcccacggc ttgaccccc agcaggtggt ggccatcgcc      540
agcaatggcg gtggcaagca ggcgctggag acggtccagc ggctgttgcc ggtgctgtgc     600
caggcccacg gcttgacccc ccagcaggtg gtggccatcg ccagcaatgg cggtggcaag     660
caggcgctgg agacggtcca gcggctgttg ccggtgctgt gccaggccca cggcttgacc     720
ccggagcagg tggtggccat cgccagcaat attggtggca agcaggcgct ggagacggtg     780
caggcgctgt tgccggtgct gtgccaggcc cacggcttga ccctcagca ggtggtggcc      840 atcgccagca atggcggcgg caggccggcg ctggag                               876

<210> SEQ ID NO 48
<211> LENGTH: 876
<212> TYPE: DNA
<213> ORGANISM: artificial sequence
<220> FEATURE:
<223> OTHER INFORMATION: array lib8 1RVD
<220> FEATURE:
<221> NAME/KEY: misc_feature
<222> LOCATION: (34)
<223> OTHER INFORMATION: n is a or c or t or g
<220> FEATURE:
<221> NAME/KEY: misc_feature
<222> LOCATION: (35)
<223> OTHER INFORMATION: d is a or g or t
<220> FEATURE:
<221> NAME/KEY: misc_feature
<222> LOCATION: (37)
<223> OTHER INFORMATION: r is a or g
<220> FEATURE:
<221> NAME/KEY: misc_feature
<222> LOCATION: (39)
<223> OTHER INFORMATION: k is g or t

<400> SEQUENCE: 48
ttgaccccgg agcaggtggt ggccatcgcc agcndgrakg gcggcaagca ggcgctggag      60
acggtccagc ggctgttgcc ggtgctgtgc caggcccacg gcttgacccc ccagcaggtg     120
gtggccatcg ccagcaataa tggtggcaag caggcgctgg agacggtcca gcggctgttg     180
ccggtgctgt gccaggccca cggcttgacc ccggagcagg tggtggccat cgccagccac     240
gatggcggca agcaggcgct ggagacggtc agcggctgt tgccggtgct gtgccaggcc     300
cacggcttga ccccggagca ggtggtggcc atcgccagca atattggtgg caagcaggcg     360
```

```
ctggagacgg tgcaggcgct gttgccggtg ctgtgccagg cccacggctt gaccccggag    420
caggtggtgg ccatcgccag ccacgatggc ggcaagcagg cgctggagac ggtccagcgg    480
ctgttgccgg tgctgtgcca ggcccacggc ttgaccccc agcaggtggt ggccatcgcc     540
agcaatggcg gtggcaagca ggcgctggag acggtccagc ggctgttgcc ggtgctgtgc    600
caggcccacg gcttgacccc cagcaggtg gtggccatcg ccagcaatgg cggtggcaag     660
caggcgctga gacggtccag cggctgttgc cggtgctgt gccaggccca cggcttgacc     720
ccggagcagg tggtggccat cgccagcaat attggtggca agcaggcgct ggagacggtg    780
caggcgctgt tgccggtgct gtgccaggcc acggcttga ccccctcagca ggtggtggcc    840 atcgccagca atggcggcgg caggccggcg ctggag                              876
```

<210> SEQ ID NO 49
<211> LENGTH: 876
<212> TYPE: DNA
<213> ORGANISM: artificial sequence
<220> FEATURE:
<223> OTHER INFORMATION: array lib9 1RVD
<220> FEATURE:
<221> NAME/KEY: misc_feature
<222> LOCATION: (34)..(39)
<223> OTHER INFORMATION: k is g or t; n is a or c or t or g

<400> SEQUENCE: 49

```
ttgaccccgg agcaggtggt ggccatcgcc agcnnknnkg gcggcaagca ggcgctggag     60
acggtccagc ggctgttgcc ggtgctgtgc caggcccacg gcttgacccc ccagcaggtg    120
gtggccatcg ccagcaataa tggtggcaag caggcgctga gacggtccag cggctgttg    180 ccggtgctgt gccaggccca cggcttgacc ccggagcagg tggtggccat cgccagccac    240
gatggcggca agcaggcgct ggagacggtc cagcggctgt tgccggtgct gtgccaggcc    300
cacggcttga ccccggagca ggtggtggcc atcgccagca atattggtgg caagcaggcg    360
ctggagacgg tgcaggcgct gttgccggtg ctgtgccagg cccacggctt gaccccggag    420
caggtggtgg ccatcgccag ccacgatggc ggcaagcagg cgctggagac ggtccagcgg    480
ctgttgccgg tgctgtgcca ggcccacggc ttgaccccc agcaggtggt ggccatcgcc     540
agcaatggcg gtggcaagca ggcgctggag acggtccagc ggctgttgcc ggtgctgtgc    600
caggcccacg gcttgacccc cagcaggtg gtggccatcg ccagcaatgg cggtggcaag     660
caggcgctgg agacggtcca gcggctgttg ccggtgctgt gccaggccca cggcttgacc    720
ccggagcagg tggtggccat cgccagcaat attggtggca agcaggcgct ggagacggtg    780
caggcgctgt tgccggtgct gtgccaggcc acggcttga ccccctcagca ggtggtggcc    840 atcgccagca atggcggcgg caggccggcg ctggag                              876
```

<210> SEQ ID NO 50
<211> LENGTH: 978
<212> TYPE: DNA
<213> ORGANISM: artificial sequence
<220> FEATURE:
<223> OTHER INFORMATION: array lib1 2RVD
<220> FEATURE:
<221> NAME/KEY: misc_feature
<222> LOCATION: (34)
<223> OTHER INFORMATION: r is a or g
<220> FEATURE:
<221> NAME/KEY: misc_feature
<222> LOCATION: (36)
<223> OTHER INFORMATION: s is c or g
<220> FEATURE:

<220> FEATURE:
<221> NAME/KEY: misc_feature
<222> LOCATION: (37)
<223> OTHER INFORMATION: n is a or c or t or g
<220> FEATURE:
<221> NAME/KEY: misc_feature
<222> LOCATION: (38)
<223> OTHER INFORMATION: d is a or g or t
<220> FEATURE:
<221> NAME/KEY: misc_feature
<222> LOCATION: (136)
<223> OTHER INFORMATION: r is a or g
<220> FEATURE:
<221> NAME/KEY: misc_feature
<222> LOCATION: (138)
<223> OTHER INFORMATION: s is c or g
<220> FEATURE:
<221> NAME/KEY: misc_feature
<222> LOCATION: (139)
<223> OTHER INFORMATION: n is a or c or t or g
<220> FEATURE:
<221> NAME/KEY: misc_feature
<222> LOCATION: (140)
<223> OTHER INFORMATION: d is a or g or t

<400> SEQUENCE: 50

```
ttgaccccgg agcaggtggt ggccatcgcc agcrtsndgg gcggcaagca ggcgctggag      60
acggtccagc ggctgttgcc ggtgctgtgc caggcccacg gcttgacccc ggagcaggtg     120
gtggccatcg ccagcrtsnd gggcggcaag caggcgctgg agacggtcca gcggctgttg     180
ccggtgctgt gccaggccca cggcttgacc ccccagcagg tggtggccat cgccagcaat     240
aatggtggca agcaggcgct ggagacggtc cagcggctgt tgccggtgct gtgccaggcc     300
cacggcttga ccccggagca ggtggtggcc atcgccagcc acgatggcgg caagcaggcg     360
ctggagacgg tccagcggct gttgccggtg ctgtgccagg cccacggctt gaccccggag     420
caggtggtgg ccatcgccag caatattggt ggcaagcagg cgctggagac ggtgcaggcg     480
ctgttgccgg tgctgtgcca ggcccacggc ttgaccccgg agcaggtggt ggccatcgcc     540
agccacgatg gcggcaagca ggcgctggag acggtccagc ggctgttgcc ggtgctgtgc     600
caggcccacg gcttgacccc ccagcaggtg gtggccatcg ccagcaatgg cggtggcaag     660
caggcgctgg agacggtcca gcggctgttg ccggtgctgt gccaggccca cggcttgacc     720
ccccagcagg tggtggccat cgccagcaat ggcggtggca agcaggcgct ggagacggtc     780
cagcggctgt tgccggtgct gtgccaggcc cacggcttga ccccggagca ggtggtggcc     840
atcgccagca atattggtgg caagcaggcg ctggagacgg tgcaggcgct gttgccggtg     900
ctgtgccagg cccacggctt gacccctcag caggtggtgg ccatcgccag caatggcggc     960
ggcaggccgg cgctggag                                                  978
```

<210> SEQ ID NO 51
<211> LENGTH: 978
<212> TYPE: DNA
<213> ORGANISM: artificial sequence
<220> FEATURE:
<223> OTHER INFORMATION: array lib2 2RVD
<220> FEATURE:
<221> NAME/KEY: misc_feature
<222> LOCATION: (34)
<223> OTHER INFORMATION: r is a or g
<220> FEATURE:
<221> NAME/KEY: misc_feature
<222> LOCATION: (36)
<223> OTHER INFORMATION: s is c or g
<220> FEATURE:
<221> NAME/KEY: misc_feature
<222> LOCATION: (37)
<223> OTHER INFORMATION: n is a or c or t or g

```
<220> FEATURE:
<221> NAME/KEY: misc_feature
<222> LOCATION: (38)
<223> OTHER INFORMATION: v is a or c or g
<220> FEATURE:
<221> NAME/KEY: misc_feature
<222> LOCATION: (136)
<223> OTHER INFORMATION: r is a or g
<220> FEATURE:
<221> NAME/KEY: misc_feature
<222> LOCATION: (138)
<223> OTHER INFORMATION: s is c or g
<220> FEATURE:
<221> NAME/KEY: misc_feature
<222> LOCATION: (139)
<223> OTHER INFORMATION: n is a or c or t or g
<220> FEATURE:
<221> NAME/KEY: misc_feature
<222> LOCATION: (140)
<223> OTHER INFORMATION: v is a or c or g

<400> SEQUENCE: 51
ttgaccccgg agcaggtggt ggccatcgcc agcrtsnvtg gcggcaagca ggcgctggag      60
acggtccagc ggctgttgcc ggtgctgtgc caggcccacg gcttgacccc ggagcaggtg     120
gtggccatcg ccagcrtsnv tggcggcaag caggcgctgg agacggtcca gcggctgttg     180
ccggtgctgt gccaggccca cggcttgacc ccccagcagg tggtggccat cgccagcaat     240
aatggtggca agcaggcgct ggagacggtc agcggctgt tgccggtgct gtgccaggcc      300
cacggcttga ccccggagca ggtggtggcc atcgccagcc acgatggcgg caagcaggcg     360
ctggagacgg tccagcggct gttgccggtg ctgtgccagg cccacggctt gaccccggag     420
caggtggtgg ccatcgccag caatattggt ggcaagcagg cgctggagac ggtgcaggcg     480
ctgttgccgg tgctgtgcca ggcccacggc ttgaccccgg agcaggtggt ggccatcgcc     540
agccacgatg gcggcaagca ggcgctggag acggtccagc ggctgttgcc ggtgctgtgc     600
caggcccacg gcttgacccc ccagcaggtg gtggccatcg ccagcaatgg cggtggcaag     660
caggcgctgg agacggtcca gcggctgttg ccggtgctgt gccaggccca cggcttgacc     720
ccccagcagg tggtggccat cgccagcaat ggcggtggca agcaggcgct ggagacggtc     780
cagcggctgt tgccggtgct gtgccaggcc cacggcttga ccccggagca ggtggtggcc     840
atcgccagca atattggtgg caagcaggcg ctggagacgg tgcaggcgct gttgccggtg     900
ctgtgccagg cccacggctt gacccctcag caggtggtgg ccatcgccag caatggcggc     960
ggcaggccgg cgctggag                                                  978

<210> SEQ ID NO 52
<211> LENGTH: 978
<212> TYPE: DNA
<213> ORGANISM: artificial sequence
<220> FEATURE:
<223> OTHER INFORMATION: array lib3 2RVD
<220> FEATURE:
<221> NAME/KEY: misc_feature
<222> LOCATION: (34)
<223> OTHER INFORMATION: r is a or g
<220> FEATURE:
<221> NAME/KEY: misc_feature
<222> LOCATION: (35)
<223> OTHER INFORMATION: s is c or g
<220> FEATURE:
<221> NAME/KEY: misc_feature
<222> LOCATION: (37)
<223> OTHER INFORMATION: n is a or c or t or g
<220> FEATURE:
<221> NAME/KEY: misc_feature
<222> LOCATION: (38)
```

<223> OTHER INFORMATION: d is a or g or t
<220> FEATURE:
<221> NAME/KEY: misc_feature
<222> LOCATION: (136)
<223> OTHER INFORMATION: r is a or g
<220> FEATURE:
<221> NAME/KEY: misc_feature
<222> LOCATION: (137)
<223> OTHER INFORMATION: s is c or g
<220> FEATURE:
<221> NAME/KEY: misc_feature
<222> LOCATION: (139)
<223> OTHER INFORMATION: n is a or c or t or g
<220> FEATURE:
<221> NAME/KEY: misc_feature
<222> LOCATION: (140)
<223> OTHER INFORMATION: d is a or g or t

<400> SEQUENCE: 52

```
ttgaccccgg agcaggtggt ggccatcgcc agcrstndgg gcggcaagca ggcgctggag     60
acggtccagc ggctgttgcc ggtgctgtgc caggcccacg gcttgacccc ggagcaggtg    120
gtggccatcg ccagcrstnd gggcggcaag caggcgctgg agacggtcca gcggctgttg    180
ccggtgctgt gccaggccca cggcttgacc cccagcagg tggtggccat cgccagcaat    240
aatggtggca agcaggcgct ggagacggtc agcggctgt tgccggtgct gtgccaggcc    300
cacggcttga ccccggagca ggtggtggcc atcgccagcc acgatggcgg caagcaggcg    360
ctggagacgg tccagcggct gttgccggtg ctgtgccagg cccacggctt gaccccggag    420
caggtggtgg ccatcgccag caatattggt ggcaagcagg cgctggagac ggtgcaggcg    480
ctgttgccgg tgctgtgcca ggcccacggc ttgaccccgg agcaggtggt ggccatcgcc    540
agccacgatg gcggcaagca ggcgctggag acggtccagc ggctgttgcc ggtgctgtgc    600
caggcccacg gcttgacccc cagcaggtg gtggccatcg ccagcaatgg cggtggcaag    660
caggcgctgg agacggtcca gcggctgttg ccggtgctgt gccaggccca cggcttgacc    720
cccagcagg tggtggccat cgccagcaat ggcggtggca agcaggcgct ggagacggtc    780
cagcggctgt tgccggtgct gtgccaggcc cacggcttga ccccggagca ggtggtggcc    840
atcgccagca atattggtgg caagcaggcg ctggagacgg tgcaggcgct gttgccggtg    900
ctgtgccagg cccacggctt gacccctcag caggtggtgg ccatcgccag caatggcggc    960
ggcaggccgg cgctggag                                                 978
```

<210> SEQ ID NO 53
<211> LENGTH: 978
<212> TYPE: DNA
<213> ORGANISM: artificial sequence
<220> FEATURE:
<223> OTHER INFORMATION: array lib4 2RVD
<220> FEATURE:
<221> NAME/KEY: misc_feature
<222> LOCATION: (34)
<223> OTHER INFORMATION: r is a or g
<220> FEATURE:
<221> NAME/KEY: misc_feature
<222> LOCATION: (36)
<223> OTHER INFORMATION: s is c or g
<220> FEATURE:
<221> NAME/KEY: misc_feature
<222> LOCATION: (37)
<223> OTHER INFORMATION: n is a or c or t or g
<220> FEATURE:
<221> NAME/KEY: misc_feature
<222> LOCATION: (38)
<223> OTHER INFORMATION: v is a or c or g
<220> FEATURE:
<221> NAME/KEY: misc_feature
<222> LOCATION: (39)
<223> OTHER INFORMATION: d is a or g or t
<220> FEATURE:
<221> NAME/KEY: misc_feature
<222> LOCATION: (136)
<223> OTHER INFORMATION: r is a or g
<220> FEATURE:
<221> NAME/KEY: misc_feature
<222> LOCATION: (138)
<223> OTHER INFORMATION: s is c or g
<220> FEATURE:
<221> NAME/KEY: misc_feature
<222> LOCATION: (139)
<223> OTHER INFORMATION: n is a or c or t or g
<220> FEATURE:
<221> NAME/KEY: misc_feature
<222> LOCATION: (140)
<223> OTHER INFORMATION: v is a or c or g
<220> FEATURE:
<221> NAME/KEY: misc_feature
<222> LOCATION: (141)
<223> OTHER INFORMATION: d is a or g or t

<400> SEQUENCE: 53
ttgaccccgg agcaggtggt ggccatcgcc agcrtsnvdg gcggcaagca ggcgctggag    60
acggtccagc ggctgttgcc ggtgctgtgc caggcccacg gcttgacccc ggagcaggtg   120
gtggccatcg ccagcrtsnv dggcggcaag caggcgctgg agacggtcca gcggctgttg   180
ccggtgctgt gccaggccca cggcttgacc ccccagcagg tggtggccat cgccagcaat   240
aatggtggca agcaggcgct ggagacggtc cagcggctgt tgccggtgct gtgccaggcc   300
cacggcttga ccccggagca ggtggtggcc atcgccagcc acgatggcgg caagcaggcg   360
ctggagacgg tccagcggct gttgccggtg ctgtgccagg cccacggctt gaccccggag   420
caggtggtgg ccatcgccag caatattggt ggcaagcagg cgctggagac ggtgcaggcg   480
ctgttgccgg tgctgtgcca ggcccacggc ttgaccccgg agcaggtggt ggccatcgcc   540
agccacgatg gcggcaagca ggcgctggag acggtccagc ggctgttgcc ggtgctgtgc   600
caggcccacg gcttgacccc ccagcaggtg gtggccatcg ccagcaatgg cggtggcaag   660
caggcgctgg agacggtcca gcggctgttg ccggtgctgt gccaggccca cggcttgacc   720
ccccagcagg tggtggccat cgccagcaat ggcggtggca agcaggcgct ggagacggtc   780
cagcggctgt tgccggtgct gtgccaggcc cacggcttga ccccggagca ggtggtggcc   840
atcgccagca atattggtgg caagcaggcg ctggagacgg tgcaggcgct gttgccggtg   900
ctgtgccagg cccacggctt gacccctcag caggtggtgg ccatcgccag caatggcggc   960
ggcaggccgg cgctggag                                                  978

<210> SEQ ID NO 54
<211> LENGTH: 978
<212> TYPE: DNA
<213> ORGANISM: artificial sequence
<220> FEATURE:
<223> OTHER INFORMATION: array lib5 2RVD
<220> FEATURE:
<221> NAME/KEY: misc_feature
<222> LOCATION: (35); (137)
<223> OTHER INFORMATION: d is a or g or t
<220> FEATURE:
<221> NAME/KEY: misc_feature
<222> LOCATION: (36); (138)
<223> OTHER INFORMATION: k is g or t
<220> FEATURE:
<221> NAME/KEY: misc_feature
<222> LOCATION: (37); (139)
<223> OTHER INFORMATION: h is a or c or t
<220> FEATURE:

<221> NAME/KEY: misc_feature
<222> LOCATION: (38); (140)
<223> OTHER INFORMATION: w is a or t
<220> FEATURE:
<221> NAME/KEY: misc_feature
<222> LOCATION: (137)
<223> OTHER INFORMATION: d is a or g or t
<220> FEATURE:
<221> NAME/KEY: misc_feature
<222> LOCATION: (138)
<223> OTHER INFORMATION: k is g or t
<220> FEATURE:
<221> NAME/KEY: misc_feature
<222> LOCATION: (139)
<223> OTHER INFORMATION: h is a or c or t
<220> FEATURE:
<221> NAME/KEY: misc_feature
<222> LOCATION: (140)
<223> OTHER INFORMATION: w is a or t

<400> SEQUENCE: 54
ttgaccccgg agcaggtggt ggccatcgcc agctdkhwcg gcggcaagca ggcgctggag      60
acggtccagc ggctgttgcc ggtgctgtgc caggcccacg gcttgacccc ggagcaggtg     120
gtggccatcg ccagctdkhw cggcggcaag caggcgctgg agacggtcca gcggctgttg     180
ccggtgctgt gccaggccca cggcttgacc ccccagcagg tggtggccat cgccagcaat     240
aatggtggca agcaggcgct ggagacggtc agcggctgt tgccggtgct gtgccaggcc     300
cacggcttga ccccggagca ggtggtggcc atcgccagcc acgatggcgg caagcaggcg     360
ctggagacgg tccagcggct gttgccggtg ctgtgccagg cccacggctt gaccccggag     420
caggtggtgg ccatcgccag caatattggt ggcaagcagg cgctggagac ggtgcaggcg     480
ctgttgccgg tgctgtgcca ggcccacggc ttgaccccgg agcaggtggt ggccatcgcc     540
agccacgatg gcggcaagca ggcgctggag acggtccagc ggctgttgcc ggtgctgtgc     600
caggcccacg gcttgacccc ccagcaggtg gtggccatcg ccagcaatgg cggtggcaag     660
caggcgctgg agacggtcca gcggctgttg ccggtgctgt gccaggccca cggcttgacc     720
ccccagcagg tggtggccat cgccagcaat ggcggtggca agcaggcgct ggagacggtc     780
cagcggctgt tgccggtgct gtgccaggcc cacggcttga ccccggagca ggtggtggcc     840
atcgccagca atattggtgg caagcaggcg ctggagacgg tgcaggcgct gttgccggtg     900
ctgtgccagg cccacggctt gacccctcag caggtggtgg ccatcgccag caatggcggc     960
ggcaggccgg cgctggag                                                   978

<210> SEQ ID NO 55
<211> LENGTH: 978
<212> TYPE: DNA
<213> ORGANISM: artificial sequence
<220> FEATURE:
<223> OTHER INFORMATION: array lib6 2RVD
<220> FEATURE:
<221> NAME/KEY: misc_feature
<222> LOCATION: (35)
<223> OTHER INFORMATION: d is a or g or t
<220> FEATURE:
<221> NAME/KEY: misc_feature
<222> LOCATION: (36)
<223> OTHER INFORMATION: k is g or t
<220> FEATURE:
<221> NAME/KEY: misc_feature
<222> LOCATION: (38)
<223> OTHER INFORMATION: d is a or g or t
<220> FEATURE:
<221> NAME/KEY: misc_feature
<222> LOCATION: (39)
<223> OTHER INFORMATION: k is g or t
<220> FEATURE:
<221> NAME/KEY: misc_feature
<222> LOCATION: (137)
<223> OTHER INFORMATION: d is a or g or t
<220> FEATURE:
<221> NAME/KEY: misc_feature
<222> LOCATION: (138)
<223> OTHER INFORMATION: k is g or t
<220> FEATURE:
<221> NAME/KEY: misc_feature
<222> LOCATION: (140)
<223> OTHER INFORMATION: d is a or g or t
<220> FEATURE:
<221> NAME/KEY: misc_feature
<222> LOCATION: (141)
<223> OTHER INFORMATION: k is g or t

<400> SEQUENCE: 55

```
ttgaccccgg agcaggtggt ggccatcgcc agctdktdkg gcggcaagca ggcgctggag      60
acggtccagc ggctgttgcc ggtgctgtgc caggcccacg gcttgacccc ggagcaggtg     120
gtggccatcg ccagctdktd kggcggcaag caggcgctgg agacggtcca gcggctgttg     180
ccggtgctgt gccaggccca cggcttgacc ccccagcagg tggtggccat cgccagcaat     240
aatggtggca agcaggcgct ggagacggtc agcggctgt tgccggtgct gtgccaggcc     300
cacggcttga ccccggagca ggtggtggcc atcgccagcc acgatggcgg caagcaggcg     360
ctggagacgg tccagcggct gttgccggtg ctgtgccagg cccacggctt gaccccggag     420
caggtggtgg ccatcgccag caatattggt ggcaagcagg cgctggagac ggtgcaggcg     480
ctgttgccgg tgctgtgcca ggcccacggc ttgaccccgg agcaggtggt ggccatcgcc     540
agccacgatg gcggcaagca ggcgctggag acggtccagc ggctgttgcc ggtgctgtgc     600
caggcccacg gcttgacccc ccagcaggtg gtggccatcg ccagcaatgg cggtggcaag     660
caggcgctgg agacggtcca gcggctgttg ccggtgctgt gccaggccca cggcttgacc     720
ccccagcagg tggtggccat cgccagcaat ggcggtggca agcaggcgct ggagacggtc     780
cagcggctgt tgccggtgct gtgccaggcc cacggcttga ccccggagca ggtggtggcc     840
atcgccagca atattggtgg caagcaggcg ctggagacgg tgcaggcgct gttgccggtg     900
ctgtgccagg cccacggctt gacccctcag caggtggtgg ccatcgccag caatggcggc     960
ggcaggccgg cgctggag                                                  978
```

<210> SEQ ID NO 56
<211> LENGTH: 978
<212> TYPE: DNA
<213> ORGANISM: artificial sequence
<220> FEATURE:
<223> OTHER INFORMATION: array lib7 2RVD
<220> FEATURE:
<221> NAME/KEY: misc_feature
<222> LOCATION: (34)
<223> OTHER INFORMATION: n is a or c or t or g
<220> FEATURE:
<221> NAME/KEY: misc_feature
<222> LOCATION: (35)
<223> OTHER INFORMATION: d is a or g or t
<220> FEATURE:
<221> NAME/KEY: misc_feature
<222> LOCATION: (37)
<223> OTHER INFORMATION: r is a or g
<220> FEATURE:
<221> NAME/KEY: misc_feature
<222> LOCATION: (38)
<223> OTHER INFORMATION: s is c or g
<220> FEATURE:
<221> NAME/KEY: misc_feature
<222> LOCATION: (136)

<223> OTHER INFORMATION: n is a or c or t or g
<220> FEATURE:
<221> NAME/KEY: misc_feature
<222> LOCATION: (137)
<223> OTHER INFORMATION: d is a or g or t
<220> FEATURE:
<221> NAME/KEY: misc_feature
<222> LOCATION: (139)
<223> OTHER INFORMATION: r is a or g
<220> FEATURE:
<221> NAME/KEY: misc_feature
<222> LOCATION: (140)
<223> OTHER INFORMATION: s is c or g

<400> SEQUENCE: 56

```
ttgaccccgg agcaggtggt ggccatcgcc agcndgrstg cggcaagca ggcgctggag     60
acggtccagc ggctgttgcc ggtgctgtgc caggcccacg gcttgacccc ggagcaggtg   120
gtggccatcg ccagcndgrs tggcggcaag caggcgctgg agacggtcca gcggctgttg   180
ccggtgctgt gccaggccca cggcttgacc cccagcagg tggtggccat cgccagcaat   240
aatggtggca agcaggcgct ggagacggtc agcggctgt tgccggtgct gtgccaggcc   300
cacggcttga ccccggagca ggtggtggcc atcgccagcc acgatggcgg caagcaggcg   360
ctggagacgg tccagcggct gttgccggtg ctgtgccagg cccacggctt gaccccggag   420
caggtggtgg ccatcgccag caatattggt ggcaagcagg cgctggagac ggtgcaggcg   480
ctgttgccgg tgctgtgcca ggcccacggc ttgaccccgg agcaggtggt ggccatcgcc   540
agccacgatg cggcaagca ggcgctggag acggtccagc ggctgttgcc ggtgctgtgc   600
caggcccacg gcttgacccc ccagcaggtg gtggccatcg ccagcaatgg cggtggcaag   660
caggcgctgg agacggtcca gcggctgttg ccggtgctgt gccaggccca cggcttgacc   720
ccccagcagg tggtggccat cgccagcaat ggcggtggca agcaggcgct ggagacggtc   780
cagcggctgt tgccggtgct gtgccaggcc cacggcttga ccccggagca ggtggtggcc   840
atcgccagca atattggtgg caagcaggcg ctggagacgg tgcaggcgct gttgccggtg   900
ctgtgccagg cccacggctt gaccccctcag caggtggtgg ccatcgccag caatggcggc   960
ggcaggccgg cgctggag                                                  978
```

<210> SEQ ID NO 57
<211> LENGTH: 978
<212> TYPE: DNA
<213> ORGANISM: artificial sequence
<220> FEATURE:
<223> OTHER INFORMATION: array lib8 2RVD
<220> FEATURE:
<221> NAME/KEY: misc_feature
<222> LOCATION: (34)
<223> OTHER INFORMATION: n is a or c or t or g
<220> FEATURE:
<221> NAME/KEY: misc_feature
<222> LOCATION: (35)
<223> OTHER INFORMATION: d is a or g or t
<220> FEATURE:
<221> NAME/KEY: misc_feature
<222> LOCATION: (37)
<223> OTHER INFORMATION: r is a or g
<220> FEATURE:
<221> NAME/KEY: misc_feature
<222> LOCATION: (39)
<223> OTHER INFORMATION: k is g or t
<220> FEATURE:
<221> NAME/KEY: misc_feature
<222> LOCATION: (136)
<223> OTHER INFORMATION: n is a or c or t or g
<220> FEATURE:
<221> NAME/KEY: misc_feature
<222> LOCATION: (137)
<223> OTHER INFORMATION: d is a or g or t
<220> FEATURE:
<221> NAME/KEY: misc_feature
<222> LOCATION: (139)
<223> OTHER INFORMATION: r is a or g
<220> FEATURE:
<221> NAME/KEY: misc_feature
<222> LOCATION: (141)
<223> OTHER INFORMATION: k is g or t

<400> SEQUENCE: 57

```
ttgaccccgg agcaggtggt ggccatcgcc agcndgrakg gcggcaagca ggcgctggag      60
acggtccagc ggctgttgcc ggtgctgtgc caggcccacg gcttgacccc ggagcaggtg     120
gtggccatcg ccagcndgra kggcggcaag caggcgctgg agacggtcca gcggctgttg     180
ccggtgctgt gccaggccca cggcttgacc cccagcagg tggtggccat cgccagcaat     240
aatggtggca agcaggcgct ggagacggtc cagcggctgt tgccggtgct gtgccaggcc     300
cacggcttga ccccggagca ggtggtggcc atcgccagcc acgatggcgg caagcaggcg     360
ctggagacgg tccagcggct gttgccggtg ctgtgccagg cccacggctt gaccccggag     420
caggtggtgg ccatcgccag caatattggt ggcaagcagg cgctggagac ggtgcaggcg     480
ctgttgccgg tgctgtgcca ggcccacggc ttgaccccgg agcaggtggt ggccatcgcc     540
agccacgatg gcggcaagca ggcgctggag acggtccagc ggctgttgcc ggtgctgtgc     600
caggcccacg gcttgacccc ccagcaggtg gtggccatcg ccagcaatgg cggtggcaag     660
caggcgctgg agacggtcca gcggctgttg ccggtgctgt gccaggccca cggcttgacc     720
ccccagcagg tggtggccat cgccagcaat ggcggtggca agcaggcgct ggagacggtc     780
cagcggctgt tgccggtgct gtgccaggcc cacggcttga ccccggagca ggtggtggcc     840
atcgccagca atattggtgg caagcaggcg ctggagacgg tgcaggcgct gttgccggtg     900
ctgtgccagg cccacggctt gacccctcag caggtggtgg ccatcgccag caatggcggc     960
ggcaggccgg cgctggag                                                 978
```

<210> SEQ ID NO 58
<211> LENGTH: 978
<212> TYPE: DNA
<213> ORGANISM: artificial sequence
<220> FEATURE:
<223> OTHER INFORMATION: array lib9 2RVD
<220> FEATURE:
<221> NAME/KEY: misc_feature
<222> LOCATION: (34)
<223> OTHER INFORMATION: n is a or c or t or g
<220> FEATURE:
<221> NAME/KEY: misc_feature
<222> LOCATION: (35)
<223> OTHER INFORMATION: n is a or c or t or g
<220> FEATURE:
<221> NAME/KEY: misc_feature
<222> LOCATION: (36)
<223> OTHER INFORMATION: k is g or t
<220> FEATURE:
<221> NAME/KEY: misc_feature
<222> LOCATION: (37)
<223> OTHER INFORMATION: n is a or c or t or g
<220> FEATURE:
<221> NAME/KEY: misc_feature
<222> LOCATION: (38)
<223> OTHER INFORMATION: n is a or c or t or g
<220> FEATURE:
<221> NAME/KEY: misc_feature
<222> LOCATION: (39)
<223> OTHER INFORMATION: k is g or t
<220> FEATURE:

<221> NAME/KEY: misc_feature
<222> LOCATION: (136)
<223> OTHER INFORMATION: n is a or c or t or g
<220> FEATURE:
<221> NAME/KEY: misc_feature
<222> LOCATION: (137)
<223> OTHER INFORMATION: n is a or c or t or g
<220> FEATURE:
<221> NAME/KEY: misc_feature
<222> LOCATION: (138)
<223> OTHER INFORMATION: k is g or t
<220> FEATURE:
<221> NAME/KEY: misc_feature
<222> LOCATION: (139)
<223> OTHER INFORMATION: n is a or c or t or g
<220> FEATURE:
<221> NAME/KEY: misc_feature
<222> LOCATION: (140)
<223> OTHER INFORMATION: n is a or c or t or g
<220> FEATURE:
<221> NAME/KEY: misc_feature
<222> LOCATION: (141)
<223> OTHER INFORMATION: k is g or t

<400> SEQUENCE: 58

```
ttgaccccgg agcaggtggt ggccatcgcc agcnnknnkg cggcaagcaa ggcgctggag        60
acggtccagc ggctgttgcc ggtgctgtgc caggcccacg gcttgacccc ggagcaggtg       120
gtggccatcg ccagcnnknn kggcggcaag caggcgctgg agacggtcca gcggctgttg       180
ccggtgctgt gccaggccca cggcttgacc ccccagcagg tggtggccat cgccagcaat       240
aatggtggca agcaggcgct ggagacggtc agcggctgt tgccggtgct gtgccaggcc        300
cacggcttga ccccggagca ggtggtggcc atcgccagcc acgatggcgg caagcaggcg       360
ctggagacgg tccagcggct gttgccggtg ctgtgccagg cccacggctt gaccccggag       420
caggtggtgc catcgccag caatattggt ggcaagcagg cgctggagac ggtgcaggcg        480
ctgttgccgg tgctgtgcca ggcccacggc ttgaccccgg agcaggtggt ggccatcgcc       540
agccacgatg gcggcaagca ggcgctggag acggtccagc ggctgttgcc ggtgctgtgc       600
caggcccacg gcttgacccc ccagcaggtg gtggccatcg ccagcaatgg cggtggcaag       660
caggcgctgg agacggtcca gcggctgttg ccggtgctgt gccaggccca cggcttgacc       720
ccccagcagg tggtggccat cgccagcaat ggcggtggca agcaggcgct ggagacggtc       780
cagcggctgt tgccggtgct gtgccaggcc cacggcttga ccccggagca ggtggtggcc       840
atcgccagca atattggtgg caagcaggcg ctggagacgg tgcaggcgct gttgccggtg       900
ctgtgccagg cccacggctt gaccctcag caggtggtgg ccatcgccag caatggcggc        960
ggcaggccgg cgctggag                                                    978
```

<210> SEQ ID NO 59
<211> LENGTH: 774
<212> TYPE: DNA
<213> ORGANISM: artificial sequence
<220> FEATURE:
<223> OTHER INFORMATION: 7,5 blocks

<400> SEQUENCE: 59

```
ttgaccccc agcaggtggt ggccatcgcc agcaatggcg gtggcaagca ggcgctggag         60
acggtccagc ggctgttgcc ggtgctgtgc caggcccacg gcttgacccc ccagcaggtg       120
gtggccatcg ccagcaatgg cggtggcaag caggcgctgg agacggtcca gcggctgttg       180
ccggtgctgt gccaggccca cggcttgacc ccggagcagg tggtggccat cgccagcaat       240
attggtggca agcaggcgct ggagacggtg caggcgctgt tgccggtgct gtgccaggcc       300
```

```
cacggcttga ccccggagca ggtggtggcc atcgccagcc acgatggcgg caagcaggcg      360
ctggagacgg tccagcggct gttgccggtg ctgtgccagg cccacggctt gacccccag      420 caggtggtgg ccatcgccag caatggcggt ggcaagcagg cgctggagac ggtccagcgg      480
ctgttgccgg tgctgtgcca ggcccacggc ttgacccccc agcaggtggt ggccatcgcc      540
agcaatggcg gtggcaagca ggcgctggag acggtccagc ggctgttgcc ggtgctgtgc      600
caggcccacg gcttgacccc ggagcaggtg gtggccatcg ccagcaatat tggtggcaag      660
caggcgctgg agacggtgca ggcgctgttg ccggtgctgt gccaggccca cggcttgacc      720
cctcagcagg tggtggccat cgccagcaat ggcggcggca ggccggcgct ggag           774
```

<210> SEQ ID NO 60
<211> LENGTH: 1722
<212> TYPE: DNA
<213> ORGANISM: artificial sequence
<220> FEATURE:
<223> OTHER INFORMATION: pCLS9944

<400> SEQUENCE: 60

```
atgggcgatc ctaaaaagaa acgtaaggtc atcgattacc catacgatgt tccagattac       60
gctatcgata tcgccgaccc cattcgttcg cgcacaccaa gtcctgcccg cgagcttctg      120
cccggacccc aacccgatgg ggttcagccg actgcagatc gtggggtgtc tccgcctgcc      180
ggcggccccc tggatggctt gccggctcgg cggacgatgt cccggacccg gctgccatct      240
ccccctgccc cctcacctgc gttctcggcg ggcagcttca gtgacctgtt acgtcagttc      300
gatccgtcac ttttaatac atcgcttttt gattcattgc ctcccttcgg cgctcaccat      360
acagaggctg ccacaggcga gtgggatgag gtgcaatcgg gtctgcgggc agccgacgcc      420
cccccaccca ccatgcgcgt ggctgtcact gccgcgcggc cccgcgcgc caagccggcg      480 ccgcgacgac gtgctgcgca accctccgac gcttcgccgg cggcgcaggt ggatctacgc      540
acgctcggct acagccagca gcaacaggag aagatcaaac cgaaggttcg ttcgacagtg      600
gcgcagcacc acgaggcact ggtcggccac gggtttacac acgcgcacat cgttgcgtta      660
agccaacacc cggcagcgtt agggaccgtc gctgtcaagt atcaggacat gatcgcagcg      720
ttgccagagg cgacacacga agcgatcgtt ggcgtcggca aacagtggtc cggcgcacgc      780
gctctggagg ccttgctcac ggtggcggga gagttgagag gtccaccgtt acagttggac      840
acaggccaac ttctcaagat tgcaaaacgt ggcggcgtga ccgcagtgga ggcagtgcat      900
gcatggcgca atgcactgac gggtgccccg ctcaacttga ccggagacgc ccgggggatc      960
aggtcacgtg cgtctcggag cattgttgcc cagttatctc gccctgatcc ggcgttggcc     1020
gcgttgacca acgaccacct cgtcgccttg gcctgcctcg gcgggcgtcc tgcgctggat     1080
gcagtgaaaa agggattggg ggatcctatc agccgttccc agctggtgaa gtccgagctg     1140
gaggagaaga atccgagtt gaggcacaag ctgaagtacg tgcccacga gtacatcgag     1200 ctgatcgaga tcgcccggaa cagcacccag gaccgtatcc tggagatgaa ggtgatggag     1260
ttcttcatga aggtgtacgg ctacagggc aagcacctgg gcggctccag gaagcccgac     1320
ggcgccatct acaccgtggg ctcccccatc gactacggct gatcgtgga caccaaggcc     1380 tactccggcg gctacaacct gcccatcggc caggccgacg aaatgcagag gtacgtggag     1440
gagaaccaga ccaggaacaa gcacatcaac cccaacgagt ggtggaaggt gtacccctcc     1500
agcgtgaccg agttcaagtt cctgttcgtg tccggccact tcaagggcaa ctacaaggcc     1560
```

```
cagctgacca ggctgaacca catcaccaac tgcaacggcg ccgtgctgtc cgtggaggag    1620
ctcctgatcg gcggcgagat gatcaaggcc ggcaccctga ccctggagga ggtgaggagg    1680
aagttcaaca acggcgagat caacttcgcg gccgactgat aa                       1722

<210> SEQ ID NO 61
<211> LENGTH: 2217
<212> TYPE: DNA
<213> ORGANISM: artificial sequence
<220> FEATURE:
<223> OTHER INFORMATION: pCLS7183

<400> SEQUENCE: 61
atggccgacc ccattcgttc gcgcacacca gtcctgccc gcgagcttct gcccggaccc      60
caacccgatg gggttcagcc gactgcagat cgtggggtgt ctccgcctgc cggcggcccc    120
ctggatggct tgccggctcg gcggacgatg tcccggaccc ggctgccatc tccccctgcc    180
ccctcacctg cgttctcggc gggcagcttc agtgacctgt acgtcagtt cgatccgtca     240 cttttttaata catcgctttt tgattcattg cctcccttcg gcgctcacca tacagaggct    300
gccacaggcg agtgggatga ggtgcaatcg ggtctgcggg cagccgacgc cccccaccc    360 accatgcgcg tggctgtcac tgccgcgcgg ccccgcgcg ccaagccggc gccgcgacga     420
cgtgctgcgc aaccctccga cgcttcgccg gcggcgcagg tggatctacg cacgctcggc    480
tacagccagc agcaacagga gaagatcaaa ccgaaggttc gttcgacagt ggcgcagcac    540
cacgaggcac tggtcggcca cgggtttaca cacgcgcaca tcgttgcgtt aagccaacac    600
ccggcagcgt tagggaccgt cgctgtcaag tatcaggaca tgatcgcagc gttgccagag    660
gcgacacacg aagcgatcgt tggcgtcggc aaacagtggt ccggcgcacg cgctctggag    720
gccttgctca cggtggcggg agagttgaga ggtccaccgt tacagttgga cacaggccaa    780
cttctcaaga ttgcaaaacg tggcggcgtg accgcagtgg aggcagtgca tgcatggcgc    840
aatgcactga cgggtgcccc gctcaacttg accgagacg cccgggggat caggtcacgt    900
gcgtctcgga gcattgttgc ccagttatct cgccctgatc cggcgttggc cgcgttgacc    960
aacgaccacc tcgtcgcctt ggcctgcctc ggcgggcgtc ctgcgctgga tgcagtgaaa   1020
aagggattgc cgcacgcgcc ggccttgatc aaaagaacca atcgccgtat cccgaacgc    1080 acatcccatc gcgttgccga ccacgcgcaa gtggttcgcg tgctgggttt tttccagtgc    1140 cactccacc cagcgcaagc atttgatgac gccatgacgc agttcgggat gagcaggcac    1200
gggttgttac agctctttcg cagagtgggc gtcaccgaac tcgaagcccg cagtggaacg    1260
ctccccccag ccagtcagcg ttgggaccgt atcctccagg catcagggat gaaaagggcc    1320
aaaccgtccc ctacttcaac tcaaacgccg gatcaggcgc ttttgcatgc attcgccgat    1380
tcgctggagc gtgaccttga tgcgcctagc ccaatgcacg agggagatca gacgcgggca    1440
agtagccgta acggtcccg atcggatcgt gctgtcaccg gtccctccgc acagcaatcg    1500
ttcgaggtgc gcgttcccga acagcgcgat gcgctccatt gcccctctc ctggagggta    1560 aaacgcccgc gtaccagtat cggggcggc ctccggatc ctatcagccg ttcccagctg     1620
gtgaagtccg agctggagga gaagaaatcc gagttgaggc acaagctgaa gtacgtgccc    1680
cacgagtaca tcgagctgat cgagatcgcc cggaacagca cccaggaccg tatcctggag    1740
atgaaggtga tggagttctt catgaaggtg tacggctaca ggggcaagca cctgggcggc    1800
tccaggaagc ccgacggcgc catctacacc gtgggctccc ccatcgacta cggcgtgatc    1860
gtggacacca aggcctactc cggcggctac aacctgccca tcggccaggc cgacgaaatg    1920
```

```
cagaggtacg tggaggagaa ccagaccagg aacaagcaca tcaaccccaa cgagtggtgg    1980
aaggtgtacc cctccagcgt gaccgagttc aagttcctgt tcgtgtccgg ccacttcaag    2040
ggcaactaca aggcccagct gaccaggctg aaccacatca ccaactgcaa cggcgccgtg    2100
ctgtccgtgg aggagctcct gatcggcggc gagatgatca aggccggcac cctgacccctg   2160 gaggaggtga ggaggaagtt caacaacggc gagatcaact tcgcggccga ctgataa       2217
```

```
<210> SEQ ID NO 62
<211> LENGTH: 37
<212> TYPE: DNA
<213> ORGANISM: artificial sequence
<220> FEATURE:
<223> OTHER INFORMATION: AAG_RAGT2L10 target

<400> SEQUENCE: 62
taagcactta tatgtgtgta acaggtataa gtgctta                              37

<210> SEQ ID NO 63
<211> LENGTH: 37
<212> TYPE: DNA
<213> ORGANISM: artificial sequence
<220> FEATURE:
<223> OTHER INFORMATION: ACG_RAGT2L10 target

<400> SEQUENCE: 63
tacgcactta tatgtgtgta acaggtataa gtgcgta                              37

<210> SEQ ID NO 64
<211> LENGTH: 37
<212> TYPE: DNA
<213> ORGANISM: artificial sequence
<220> FEATURE:
<223> OTHER INFORMATION: AGG_RAGT2L10 target

<400> SEQUENCE: 64
taggcactta tatgtgtgta acaggtataa gtgccta                              37

<210> SEQ ID NO 65
<211> LENGTH: 37
<212> TYPE: DNA
<213> ORGANISM: artificial sequence
<220> FEATURE:
<223> OTHER INFORMATION: ATG_RAGT2L10 target

<400> SEQUENCE: 65
tatgcactta tatgtgtgta acaggtataa gtgcata                              37

<210> SEQ ID NO 66
<211> LENGTH: 37
<212> TYPE: DNA
<213> ORGANISM: artificial sequence
<220> FEATURE:
<223> OTHER INFORMATION: CAG_RAGT2L10 target

<400> SEQUENCE: 66
tcagcactta tatgtgtgta acaggtataa gtgctga                              37

<210> SEQ ID NO 67
<211> LENGTH: 37
<212> TYPE: DNA
<213> ORGANISM: artificial sequence
<220> FEATURE:
<223> OTHER INFORMATION: CCG_RAGT2L10 target
```

```
<400> SEQUENCE: 67
tccgcactta tatgtgtgta acaggtataa gtgcgga                              37

<210> SEQ ID NO 68
<211> LENGTH: 37
<212> TYPE: DNA
<213> ORGANISM: artificial sequence
<220> FEATURE:
<223> OTHER INFORMATION: CGG_RAGT2L10 target

<400> SEQUENCE: 68
tcggcactta tatgtgtgta acaggtataa gtgccga                              37

<210> SEQ ID NO 69
<211> LENGTH: 37
<212> TYPE: DNA
<213> ORGANISM: artificial sequence
<220> FEATURE:
<223> OTHER INFORMATION: CTG_RAGT2L10 target

<400> SEQUENCE: 69
tctgcactta tatgtgtgta acaggtataa gtgcaga                              37

<210> SEQ ID NO 70
<211> LENGTH: 37
<212> TYPE: DNA
<213> ORGANISM: artificial sequence
<220> FEATURE:
<223> OTHER INFORMATION: GAG_RAGT2L10 target

<400> SEQUENCE: 70
tgagcactta tatgtgtgta acaggtataa gtgctca                              37

<210> SEQ ID NO 71
<211> LENGTH: 37
<212> TYPE: DNA
<213> ORGANISM: artificial sequence
<220> FEATURE:
<223> OTHER INFORMATION: GCG_RAGT2L10 target

<400> SEQUENCE: 71
tgcgcactta tatgtgtgta acaggtataa gtgcgca                              37

<210> SEQ ID NO 72
<211> LENGTH: 37
<212> TYPE: DNA
<213> ORGANISM: artificial sequence
<220> FEATURE:
<223> OTHER INFORMATION: GGG_RAGT2L10 target

<400> SEQUENCE: 72
tgggcactta tatgtgtgta acaggtataa gtgccca                              37

<210> SEQ ID NO 73
<211> LENGTH: 37
<212> TYPE: DNA
<213> ORGANISM: artificial sequence
<220> FEATURE:
<223> OTHER INFORMATION: GTG_RAGT2L10 target

<400> SEQUENCE: 73
tgtgcactta tatgtgtgta acaggtataa gtgcaca                              37

<210> SEQ ID NO 74
<211> LENGTH: 37
```

```
<212> TYPE: DNA
<213> ORGANISM: artificial sequence
<220> FEATURE:
<223> OTHER INFORMATION: TAG_RAGT2L10 target

<400> SEQUENCE: 74
ttagcactta tatgtgtgta acaggtataa gtgctaa                              37

<210> SEQ ID NO 75
<211> LENGTH: 37
<212> TYPE: DNA
<213> ORGANISM: artificial sequence
<220> FEATURE:
<223> OTHER INFORMATION: TCG_RAGT2L10 target

<400> SEQUENCE: 75
ttcgcactta tatgtgtgta acaggtataa gtgcgaa                              37

<210> SEQ ID NO 76
<211> LENGTH: 37
<212> TYPE: DNA
<213> ORGANISM: artificial sequence
<220> FEATURE:
<223> OTHER INFORMATION: TGG_RAGT2L10 target

<400> SEQUENCE: 76
ttggcactta tatgtgtgta acaggtataa gtgccaa                              37

<210> SEQ ID NO 77
<211> LENGTH: 37
<212> TYPE: DNA
<213> ORGANISM: artificial sequence
<220> FEATURE:
<223> OTHER INFORMATION: TTG_RAGT2L10 target

<400> SEQUENCE: 77
tttgcactta tatgtgtgta acaggtataa gtgcaaa                              37

<210> SEQ ID NO 78
<211> LENGTH: 1164
<212> TYPE: PRT
<213> ORGANISM: Xanthomonas spp.
<220> FEATURE:
<223> OTHER INFORMATION: Original AvrBs3 TALE

<400> SEQUENCE: 78
```

Met Asp Pro Ile Arg Ser Arg Thr Pro Ser Pro Ala Arg Glu Leu Leu
1               5                   10                  15

Pro Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Gly Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

```
Arg Pro Pro Arg Ala Lys Pro Ala Pro Arg Arg Ala Ala Gln Pro
130                 135                 140

Ser Asp Ala Ser Pro Ala Ala Gln Val Asp Leu Arg Thr Leu Gly Tyr
145                 150                 155                 160

Ser Gln Gln Gln Glu Lys Ile Lys Pro Lys Val Arg Ser Thr Val
            165                 170                 175

Ala Gln His His Glu Ala Leu Val Gly His Gly Phe Thr His Ala His
        180                 185                 190

Ile Val Ala Leu Ser Gln His Pro Ala Ala Leu Gly Thr Val Ala Val
            195                 200                 205

Lys Tyr Gln Asp Met Ile Ala Ala Leu Pro Glu Ala Thr His Glu Ala
210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
            245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285

Leu Thr Pro Glu Gln Val Val Ala Ile Ala Ser His Asp Gly Gly Lys
290                 295                 300

Gln Ala Leu Glu Thr Val Gln Arg Leu Leu Pro Val Leu Cys Gln Ala
305                 310                 315                 320

His Gly Leu Thr Pro Gln Gln Val Val Ala Ile Ala Ser Asn Gly Gly
            325                 330                 335

Gly Lys Gln Ala Leu Glu Thr Val Gln Arg Leu Leu Pro Val Leu Cys
        340                 345                 350

Gln Ala His Gly Leu Thr Pro Gln Gln Val Val Ala Ile Ala Ser Asn
        355                 360                 365

Ser Gly Gly Lys Gln Ala Leu Glu Thr Val Gln Arg Leu Leu Pro Val
370                 375                 380

Leu Cys Gln Ala His Gly Leu Thr Pro Glu Gln Val Val Ala Ile Ala
385                 390                 395                 400

Ser Asn Gly Gly Gly Lys Gln Ala Leu Glu Thr Val Gln Arg Leu Leu
            405                 410                 415

Pro Val Leu Cys Gln Ala His Gly Leu Thr Pro Glu Gln Val Val Ala
            420                 425                 430

Ile Ala Ser Asn Ile Gly Gly Lys Gln Ala Leu Glu Thr Val Gln Ala
            435                 440                 445

Leu Leu Pro Val Leu Cys Gln Ala His Gly Leu Thr Pro Glu Gln Val
450                 455                 460

Val Ala Ile Ala Ser Asn Ile Gly Gly Lys Gln Ala Leu Glu Thr Val
465                 470                 475                 480

Gln Ala Leu Leu Pro Val Leu Cys Gln Ala His Gly Leu Thr Pro Glu
            485                 490                 495

Gln Val Val Ala Ile Ala Ser Asn Ile Gly Gly Lys Gln Ala Leu Glu
        500                 505                 510

Thr Val Gln Ala Leu Leu Pro Val Leu Cys Gln Ala His Gly Leu Thr
        515                 520                 525

Pro Glu Gln Val Val Ala Ile Ala Ser His Asp Gly Gly Lys Gln Ala
530                 535                 540

Leu Glu Thr Val Gln Arg Leu Leu Pro Val Leu Cys Gln Ala His Gly
```

```
                  545                 550                 555                 560
            Leu Thr Pro Glu Gln Val Val Ala Ile Ala Ser His Asp Gly Gly Lys
                            565                 570                 575
            Gln Ala Leu Glu Thr Val Gln Arg Leu Leu Pro Val Leu Cys Gln Ala
                            580                 585                 590
            His Gly Leu Thr Pro Gln Gln Val Val Ala Ile Ala Ser Asn Gly Gly
                            595                 600                 605
            Gly Lys Gln Ala Leu Glu Thr Val Gln Arg Leu Leu Pro Val Leu Cys
                            610                 615                 620
            Gln Ala His Gly Leu Thr Pro Glu Gln Val Val Ala Ile Ala Ser Asn
            625                 630                 635                 640
            Ser Gly Gly Lys Gln Ala Leu Glu Thr Val Gln Ala Leu Leu Pro Val
                            645                 650                 655
            Leu Cys Gln Ala His Gly Leu Thr Pro Glu Gln Val Val Ala Ile Ala
                            660                 665                 670
            Ser Asn Ser Gly Gly Lys Gln Ala Leu Glu Thr Val Gln Arg Leu Leu
                            675                 680                 685
            Pro Val Leu Cys Gln Ala His Gly Leu Thr Pro Glu Gln Val Val Ala
                            690                 695                 700
            Ile Ala Ser His Asp Gly Gly Lys Gln Ala Leu Glu Thr Val Gln Arg
            705                 710                 715                 720
            Leu Leu Pro Val Leu Cys Gln Ala His Gly Leu Thr Pro Glu Gln Val
                            725                 730                 735
            Val Ala Ile Ala Ser His Asp Gly Gly Lys Gln Ala Leu Glu Thr Val
                            740                 745                 750
            Gln Arg Leu Leu Pro Val Leu Cys Gln Ala His Gly Leu Thr Pro Glu
                            755                 760                 765
            Gln Val Val Ala Ile Ala Ser His Asp Gly Gly Lys Gln Ala Leu Glu
                            770                 775                 780
            Thr Val Gln Arg Leu Leu Pro Val Leu Cys Gln Ala His Gly Leu Thr
            785                 790                 795                 800
            Pro Gln Gln Val Val Ala Ile Ala Ser Asn Gly Gly Gly Arg Pro Ala
                            805                 810                 815
            Leu Glu Thr Val Gln Arg Leu Leu Pro Val Leu Cys Gln Ala His Gly
                            820                 825                 830
            Leu Thr Pro Glu Gln Val Val Ala Ile Ala Ser His Asp Gly Gly Lys
                            835                 840                 845
            Gln Ala Leu Glu Thr Val Gln Arg Leu Leu Pro Val Leu Cys Gln Ala
                            850                 855                 860
            His Gly Leu Thr Pro Gln Gln Val Val Ala Ile Ala Ser Asn Gly Gly
            865                 870                 875                 880
            Gly Arg Pro Ala Leu Glu Ser Ile Val Ala Gln Leu Ser Arg Pro Asp
                            885                 890                 895
            Pro Ala Leu Ala Ala Leu Thr Asn Asp His Leu Val Ala Leu Ala Cys
                            900                 905                 910
            Leu Gly Gly Arg Pro Ala Leu Asp Ala Val Lys Lys Gly Leu Pro His
                            915                 920                 925
            Ala Pro Ala Leu Ile Lys Arg Thr Asn Arg Arg Ile Pro Glu Arg Thr
                            930                 935                 940
            Ser His Arg Val Ala Asp His Ala Gln Val Val Arg Val Leu Gly Phe
            945                 950                 955                 960
            Phe Gln Cys His Ser His Pro Ala Gln Ala Phe Asp Asp Ala Met Thr
                            965                 970                 975
```

Gln Phe Gly Met Ser Arg His Gly Leu Leu Gln Leu Phe Arg Arg Val
            980                 985                 990

Gly Val Thr Glu Leu Glu Ala Arg Ser Gly Thr Leu Pro Pro Ala Ser
        995                 1000                1005

Gln Arg Trp Asp Arg Ile Leu Gln Ala Ser Gly Met Lys Arg Ala Lys
    1010                1015                1020

Pro Ser Pro Thr Ser Thr Gln Thr Pro Asp Gln Ala Ser Leu His Ala
1025                1030                1035                1040

Phe Ala Asp Ser Leu Glu Arg Asp Leu Asp Ala Pro Ser Pro Met His
            1045                1050                1055

Glu Gly Asp Gln Thr Arg Ala Ser Ser Arg Lys Arg Ser Arg Ser Asp
            1060                1065                1070

Arg Ala Val Thr Gly Pro Ser Ala Gln Gln Ser Phe Glu Val Arg Val
            1075                1080                1085

Pro Glu Gln Arg Asp Ala Leu His Leu Pro Leu Ser Trp Arg Val Lys
1090                1095                1100

Arg Pro Arg Thr Ser Ile Gly Gly Gly Leu Pro Asp Pro Gly Thr Pro
1105                1110                1115                1120

Thr Ala Ala Asp Leu Ala Ala Ser Ser Thr Val Met Arg Glu Gln Asp
            1125                1130                1135

Glu Asp Pro Phe Ala Gly Ala Asp Asp Phe Pro Ala Phe Asn Glu
            1140                1145                1150

Glu Glu Leu Ala Trp Leu Met Glu Leu Leu Pro Gln
            1155                1160

<210> SEQ ID NO 79
<211> LENGTH: 22
<212> TYPE: DNA
<213> ORGANISM: artificial sequence
<220> FEATURE:
<223> OTHER INFORMATION: oligo E1

<400> SEQUENCE: 79
cccagtcacg acgttgtaaa ac                                                22

<210> SEQ ID NO 80
<211> LENGTH: 53
<212> TYPE: DNA
<213> ORGANISM: artificial sequence
<220> FEATURE:
<223> OTHER INFORMATION: oligo E2
<220> FEATURE:
<221> NAME/KEY: misc_feature
<222> LOCATION: (24); (27)
<223> OTHER INFORMATION: m is a or c
<220> FEATURE:
<221> NAME/KEY: misc_feature
<222> LOCATION: (25); (26); (28); (29)
<223> OTHER INFORMATION: n is a or c or t or g

<400> SEQUENCE: 80
gtctccagcg cctgcttgcc gccmnnmnng ctggcgatgg ccaccacctg ctc               53

<210> SEQ ID NO 81
<211> LENGTH: 22
<212> TYPE: DNA
<213> ORGANISM: artificial sequence
<220> FEATURE:
<223> OTHER INFORMATION: Oligo F1

<400> SEQUENCE: 81
ggcaagcagg cgctggagac gg    22

<210> SEQ ID NO 82
<211> LENGTH: 23
<212> TYPE: DNA
<213> ORGANISM: artificial sequence
<220> FEATURE:
<223> OTHER INFORMATION: oligo F2

<400> SEQUENCE: 82
cacaggaaac agctatgacc atg    23

<210> SEQ ID NO 83
<211> LENGTH: 22
<212> TYPE: DNA
<213> ORGANISM: artificial sequence
<220> FEATURE:
<223> OTHER INFORMATION: Oligo G1

<400> SEQUENCE: 83
cccagtcacg acgttgtaaa ac    22

<210> SEQ ID NO 84
<211> LENGTH: 20
<212> TYPE: DNA
<213> ORGANISM: artificial sequence
<220> FEATURE:
<223> OTHER INFORMATION: oligo G2

<400> SEQUENCE: 84
cccggtaccg catctcgagg    20

<210> SEQ ID NO 85
<211> LENGTH: 102
<212> TYPE: DNA
<213> ORGANISM: artificial sequence
<220> FEATURE:
<223> OTHER INFORMATION: RVD NG

<400> SEQUENCE: 85 ttgaccccccc agcaggtggt ggccatcgcc agcaatggcg gtggcaagca ggcgctggag    60
acggtccagc ggctgttgcc ggtgctgtgc caggcccacg gc    102

<210> SEQ ID NO 86
<211> LENGTH: 3057
<212> TYPE: DNA
<213> ORGANISM: artificial sequence
<220> FEATURE:
<223> OTHER INFORMATION: pAPG10 plasmid with RVD NG

<400> SEQUENCE: 86
ctaaattgta agcgttaata ttttgttaaa attcgcgtta aattttttgtt aaatcagctc    60 atttttttaac caataggccg aaatcggcaa atcccttat aaatcaaaag aatagaccga    120
gatagggttg agtgttgttc cagtttggaa caagagtcca ctattaaaga acgtggactc    180
caacgtcaaa gggcgaaaaa ccgtctatca gggctatggc ccactacagg ccaaccatca    240
ccctaatcaa gttttttggg gtcgaggtgc cgtaaagcac taaatcggaa ccctaaaggg    300
agcccccgat ttagagcttg acggggaaag ccggcgaacg tggcgagaaa ggaagggaag    360
aaagcgaaag gagcgggcgc tagggcgctg gcaagtgtag cggtcacgct gcgcgtaacc    420
accacacccg ccgcgcttaa tgcgccgcta caggcgcctc ccattcgcca ttcaggctgc    480
gcaactgttg ggaagggcgt tcggtgcggg gcctcttcgc tattacgcca gctggcgaaa    540

```
gggggatgtg ctgcaaggcg attaagttgg gtaacgccag ggttttccca gtcacgacgt    600
tgtaaaacga cggccagtga gcgcgacgta atacgactca ctatagggcg aattgggcgc    660
gcctcacagg ccggacgggc cgacgtccgc agcgacatgt tgaccccca gcaggtggtg    720 gccatcgcca gcaatggcgg tggcaagcag gcgctggaga cggtccagcg gctgttgccg    780
gtgctgtgcc aggccacgg cttgaccctc gagatgcggt accggggcca ctggggcccc     840
tagccaaatt aattaacagc ttttgttccc tttagtgagg gttaattgac gcgcttggcg    900
taatcatggt catagctgtt cctgtgtga aattgttatc cgctcacaat tccacacaac     960
atacgagccg gaagcataaa gtgtaaagcc tggggtgcct aatgagtgag ctaactcaca    1020
ttaattgcgt tgcgctcact gcccgctttc cagtcgggaa acctgtcgtg ccagctgcat    1080
taatgaatcg gccaacgcgc ggggagaggc ggtttgcgta ttgggcgctc tccgcttcct    1140
cgctcactga ctcgctgcgc tcggtcgttc ggctgcggcg agcggtatca gctcactcaa    1200
aggcggtaat acggttatcc acagaatcag gggataacgc aggaaagacc atgtgagcaa    1260
aaggccagca aaaggccagg aaccgtaaaa aggccgcgtt gctggcgttt ttccataggc    1320 tccgccccc tgacgagcat cacaaaaatc gacgctcaag tcagaggtgg cgaaacccga    1380
caggactata aagataccag gcgtttcccc ctggaagctc cctcgtgcgc tctcctgttc    1440
cgaccctgcc gcttaccgga tacctgtccg cctttctccc ttcgggaagc gtggcgcttt    1500
ctcatagctc acgctgtagg tatctcagtt cggtgtaggt cgttcgctcc aagctgggct    1560
gtgtgcacga accccccgtt cagcccgacc gctgcgcctt atccggtaac tatcgtcttg    1620
agtccaaccc ggtaagacac gacttatcgc cactggcagc agccactggt aacaggatta    1680
gcagagcgag gtatgtaggc ggtgctacag agttcttgaa gtggtggcct aactacggct    1740
acactagaag aacagtattt ggtatctgcg ctctgctgaa gccagttacc ttcggaaaaa    1800
gagttggtag ctcttgatcc ggcaaacaaa ccaccgctgg tagcggtggt ttttttgttt    1860
gcaagcagca gattacgcgc agaaaaaaag gatctcaaga agatcctttg atcttttcta    1920
cggggtctga cgctcagtgg aacgaaaact cacgttaagg gattttggtc atgagattat    1980
caaaaaggat cttcacctag atcctttta attaaaaatg aagttttaaa tcaatctaaa    2040
gtatatatga gtaaacttgg tctgacagtt accaatgctt aatcagtgag gcacctatct    2100
cagcgatctg tctatttcgt tcatccatag ttgcctgact ccccgtcgtg tagataacta    2160
cgatacggga gggcttacca tctggcccca gtgctgcaat gataccgcga gaaccacgct    2220
caccggctcc agatttatca gcaataaacc agccagccgg aagggccgag cgcagaagtg    2280
gtcctgcaac tttatccgcc tccatccagt ctattaattg ttgccgggaa gctagagtaa    2340
gtagttcgcc agttaatagt ttgcgcaacg ttgttgccat tgctacaggc atcgtggtgt    2400
cacgctcgtc gtttggtatg gcttcattca gctccggttc ccaacgatca aggcgagtta    2460
catgatcccc catgttgtgc aaaaaagcgg ttagctcctt cggtcctccg atcgttgtca    2520
gaagtaagtt ggccgcagtg ttatcactca tggttatggc agcactgcat aattctctta    2580
ctgtcatgcc atccgtaaga tgcttttctg tgactggtga gtactcaacc aagtcattct    2640
gagaatagtg tatgcggcga ccgagttgct cttgcccggc gtcaatacgg gataataccg    2700
cgccacatag cagaacttta aaagtgctca tcattggaaa acgttcttcg ggcgaaaac     2760 tctcaaggat cttaccgctg ttgagatcca gttcgatgta acccactcgt gcacccaact    2820
gatcttcagc atcttttact ttcaccagcg tttctgggtg agcaaaaaca ggaaggcaaa    2880
```

```
atgccgcaaa aaagggaata agggcgacac ggaaatgttg aatactcata ctcttccttt    2940
ttcaatatta ttgaagcatt tatcagggtt attgtctcat gagcggatac atatttgaat    3000
gtatttagaa aaataaacaa ataggggttc cgcgcacatt tccccgaaaa gtgccac      3057
```

<210> SEQ ID NO 87
<211> LENGTH: 292
<212> TYPE: PRT
<213> ORGANISM: artificial sequence
<220> FEATURE:
<223> OTHER INFORMATION: TALE array A2-A10

<400> SEQUENCE: 87

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Gly Gly Gly Arg
        275                 280                 285

Pro Ala Leu Glu
    290
```

<210> SEQ ID NO 88
<211> LENGTH: 258
<212> TYPE: PRT
<213> ORGANISM: artificial sequence
<220> FEATURE:

<223> OTHER INFORMATION: TALE array B03-B10

<400> SEQUENCE: 88

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser His Asp Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
        130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
                180                 185                 190

Gln Arg Leu Leu Pro Val Leu Cys Gln Ala His Gly Leu Thr Pro Glu
            195                 200                 205

Gln Val Val Ala Ile Ala Ser Asn Ile Gly Gly Lys Gln Ala Leu Glu
        210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Gly Gly Arg Pro Ala
                245                 250                 255

Leu Glu

<210> SEQ ID NO 89
<211> LENGTH: 224
<212> TYPE: PRT
<213> ORGANISM: artificial sequence
<220> FEATURE:
<223> OTHER INFORMATION: TALE array C04-C10

<400> SEQUENCE: 89

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser Asn Ile Gly
            35                  40                  45

Gly Lys Gln Ala Leu Glu Thr Val Gln Ala Leu Leu Pro Val Leu Cys
        50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
            85                  90                  95

Leu Cys Gln Ala His Gly Leu Thr Pro Gln Gln Val Val Ala Ile Ala
        100                 105                 110

Ser Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
        130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
                180                 185                 190

Gln Ala Leu Leu Pro Val Leu Cys Gln Ala His Gly Leu Thr Pro Gln
            195                 200                 205

Gln Val Val Ala Ile Ala Ser Asn Gly Gly Gly Arg Pro Ala Leu Glu
    210                 215                 220

<210> SEQ ID NO 90
<211> LENGTH: 190
<212> TYPE: PRT
<213> ORGANISM: artificial sequence
<220> FEATURE:
<223> OTHER INFORMATION: TALE array D05-D10

<400> SEQUENCE: 90

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
        130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Arg Pro Ala Leu Glu
                180                 185                 190

<210> SEQ ID NO 91
<211> LENGTH: 34
<212> TYPE: PRT
<213> ORGANISM: artificial sequence
<220> FEATURE:

<223> OTHER INFORMATION: TALE array B01

<400> SEQUENCE: 91

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 92
<211> LENGTH: 68
<212> TYPE: PRT
<213> ORGANISM: artificial sequence
<220> FEATURE:
<223> OTHER INFORMATION: TALE array C01-C02

<400> SEQUENCE: 92

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
        50                  55                  60

Gln Ala His Gly
65

<210> SEQ ID NO 93
<211> LENGTH: 102
<212> TYPE: PRT
<213> ORGANISM: artificial sequence
<220> FEATURE:
<223> OTHER INFORMATION: TALE array D01-D03

<400> SEQUENCE: 93

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly
            100

<210> SEQ ID NO 94
<211> LENGTH: 37
<212> TYPE: DNA
<213> ORGANISM: artificial sequence
<220> FEATURE:
<223> OTHER INFORMATION: target 1 A

<400> SEQUENCE: 94
tagttactta tatgtgtgta acaggtataa gtaacta                         37

<210> SEQ ID NO 95
<211> LENGTH: 37
<212> TYPE: DNA
<213> ORGANISM: artificial sequence
<220> FEATURE:
<223> OTHER INFORMATION: target 1 C

<400> SEQUENCE: 95
tcgttactta tatgtgtgta acaggtataa gtaacga         37

<210> SEQ ID NO 96
<211> LENGTH: 37
<212> TYPE: DNA
<213> ORGANISM: artificial sequence
<220> FEATURE:
<223> OTHER INFORMATION: target 1 G

<400> SEQUENCE: 96
tggttactta tatgtgtgta acaggtataa gtaacca         37

<210> SEQ ID NO 97
<211> LENGTH: 37
<212> TYPE: DNA
<213> ORGANISM: artificial sequence
<220> FEATURE:
<223> OTHER INFORMATION: target 1 T

<400> SEQUENCE: 97
ttgttactta tatgtgtgta acaggtataa gtaacaa         37

<210> SEQ ID NO 98
<211> LENGTH: 37
<212> TYPE: DNA
<213> ORGANISM: artificial sequence
<220> FEATURE:
<223> OTHER INFORMATION: target 2 A

<400> SEQUENCE: 98
ttagcactta tatgtgtgta acaggtataa gtgctaa         37

<210> SEQ ID NO 99
<211> LENGTH: 37
<212> TYPE: DNA
<213> ORGANISM: artificial sequence
<220> FEATURE:
<223> OTHER INFORMATION: target 2 C

<400> SEQUENCE: 99
ttcgcactta tatgtgtgta acaggtataa gtgcgaa         37

<210> SEQ ID NO 100
<211> LENGTH: 37
<212> TYPE: DNA
<213> ORGANISM: artificial sequence
<220> FEATURE:
<223> OTHER INFORMATION: target 2 G

<400> SEQUENCE: 100
ttggcactta tatgtgtgta acaggtataa gtgccaa         37

<210> SEQ ID NO 101
<211> LENGTH: 37
<212> TYPE: DNA
<213> ORGANISM: artificial sequence
<220> FEATURE:

<223> OTHER INFORMATION: target 2 T

<400> SEQUENCE: 101
tttgcactta tatgtgtgta acaggtataa gtgcaaa          37

<210> SEQ ID NO 102
<211> LENGTH: 37
<212> TYPE: DNA
<213> ORGANISM: artificial sequence
<220> FEATURE:
<223> OTHER INFORMATION: target 3 A

<400> SEQUENCE: 102
tggatactta tatgtgtgta acaggtataa gtatcca          37

<210> SEQ ID NO 103
<211> LENGTH: 37
<212> TYPE: DNA
<213> ORGANISM: artificial sequence
<220> FEATURE:
<223> OTHER INFORMATION: target 3 C

<400> SEQUENCE: 103
tggctactta tatgtgtgta acaggtataa gtagcca          37

<210> SEQ ID NO 104
<211> LENGTH: 37
<212> TYPE: DNA
<213> ORGANISM: artificial sequence
<220> FEATURE:
<223> OTHER INFORMATION: target 3 G

<400> SEQUENCE: 104
tgggtactta tatgtgtgta acaggtataa gtaccca          37

<210> SEQ ID NO 105
<211> LENGTH: 37
<212> TYPE: DNA
<213> ORGANISM: artificial sequence
<220> FEATURE:
<223> OTHER INFORMATION: target 3 T

<400> SEQUENCE: 105
tggttactta tatgtgtgta acaggtataa gtaacca          37

<210> SEQ ID NO 106
<211> LENGTH: 37
<212> TYPE: DNA
<213> ORGANISM: artificial sequence
<220> FEATURE:
<223> OTHER INFORMATION: target 4 A

<400> SEQUENCE: 106
tggtaactta tatgtgtgta acaggtataa gttacca          37

<210> SEQ ID NO 107
<211> LENGTH: 37
<212> TYPE: DNA
<213> ORGANISM: artificial sequence
<220> FEATURE:
<223> OTHER INFORMATION: target 4 C

<400> SEQUENCE: 107
tggtcactta tatgtgtgta acaggtataa gtgacca          37

```
<210> SEQ ID NO 108
<211> LENGTH: 37
<212> TYPE: DNA
<213> ORGANISM: artificial sequence
<220> FEATURE:
<223> OTHER INFORMATION: target 4 G

<400> SEQUENCE: 108
tggtgactta tatgtgtgta acaggtataa gtcacca                              37

<210> SEQ ID NO 109
<211> LENGTH: 37
<212> TYPE: DNA
<213> ORGANISM: artificial sequence
<220> FEATURE:
<223> OTHER INFORMATION: target 4 T

<400> SEQUENCE: 109
tggttactta tatgtgtgta acaggtataa gtaacca                              37

<210> SEQ ID NO 110
<211> LENGTH: 1611
<212> TYPE: DNA
<213> ORGANISM: artificial sequence
<220> FEATURE:
<223> OTHER INFORMATION: pCLS19101

<400> SEQUENCE: 110
accgcgtctc tgaccccaga acaggtcgtg gctatcgcct ctcatgatgg cggaaaacaa      60
gcattggaga ctgtccagag gctgttgccc gtgctgtgtc aggctcatgg cttgacaccc     120
caacaagtgg tcgctattgc ctccaacgga gggggcaaac aggctttgga aacagtgcag     180
cgcttgctgc ctgtgctttg ccaggctcac gggctgacac cacagcaagt ggtggcaatc     240
gcttcaaaca acggaggaaa gcaggccctg gaaaccgtgc agaggcttct tccagtgctg     300
tgccaagccc acggactcac accagagcag gtcgtcgcca tcgcctctaa catcggcgga     360
aagcaagctc tggagacagt gcaggcactg ctgccagtgc tctgccaggc acatgggctc     420
actcctgagc aggtggtcgc aatcgcctca catgatgggg gaaaacaggc cctcgaaact     480
gtgcagagac tgctccccgt gctctgtcag gcacacggcc tcactccaga gcaagtcgtc     540
gctatcgctt caaatattgg agggaaacag gcattggaaa cagtgcaggc tcttttgcca     600
gtgctgtgcc aggcccacgg ccttacaccc gaacaggtcg tcgccatcgc atccaacatg     660
ggagggaagc aagccttgga gactgtgcag agactgttgc ctgtcctttg tcaggcacac     720
gggttgacac ctgaacaggt ggtcgccatt gccagtaaca ttggggggcaa acaggctctt     780 gagaccgtcc aggcactgct gcccgtgctc tgccaggctc acgggctgac cccagaacaa     840
gtcgtggcca ttgcttccaa cattggcgga aagcaggctt tggagacagt ccaggccctc     900
ctgcccgtcc tctgtcaggc tcatggcctc accccagagc aggtggtggc catcgcaagt     960
catgacggcg gcaagcaggc tctcgaaact gtccagaggc tcttgcctgt gctgtgtcaa    1020
gcccacggac tgactcccca gcaagtggtg gctatcgctt cactgccogg aggcaagcaa    1080 gctctggaaa ctgtgcagcg cttgctcccc gtgctctgcc aggcacacgg cttgacacca    1140
caacaagtcg tggccatcgc tagcaacaac ggagggaagc aagccttgga aactgtgcag    1200
cgcctgctcc ctgtgctgtg tcaggcccac gggctgacac cccagcaagt cgtcgccatt    1260
gccagcaacg gcggaggcaa acaggctctg gaaaccgtgc agagactgct gcctgtcctc    1320
tgccaagctc atggcctcac tccacaacag gtcgtggcta tcgcctcaaa caacggggga    1380
```

| | |
|---|---|
| aagcaagccc tggagactgt gcagaggttg cttcccgtgc tttgccaggc tcacggcctc | 1440 |
| acacctcagc aggtggtggc cattgcctcc aacggcggcg ggaagcaggc cctcgaaaca | 1500 |
| gtccagaggc tgctgcccgt gctgtgccaa gcccacggcc tgactcccca gcaggtcgtc | 1560 |
| gctatcgcca gcaatggcgg gggacggccc gccctggaga gcggagacgc c | 1611 |

<210> SEQ ID NO 111
<211> LENGTH: 1611
<212> TYPE: DNA
<213> ORGANISM: artificial sequence
<220> FEATURE:
<223> OTHER INFORMATION: pCLS19102

<400> SEQUENCE: 111

| | |
|---|---|
| accgcgtctc tgaccccaga acaggtcgtg gctatcgcct ctcatgatgg cggaaaacaa | 60 |
| gcattggaga ctgtccagag gctgttgccc gtgctgtgtc aggctcatgg cttgacaccc | 120 |
| caacaagtgg tcgctattgc ctccaacgga gggggcaaac aggctttgga aacagtgcag | 180 |
| cgcttgctgc ctgtgctttg ccaggctcac gggctgacac cacagcaagt ggtggcaatc | 240 |
| gcttcaaaca acggaggaaa gcaggccctg gaaaccgtgc agaggcttct tccagtgctg | 300 |
| tgccaagccc acgactcac accagagcag gtcgtcgcca tcgcctctaa catcggcgga | 360 |
| aagcaagctc tggagacagt gcaggcactg ctgccagtgc tctgccaggc acatgggctc | 420 |
| actcctgagc aggtggtcgc aatcgcctca catgatgggg aaaacaggc cctcgaaact | 480 |
| gtgcagagac tgctccccgt gctctgtcag gcacacggcc tcactccaga gcaagtcgtc | 540 |
| gctatcgctt caaatattgg agggaaacag gcattggaaa cagtgcaggc tcttttgcca | 600 |
| gtgctgtgcc aggcccacgg ccttacaccc gaacaggtcg tcgccatcgc atcctcagac | 660 |
| ggagggaagc aagccttgga gactgtgcag agactgttgc ctgtcctttg tcaggcacac | 720 |
| gggttgacac ctgaacaggt ggtcgccatt gccagtaaca ttgggggcaa acaggctctt | 780 |
| gagaccgtcc aggcactgct gcccgtgctc tgccaggctc acgggctgac cccagaacaa | 840 |
| gtcgtggcca ttgcttccaa cattggcgga aagcaggctt tggagacagt ccaggccctc | 900 |
| ctgcccgtcc tctgtcaggc tcatggcctc accccagagc aggtggtggc catcgcaagt | 960 |
| catgacggcg gcaagcaggc tctcgaaact gtccagaggc tcttgcctgt gctgtgtcaa | 1020 |
| gcccacggac tgactcccca gcaagtggtg gctatcgctt cagtcggagg aggcaagcaa | 1080 |
| gctctggaaa ctgtgcagcg cttgctcccc gtgctctgcc aggcacacgg cttgacacca | 1140 |
| caacaagtcg tggccatcgc tagcaacaac ggagggaagc aagccttgga aactgtgcag | 1200 |
| cgcctgctcc ctgtgctgtg tcaggcccac gggctgacac cccagcaagt cgtcgccatt | 1260 |
| gccagcaacg gcgaggcaa acaggctctg gaaaccgtgc agagactgct gcctgtcctc | 1320 |
| tgccaagctc atggcctcac tccacaacag gtcgtggcta tcgcctcaaa caacggggga | 1380 |
| aagcaagccc tggagactgt gcagaggttg cttcccgtgc tttgccaggc tcacggcctc | 1440 |
| acacctcagc aggtggtggc cattgcctcc aacggcggcg ggaagcaggc cctcgaaaca | 1500 |
| gtccagaggc tgctgcccgt gctgtgccaa gcccacggcc tgactcccca gcaggtcgtc | 1560 |
| gctatcgcca gcaatggcgg gggacggccc gccctggaga gcggagacgc c | 1611 |

<210> SEQ ID NO 112
<211> LENGTH: 3270
<212> TYPE: DNA
<213> ORGANISM: artificial sequence
<220> FEATURE:
<223> OTHER INFORMATION: pCLS20349

<400> SEQUENCE: 112

```
atgggcgatc ctaaaaagaa acgtaaggtc atcgattacc catacgatgt tccagattac    60
gctatcgata tcgccgaccc cattcgttcg cgcacaccaa gtcctgcccg cgagcttctg   120
cccggacccc aacccgatgg ggttcagccg actgcagatc gtggggtgtc tccgcctgcc   180
ggcggccccc tggatggctt gccggctcgg cggacgatgt cccggacccg gctgccatct   240
cccctgccc cctcacctgc gttctcggcg ggcagcttca gtgacctgtt acgtcagttc   300
gatccgtcac ttttaatac atcgcttttt gattcattgc ctcccttcgg cgctcaccat   360
acagaggctg ccacaggcga gtgggatgag gtgcaatcgg gtctgcgggc agccgacgcc   420
cccccaccca ccatgcgcgt ggctgtcact gccgcgcggc ccccgcgcgc caagccggcg   480
ccgcgacgac gtgctgcgca accctccgac gcttcgccgg cggcgcaggt ggatctacgc   540
acgctcggct acagccagca gcaacaggag aagatcaaac cgaaggttcg ttcgacagtg   600
gcgcagcacc acgaggcact ggtcggccac gggtttacac acgcgcacat cgttgcgtta   660
agccaacacc cggcagcgtt agggaccgtc gctgtcaagt atcaggacat gatcgcagcg   720
ttgccagagg cgacacacga agcgatcgtt ggcgtcggca aacagtggtc cggcgcacgc   780
gctctggagg ccttgctcac ggtggcggga gagttgagag gtccaccgtt acagttggac   840
acaggccaac ttctcaagat gcaaaacgt ggcggcgtga ccgcagtgga ggcagtgcat   900
gcatggcgca atgcactgac gggtgccccg ctcaacttga ccccagaaca ggtcgtggct   960
atcgcctctc atgatggcgg aaaacaagca ttggagactg tccagaggct gttgcccgtg  1020
ctgtgtcagg ctcatggctt gacaccccaa caagtggtcg ctattgcctc caacggaggg  1080
ggcaaacagg ctttggaaac agtgcagcgc ttgctgcctg tgctttgcca ggctcacggg  1140
ctgacaccac agcaagtggt ggcaatcgct tcaaacaacg gaggaaagca ggccctggaa  1200
accgtgcaga ggcttcttcc agtgctgtgc caagcccacg gactcacacc agagcaggtc  1260
gtcgccatcg cctctaacat cggcggaaag caagctctgg agacagtgca ggcactgctg  1320
ccagtgctct gccaggcaca tgggctcact cctgagcagg tggtcgcaat cgcctcacat  1380
gatgggggaa aacaggccct cgaaactgtg cagagactgc tccccgtgct ctgtcaggca  1440
cacggcctca ctccagagca agtcgtcgct atcgcttcaa atattggagg gaaacaggca  1500
ttggaaacag tgcaggctct tttgccagtg ctgtgccagg cccacggcct tacacccgaa  1560
caggtcgtcg ccatcgcatc caacatggga gggaagcaag ccttggagac tgtgcagaga  1620
ctgttgcctg tcctttgtca ggcacacggg ttgacacctg aacaggtggt cgccattgcc  1680
agtaacattg ggggcaaaca ggctcttgag accgtccagg cactgctgcc cgtgctctgc  1740
caggctcacg gctgaccccc agaacaagtc gtggccattg cttccaacat ggcggaaag  1800
caggctttgg agacagtcca ggccctcctg cccgtcctct gtcaggctca tggcctcacc  1860
ccagagcagg tggtggccat cgcaagtcat gacggcggca agcaggctct cgaaactgtc  1920
cagaggctct tgcctgtgct gtgtcaagcc cacggactga ctccccagca agtggtggct  1980
atcgcttcac tgcccggagg caagcaagct ctggaaactg tgcagcgctt gctccccgtg  2040
ctctgccagg cacacggctt gacaccacaa caagtcgtgg ccatcgctag caacaacgga  2100
gggaagcaag ccttggaaac tgtgcagcgc ctgctccctg tgctgtgtca ggcccacggg  2160
ctgacacccc agcaagtcgt cgccattgcc agcaacggcg gaggcaaaca ggctctggaa  2220
accgtgcaga gactgctgcc tgtcctctgc caagctcatg cctcactcc acaacaggtc  2280
```

```
gtggctatcg cctcaaacaa cggggggaaag caagccctgg agactgtgca gaggttgctt    2340
cccgtgcttt gccaggctca cggcctcaca cctcagcagg tggtggccat tgcctccaac    2400
ggcggcggga agcaggccct cgaaacagtc cagaggctgc tgcccgtgct gtgccaagcc    2460
cacgccctga ctccccagca ggtcgtcgct atcgccagca atggcggggg acggcccgcc    2520
ctggagagca ttgttgccca gttatctcgc cctgatccgg cgttggccgc gttgaccaac    2580
gaccacctcg tcgccttggc ctgcctcggc gggcgtcctg cgctggatgc agtgaaaaag    2640
ggattggggg atcctatcag ccgttcccag ctggtgaagt ccgagctgga ggagaagaaa    2700
tccgagttga ggcacaagct gaagtacgtg ccccacgagt acatcgagct gatcgagatc    2760
gcccggaaca gcacccagga ccgtatcctg gagatgaagg tgatggagtt cttcatgaag    2820
gtgtacggct acaggggcaa gcacctgggc ggctccagga agcccgacgg cgccatctac    2880
accgtgggct cccccatcga ctacggcgtg atcgtggaca ccaaggccta ctccggcggc    2940
tacaacctgc ccatcggcca ggccgacgaa atgcagaggt acgtggagga gaaccagacc    3000
aggaacaagc acatcaaccc caacgagtgg tggaaggtgt accctccag cgtgaccgag    3060
ttcaagttcc tgttcgtgtc cggccacttc aagggcaact acaaggccca gctgaccagg    3120
ctgaaccaca tcaccaactg caacggcgcc gtgctgtccg tggaggagct cctgatcggc    3180
ggcgagatga tcaaggccgg caccctgacc ctggaggagg tgaggaggaa gttcaacaac    3240
ggcgagatca acttcgcggc cgactgataa                                     3270

<210> SEQ ID NO 113
<211> LENGTH: 3270
<212> TYPE: DNA
<213> ORGANISM: artificial sequence
<220> FEATURE:
<223> OTHER INFORMATION: pCLS20350

<400> SEQUENCE: 113
atgggcgatc ctaaaaagaa acgtaaggtc atcgattacc catacgatgt tccagattac      60
gctatcgata tcgccgaccc cattcgttcg cgcacaccaa gtcctgcccg cgagcttctg     120
cccggacccc aacccgatgg ggttcagccg actgcagatc gtgggggtgt ccgcctgcc     180
ggcggccccc tggatggctt gccggctcgg cggacgatgt cccggacccg ctgccatct     240
cccctgccc cctcacctgc gttctcggcg ggcagcttca gtgacctgtt acgtcagttc    300
gatccgtcac tttttaatac atcgcttttt gattcattgc ctcccttcgg cgctcaccat    360
acagaggctg ccacaggcga gtgggatgag gtgcaatcgg gtctgcgggc agccgacgcc    420
cccccaccca ccatgcgcgt ggctgtcact gccgcgcggc cccgcgcgc caagccggcg    480
ccgcgacgac gtgctgcgca accctccgac gcttcgccgg cggcgcaggt ggatctacgc    540
acgctcggct acagccagca gcaacaggag aagatcaaac cgaaggttcg ttcgacagtg    600
gcgcagcacc acgaggcact ggtcggccac gggtttacac acgcgcacat cgttgcgtta    660
agccaacacc cggcagcgtt agggaccgtc gctgtcaagt atcaggacat gatcgcagcg    720
ttgccagagg cgacacacga agcgatcgtt ggcgtcggca acagtggtc cggcgcacgc    780
gctctggagg ccttgctcac ggtggcggga gagttgagag tccaccgtt acagttggac    840
acaggccaac ttctcaagat tgcaaaacgt ggcggcgtga ccgcagtgga ggcagtgcat    900
gcatggcgca atgcactgac gggtgccccg ctcaacttga ccccagaaca ggtcgtggct    960
atcgcctctc atgatggcgg aaaacaagca ttggagactg tccagaggct gttgcccgtg   1020
ctgtgtcagg ctcatggctt gacaccccaa caagtggtcg ctattgcctc caacggaggg   1080
```

-continued

```
ggcaaacagg ctttggaaac agtgcagcgc ttgctgcctg tgctttgcca ggctcacggg   1140
ctgacaccac agcaagtggt ggcaatcgct tcaaacaacg gaggaaagca ggccctggaa   1200
accgtgcaga ggcttcttcc agtgctgtgc aagcccacg  gactcacacc agagcaggtc   1260
gtcgccatcg cctctaacat cggcggaaag caagctctgg agacagtgca ggcactgctg   1320
ccagtgctct gccaggcaca tgggctcact cctgagcagg tggtcgcaat cgcctcacat   1380
gatggggaa  aacaggccct cgaaactgtg cagagactgc tccccgtgct ctgtcaggca   1440
cacggcctca ctccagagca agtcgtcgct atcgcttcaa atattggagg gaaacaggca   1500
ttggaaacag tgcaggctct tttgccagtg ctgtgccagg cccacggcct tacacccgaa   1560
caggtcgtcg ccatcgcatc ctcagacgga gggaagcaag ccttggagac tgtgcagaga   1620
ctgttgcctg tcctttgtca ggcacacggg ttgacacctg aacaggtggt cgccattgcc   1680
agtaacattg ggggcaaaca ggctcttgag accgtccagg cactgctgcc cgtgctctgc   1740
caggctcacg ggctgacccc agaacaagtc gtggccattg cttccaacat tggcggaaag   1800
caggctttgg agacagtcca ggccctcctg cccgtcctct gtcaggctca tggcctcacc   1860
ccagagcagg tggtggccat cgcaagtcat gacggcggca agcaggctct cgaaactgtc   1920
cagaggctct tgcctgtgct gtgtcaagcc cacggactga ctccccagca agtggtggct   1980
atcgcttcag tcgaggagg  caagcaagct ctggaaactg tgcagcgctt gctcccgtg   2040
ctctgccagg cacacggctt gacaccacaa caagtcgtgg ccatcgctag caacaacgga   2100
gggaagcaag ccttggaaac tgtgcagcgc ctgctccctg tgctgtgtca ggcccacggg   2160
ctgacacccc agcaagtcgt cgccattgcc agcaacggcg gaggcaaaca ggctctggaa   2220
accgtgcaga gactgctgcc tgtcctctgc aagctcatg  gcctcactcc acaacaggtc   2280
gtggctatcg cctcaaacaa cgggggaaag caagccctgg agactgtgca gaggttgctt   2340
cccgtgcttt gccaggctca cggcctcaca cctcagcagg tggtggccat tgcctccaac   2400
ggcggcggga agcaggccct cgaaacagtc cagaggctgc tgcccgtgct gtgccaagcc   2460
cacggcctga ctccccagca ggtcgtcgct atcgccagca atggcggggg acggcccgcc   2520
ctggagagca ttgttgccca gttatctcgc cctgatccgg cgttggccgc gttgaccaac   2580
gaccacctcg tcgccttggc ctgcctcggc gggcgtcctg cgctggatgc agtgaaaaag   2640
ggattggggg atcctatcag ccgttcccag ctggtgaagt ccgagctgga ggagaagaaa   2700
tccgagttga ggcacaagct gaagtacgtg ccccacgagt acatcgagct gatcgagatc   2760
gcccggaaca gcacccagga ccgtatcctg gagatgaagg tgatggagtt cttcatgaag   2820
gtgtacggct acaggggcaa gcacctgggc ggctccagga agcccgacgg cgccatctac   2880
accgtgggct cccccatcga ctacggcgtg atcgtggaca ccaaggccta ctccggcggc   2940
tacaacctgc ccatcggcca ggccgacgaa atgcagaggt acgtggagga gaaccagacc   3000
aggaacaagc acatcaaccc caacgagtgg tggaaggtgt acccctccag cgtgaccgag   3060
ttcaagttcc tgttcgtgtc cggccacttc aagggcaact acaaggccca gctgaccagg   3120
ctgaaccaca tcaccaactg caacggcgcc gtgctgtccg tggaggagct cctgatcggc   3180
ggcgagatga tcaaggccgg caccctgacc ctggaggagg tgaggaggaa gttcaacaac   3240
ggcgagatca acttcgcggc cgactgataa                                   3270
```

<210> SEQ ID NO 114
<211> LENGTH: 3270
<212> TYPE: DNA

<213> ORGANISM: artificial sequence
<220> FEATURE:
<223> OTHER INFORMATION: pCLS20735

<400> SEQUENCE: 114

```
atgggcgatc ctaaaaagaa acgtaaggtc atcgattacc catacgatgt tccagattac      60
gctatcgata tcgccgaccc cattcgttcg cgcacaccaa gtcctgcccg cgagcttctg     120
cccggacccc aacccgatgg ggttcagccg actgcagatc gtggggtgtc tccgcctgcc     180
ggcggccccc tggatggctt gccggctcgg cggacgatgt cccggacccg gctgccatct     240
cccccctgcc cctcacctgc gttctcggcg ggcagcttca gtgacctgtt acgtcagttc     300
gatccgtcac tttttaatac atcgcttttt gattcattgc ctcccttcgg cgctcaccat     360
acagaggctg ccacaggcga gtgggatgag gtgcaatcgg gtctgcgggc agccgacgcc     420
cccccaccca ccatgcgcgt ggctgtcact gccgcgcggc cccgcgcgc caagccggcg      480
ccgcgacgac gtgctgcgca accctccgac gcttcgccgg cggcgcaggt ggatctacgc     540
acgctcggct acagccagca gcaacaggag aagatcaaac cgaaggttcg ttcgacagtg     600
gcgcagcacc acgaggcact ggtcggccac gggtttacac acgcgcacat cgttgcgtta     660
agccaacacc cggcagcgtt agggaccgtc gctgtcaagt atcaggacat gatcgcagcg     720
ttgccagagg cgacacacga agcgatcgtt ggcgtcggca aacagtggtc cggcgcacgc     780
gctctggagg ccttgctcac ggtggcggga gagttgagag gtccaccgtt acagttggac     840
acaggccaac ttctcaagat tgcaaaacgt ggcggcgtga ccgcagtgga ggcagtgcat     900
gcatggcgca atgcactgac gggtgccccg ctcaacttga ccccggagca ggtggtggcc     960
atcgccagcc acgatggcgg caagcaggcg ctggagacgg tccagcggct gttgccggtg    1020
ctgtgccagg cccacggctt gacccccag caggtggtgg ccatcgccag caatggcggt    1080
ggcaagcagg cgctggagac ggtccagcgg ctgttgccgg tgctgtgcca ggcccacggc    1140
ttgaccccc agcaggtggt ggccatcgcc agcaataatg gtggcaagca ggcgctggag    1200
acggtccagc ggctgttgcc ggtgctgtgc caggcccacg gcttgacccc ggagcaggtg    1260
gtggccatcg ccagcaatat tggtggcaag caggcgctgg agacggtgca ggcgctgttg    1320
ccggtgctgt gccaggccca cggcttgacc ccggagcagg tggtggccat cgccagccac    1380
gatggcggca agcaggcgct ggagacggtc agcggctgt tgccggtgct gtgccaggcc    1440
cacggcttga cccccggagca ggtggtggcc atcgccagca atattggtgg caagcaggcg    1500
ctggagacgg tgcaggcgct gttgccggtg ctgtgccagg cccacggctt gaccccggag    1560
caggtggtgg ccatcgccag ccacgatggc ggcaagcagg cgctggagac ggtccagcgg    1620
ctgttgccgg tgctgtgcca ggcccacggc ttgaccccgg agcaggtggt ggccatcgcc    1680
agcaatattg gtggcaagca ggcgctggag acggtgcagg cgctgttgcc ggtgctgtgc    1740
caggcccacg gcttgacccc ggagcaggtg gtggccatcg ccagcaatat tggtggcaag    1800
caggcgctgg agacggtgca ggcgctgttg ccggtgctgt gccaggccca cggcttgacc    1860
ccggagcagg tggtggccat cgccagccac gatggcggca agcaggcgct ggagacggtc    1920
cagcggctgt tgccggtgct gtgccaggcc cacggcttga cccccagca ggtggtggcc    1980
atcgccagca atggcggtgg caagcaggcg ctggagacgg tccagcggct gttgccggtg    2040
ctgtgccagg cccacggctt gacccccag caggtggtgg ccatcgccag caataatggt    2100
ggcaagcagg cgctggagac ggtccagcgg ctgttgccgg tgctgtgcca ggcccacggc    2160
ttgaccccc agcaggtggt ggccatcgcc agcaatggcg gtggcaagca ggcgctggag    2220
```

```
acggtccagc ggctgttgcc ggtgctgtgc caggcccacg gcttgacccc ccagcaggtg    2280
gtggccatcg ccagcaataa tggtggcaag caggcgctgg agacggtcca gcggctgttg    2340
ccggtgctgt gccaggccca cggcttgacc ccccagcagg tggtggccat cgccagcaat    2400
ggcggtggca agcaggcgct ggagacggtc cagcggctgt tgccggtgct gtgccaggcc    2460
cacggcttga cccctcagca ggtggtggcc atcgccagca atggcggcgg caggccggcg    2520
ctggagagca ttgttgccca gttatctcgc cctgatccgg cgttggccgc gttgaccaac    2580
gaccacctcg tcgccttggc ctgcctcggc gggcgtcctg cgctggatgc agtgaaaaag    2640
ggattggggg atcctatcag ccgttcccag ctggtgaagt ccgagctgga ggagaagaaa    2700
tccgagttga ggcacaagct gaagtacgtg ccccacgagt acatcgagct gatcgagatc    2760
gcccggaaca gcacccagga ccgtatcctg gagatgaagg tgatggagtt cttcatgaag    2820
gtgtacggct acaggggcaa gcacctgggc ggctccagga gcccgacgg cgccatctac    2880 accgtgggct cccccatcga ctacggcgtg atcgtggaca ccaaggccta ctccggcggc    2940
tacaacctgc ccatcggcca ggccgacgaa atgcagaggt acgtggagga gaaccagacc    3000
aggaacaagc acatcaaccc caacgagtgg tggaaggtgt accccctccag cgtgaccgag    3060 ttcaagttcc tgttcgtgtc cggccacttc aagggcaact acaaggccca gctgaccagg    3120
ctgaaccaca tcaccaactg caacggcgcc gtgctgtccg tggaggagct cctgatcggc    3180
ggcgagatga tcaaggccgg caccctgacc ctggaggagg tgaggaggaa gttcaacaac    3240
ggcgagatca acttcgcggc cgactgataa                                     3270
```

<210> SEQ ID NO 115
<211> LENGTH: 3288
<212> TYPE: DNA
<213> ORGANISM: artificial sequence
<220> FEATURE:
<223> OTHER INFORMATION: pCLS20736

<400> SEQUENCE: 115

```
atgggcgatc ctaaaaagaa acgtaaggtc atcgataagg agaccgccgc tgccaagttc      60
gagagacagc acatggacag catcgatatc gccgaccccca ttcgttcgcg cacaccaagt    120
cctgcccgcg agcttctgcc cggaccccaa cccgatgggg ttcagccgac tgcagatcgt    180
ggggtgtctc cgcctgccgg cggcccccctg gatggcttgc cggctcggcg gacgatgtcc    240
cggacccggc tgccatctcc ccctgccccc tcacctgcgt tctcggcggg cagcttcagt    300
gacctgttac gtcagttcga tccgtcactt tttaatacat cgcttttga ttcattgcct     360 cccttcggcg ctcaccatac agaggctgcc acaggcgagt gggatgaggt gcaatcgggt    420
ctgcgggcag ccgacgcccc cccacccacc atgcgcgtgg ctgtcactgc cgcgcggccc    480
ccgcgcgcca agccggcgcc gcgacgacgt gctgcgcaac cctccgacgc ttcgccggcg    540
gcgcaggtgg atctacgcac gctcggctac agccagcagc aacaggagaa gatcaaaccg    600
aaggttcgtt cgacagtggc gcagcaccac gaggcactgg tcggccacgg gtttacacac    660
gcgcacatcg ttgcgttaag ccaacacccg gcagcgttag ggaccgtcgc tgtcaagtat    720
caggacatga tcgcagcgtt gccagaggcg acacacgaag cgatcgttgg cgtcggcaaa    780
cagtggtccg gcgcacgcgc tctggaggcc ttgctcacgg tggcgggaga gttgagaggt    840
ccaccgttac agttggacac aggccaactt ctcaagattg caaaacgtgg cggcgtgacc    900
gcagtggagg cagtgcatgc atggcgcaat gcactgacgg gtgcccccgct caacttgacc    960
```

```
ccccagcagg tggtggccat cgccagcaat aatggtggca agcaggcgct ggagacggtc    1020
cagcggctgt tgccggtgct gtgccaggcc cacggcttga ccccggagca ggtggtggcc    1080
atcgccagcc acgatggcgg caagcaggcg ctggagacgg tccagcggct gttgccggtg    1140
ctgtgccagg cccacggctt gaccccggag caggtggtgg ccatcgccag caatattggt    1200
ggcaagcagg cgctggagac ggtgcaggcg ctgttgccgg tgctgtgcca ggcccacggc    1260
ttgaccccgg agcaggtggt ggccatcgcc agccacgatg gcggcaagca ggcgctggag    1320
acggtccagc ggctgttgcc ggtgctgtgc caggcccacg gcttgacccc ggagcaggtg    1380
gtggccatcg ccagccacga tggcggcaag caggcgctgg agacggtcca gcggctgttg    1440
ccggtgctgt gccaggccca cggcttgacc ccggagcagg tggtggccat cgccagcaat    1500
attggtggca agcaggcgct ggagacggtg caggcgctgt tgccggtgct gtgccaggcc    1560
cacggcttga ccccccagca ggtggtggcc atcgccagca tggcggtgg caagcaggcg    1620
ctggagacgg tccagcggct gttgccggtg ctgtgccagg cccacggctt gaccccccag    1680
caggtggtgg ccatcgccag caataatggt ggcaagcagg cgctggagac ggtccagcgg    1740
ctgttgccgg tgctgtgcca ggcccacggc ttgaccccc agcaggtggt ggccatcgcc    1800
agcaataatg gtggcaagca ggcgctggag acggtccagc ggctgttgcc ggtgctgtgc    1860
caggcccacg gcttgacccc cagcaggtg gtggccatcg ccagcaatgg cggtggcaag    1920
caggcgctgg agacggtcca gcggctgttg ccggtgctgt gccaggccca cggcttgacc    1980
ccccagcagg tggtggccat cgccagcaat aatggtggca agcaggcgct ggagacggtc    2040
cagcggctgt tgccggtgct gtgccaggcc cacggcttga ccccccagca ggtggtggcc    2100
atcgccagca tggcggtgg caagcaggcg ctggagacgg tccagcggct gttgccggtg    2160
ctgtgccagg cccacggctt gaccccggag caggtggtgg ccatcgccag ccacgatggc    2220
ggcaagcagg cgctggagac ggtccagcgg ctgttgccgg tgctgtgcca ggcccacggc    2280
ttgaccccc agcaggtggt ggccatcgcc agcaatggcg gtggcaagca ggcgctggag    2340
acggtccagc ggctgttgcc ggtgctgtgc caggcccacg gcttgacccc cagcaggtg    2400
gtggccatcg ccagcaataa tggtggcaag caggcgctgg agacggtcca gcggctgttg    2460
ccggtgctgt gccaggccca cggcttgacc cctcagcagg tggtggccat cgccagcaat    2520
ggcggcggca ggccggcgct ggagagcatt gttgcccagt tatctcgccc tgatccggcg    2580
ttggccgcgt tgaccaacga ccacctcgtc gccttggcct gcctcggcgg gcgtcctgcg    2640
ctggatgcag tgaaaaaggg attgggggat cctatcagcc gttcccagct ggtgaagtcc    2700
gagctggagg agaagaaatc cgagttgagg cacaagctga agtacgtgcc ccacgagtac    2760
atcgagctga tcgagatcgc ccggaacagc acccaggacc gtatcctgga tgatgaaggtg    2820
atggagttct tcatgaaggt gtacggctac aggggcaagc acctgggcgg ctccaggaag    2880
cccgacggcg ccatctacac cgtgggctcc cccatcgact acggcgtgat cgtggacacc    2940
aaggcctact ccggcggcta caacctgccc atcggccagg ccgacgaaat gcagaggtac    3000
gtggaggaga accagaccag gaacaagcac atcaaccca cgagtggtg aaggtgtac     3060
ccctccagcg tgaccgagtt caagttcctg ttcgtgtccg ccacttcaa gggcaactac    3120
aaggcccagc tgaccaggct gaaccacatc accaactgca acggcgccgt gctgtccgtg    3180
gaggagctcc tgatcggcgg cgagatgatc aaggccggca ccctgaccct ggaggaggtg    3240
aggaggaagt tcaacaacgg cgagatcaac ttcgcggccg actgataa              3288
```

```
<210> SEQ ID NO 116
<211> LENGTH: 49
<212> TYPE: DNA
<213> ORGANISM: artificial sequence
<220> FEATURE:
<223> OTHER INFORMATION: Target A

<400> SEQUENCE: 116
tctgacacaa ctgtgttcac tagcaacctc aaacagacac catggtgca            49

<210> SEQ ID NO 117
<211> LENGTH: 49
<212> TYPE: DNA
<213> ORGANISM: artificial sequence
<220> FEATURE:
<223> OTHER INFORMATION: Target B

<400> SEQUENCE: 117
tctgacataa cagtgttcac tagcaacctc aaacagacac catggtgca            49
```